(12) United States Patent
Kato

(10) Patent No.: US 7,074,464 B2
(45) Date of Patent: Jul. 11, 2006

(54) PERFLUOROPROPENYL-CONTAINING COMPOUND, LIQUID CRYSTAL COMPOSITION AND LIQUID CRYSTAL DISPLAY ELEMENT

(75) Inventor: Takashi Kato, Chiba (JP)

(73) Assignees: Chisso Petrochemical Corporation, Tokyo (JP); Chisso Corporation, Osaka (JP)

( * ) Notice: Subject to any disclaimer, the term of this patent is extended or adjusted under 35 U.S.C. 154(b) by 110 days.

(21) Appl. No.: 10/844,473

(22) Filed: May 13, 2004

(65) Prior Publication Data

US 2005/0006624 A1     Jan. 13, 2005

(30) Foreign Application Priority Data

May 14, 2003 (JP) .............................. 2003-135884
Mar. 16, 2004 (JP) .............................. 2004-074575

(51) Int. Cl.
| C09K 19/34 | (2006.01) |
| C09K 19/30 | (2006.01) |
| C07C 23/10 | (2006.01) |
| C07D 239/02 | (2006.01) |
| C07D 319/06 | (2006.01) |

(52) U.S. Cl. ............. 428/1.1; 252/299.61; 252/299.63; 252/299.66; 252/299.67; 570/131; 570/186; 544/303; 549/369

(58) Field of Classification Search ................ 428/1.1; 252/299.61, 299.63, 299.66, 299.67, 299.62; 570/131, 136, 186, 183; 544/303; 549/369
See application file for complete search history.

(56) References Cited

U.S. PATENT DOCUMENTS

| 5,403,512 A | * | 4/1995 | Bartmann et al. ...... 252/299.01 |
| 6,013,198 A | * | 1/2000 | Miyazawa et al. ...... 252/299.63 |
| 6,159,393 A | | 12/2000 | Tarumi et al. |
| 6,180,027 B1 | * | 1/2001 | Kato et al. ............. 252/299.63 |
| 6,348,244 B1 | * | 2/2002 | Miyazawa et al. ............ 428/1.1 |

FOREIGN PATENT DOCUMENTS

| EP | 0 891 314 | 9/2001 |
| JP | 08-059525 | * 3/1996 |

OTHER PUBLICATIONS

English abstract for JP 08-059525, 1996.*
Kisei Kitano et al., "New Liquid Crystalline Compounds Incorporating Some Fluoroalkenyl Wing Groups", Mol. Cryst. Liq. Cryst., vol. 191, pp. 205-209, 1990.

* cited by examiner

Primary Examiner—Shean C. Wu
(74) Attorney, Agent, or Firm—Wenderoth, Lind & Ponack, L.L.P.

(57) ABSTRACT

A compound represented by the formula (1).

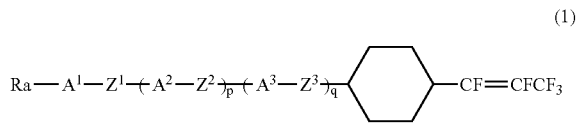

wherein Ra is alkyl having 1 to 10 carbon(s) and, in that alkyl, any of —$CH_2$— may be replaced with —O—, —S—, —CO—, —CH=CH— or —C≡C— or any of hydrogens may be replaced with halogen or —CN; $A^1$, $A^2$ and $A^3$ are independently 1,4-cyclohexylene, 1,4-cyclohexenylene, 1,4-phenylene, naphthalene-2,6-diyl, 1,2,3,4-tetrahydronaphthalene-2,6-diyl, decahydronaphthalene-2,6-diyl or 1,4-bicyclo[2.2.2]octylene and, in such a ring, any —$CH_2$— may be replaced with —O—, any —CH= may be replaced with —N= and any hydrogen may be replaced with halogen; $Z^1$, $Z^2$ and $Z^3$ are independently a single bond, —$(CH_2)_2$—, —$(CF_2)_2$—, —COO—, —OCO—, —$CH_2$O—, —O$CH_2$—, —$CF_2$O—, —OC$F_2$—, —CH=CH—, —CF=CF—, —C≡C—, —$(CH_2)_4$—, —$(CH_2)_3$O— or —O$(CH_2)_3$—; p and q are independently 0 or 1. Also provided is a liquid crystal composition containing the same and a liquid crystal display element containing the composition.

28 Claims, No Drawings

PERFLUOROPROPENYL-CONTAINING COMPOUND, LIQUID CRYSTAL COMPOSITION AND LIQUID CRYSTAL DISPLAY ELEMENT

BACKGROUND OF THE INVENTION

1. Field of the Invention

The present invention relates to liquid crystal compound, liquid crystal composition and liquid crystal display element. More particularly, it relates to a novel liquid crystal compound having a perfluoropropenyl group (—CF=CFCF$_3$) at the end, a liquid crystal composition containing the same and a liquid crystal display element containing the composition.

2. Related Art

According to its display system, liquid crystal display element is classified into several modes such as TN (twisted nematic), TN-TFT (twisted nematic-thin film transistor), bistable TN (bistable twisted nematic), STN (super twisted nematic), IPS (in-plane switching), GH (guest host), DS (dynamic scattering), VA (vertical alignment), OCB (optically compensated bend), ECB (electrically controlled birefringence) and PC (phase change). Physical property which is necessary for liquid crystal composition used for the element varies depending upon such modes.

Such an element contains a composition having an appropriate physical property. In order to improve the characteristic of the element, it is preferred that the composition has an appropriate physical property. The general physical property which is necessary for a compound which is a component of the element is as follows. (1) Chemical stability and physical stability. (2) A high clearing point. Clearing point is a transition temperature from a liquid crystal phase to an isotropic phase. (3) A low lower limit temperature for a liquid crystal phase. The liquid crystal phase means a nematic phase, a smectic phase and so forth. (4) Low viscosity. (5) Appropriate optical anisotropy. (6) High dielectric anisotropy. Compounds having a high dielectric anisotropy often have a high viscosity. (7) High specific resistance.

A composition is prepared by mixing of many compounds. Therefore, it is preferred that a compound is well miscible with other compounds. Since an element is sometimes used at the temperature of lower than an ice point, a compound having a good phase solubility at low temperature is preferred. Compounds having a high clear point or having a low lower limit temperature for liquid crystal phase contribute in a broad temperature range of a nematic phase in a composition. Preferred compounds have a low viscosity and an optical anisotropy suitable for a mode of the element. High electric anisotropy of the compound contributes in a low threshold voltage of the composition. Such a composition is able to give an element having the characteristics such as that usable temperature range is broad, response time is short, contrast ratio is big, driving voltage is low, power consumption is small, voltage retention rate is big and so forth.

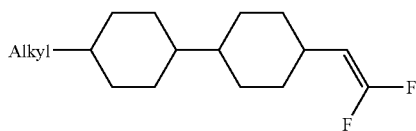

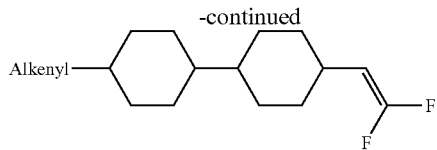

The above compounds have low viscosities. Compounds having viscosities of the same level as those compounds and having higher dielectric anisotropy shorten the response time of the element and, therefore, they are particularly useful.

Compounds which have been known already are disclosed in the following documents. *Mol. Cryst. Liq. Cryst.*, 191, 205 (1990), WO 9734855 A1 (EP 0 891 314 B1), WO 9221734 A1 (U.S. Pat. No. 5,403,512), and GB 19528085 A1 (U.S. Pat. No. 6,159,393).

SUMMARY OF THE INVENTION

The present invention has a compound represented by the formula (1).

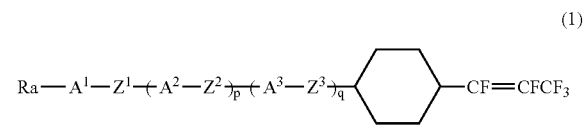

wherein Ra is alkyl having 1 to 10 carbon(s) and, in that alkyl, any of —CH$_2$— may be replaced with —O—, —S—, —CO—, —CH=CH— or —C≡C— or any of hydrogens may be replaced with halogen or —CN; A$^1$, A$^2$ and A$^3$ are independently 1,4-cycolohexylene, 1,4-cyclohexenylene, 1,4-phenylene, naphthalene-2,6-diyl, 1,2,3,4-tetrahydronaphthalene-2,6-diyl, decahydronaphthalene-2,6-diyl or 1,4-bicyclo[2.2.2] octylene and, in such a ring, any —CH$_2$— may be replaced with —O—, any —CH= may be replaced with —N= and any hydrogen may be replaced with halogen; Z$^1$, Z$^2$ and Z$^3$ are independently a single bond, —(CH$_2$)$_2$—, —(CF$_2$)$_2$—, —COO—, —OCO—, —CH$_2$O—, —OCH$_2$—, —CF$_2$O—, —OCF$_2$—, —CH=CH—, —CF=CF—, —C≡C—, —(CH$_2$)$_4$—, —(CH$_2$)$_3$O— or —O(CH$_2$)$_3$—; p and q are independently 0 or 1.

The present invention also has a composition including the compound described above.

The present invention also has a liquid crystal display element including the liquid crystal composition described above.

DETAILED DESCRIPTION

The term "liquid crystal compound" is used as a general name of a compound having a liquid crystal phase and a compound having no liquid crystal phase although being useful as a component for a liquid crystal composition. Liquid crystal compound, liquid crystal composition and liquid crystal display element may be sometimes referred to as the compound, the composition and the element, respectively. The compounds represented by the formulas (1) to (12) may sometimes be referred to as the compound (1) to the compound (12), respectively. In the formulas (2) to (12), structural units enclosed by a hexagon such as B, D and E show ring B, ring D, ring E and so forth. Other hexagons are 1,4-cyclohexylene, 1,4-phenylene and pyridin-2,5-diyl.

The first object of the present invention is a liquid crystal compound having a general physical property necessary for a compound such as low viscosity, appropriate optical anisotropy, appropriate dielectric anisotropy and good phase solubility with other liquid crystal compound. The second object is a liquid crystal composition containing the compound and having a broad temperature range for nematic phase, a low viscosity, an appropriate optical anisotropy and a low threshold voltage. The third object is to provide a liquid crystal display element containing the composition and having a short response time, a small electricity consumption, a high contrast and a high voltage retaining ratio.

The present invention for achieving the above objects has the following.

1. A compound represented by the formula (1).

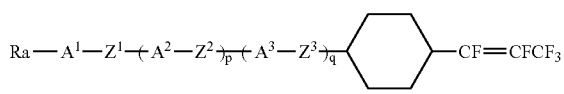

wherein the formula (I), Ra is alkyl having 1 to 10 carbon(s) and, in that alkyl, any of —$CH_2$— may be replaced with —O—, —S—, —CO—, —CH=CH— or —C≡C— or any of hydrogens may be replaced with halogen or —CN.

Meaning of the passage reading "in that alkyl, any of —$CH_2$— may be replaced with —O— or with —CH=CH—" will be illustrated by way of actual examples. A part of the group where —$CH_2$— in $C_4H_9$— is replaced with —O— or with —CH=CH— are $C_3H_7O$—, $CH_3$—O—$(CH_2)_2$—, $CH_3$—O—$CH_2$—O—, $H_2C$=CH—$(CH_2)_3$—, $CH_3$—CH=CH—$(CH_2)_2$— and $CH_3$—CH=CH—$CH_2$—O—. As such, the term "any" means "at least one which is randomly selected". When stability of the compound is taken into consideration, $CH_3$—O—$CH_2$—O— where oxygen and oxygen are not adjacent is preferred over $CH_3$—O—O—$CH_2$— where oxygen and oxygen are adjacent.

Preferred Ra is alkyl, alkoxy, alkoxyalkyl, alkoxyalkoxy, alkylthio, alkylthioalkoxy, acyl, acyloxy, acylalkyl, alkenyl, alkenyloxy, alkenyloxyalkyl, alkoxyalkenyl, alkynyl and alkynyloxy. The above groups where at least one hydrogen is replaced with halogen is preferred as well. Preferred halogen is fluorine and chlorine. Those groups where at least one hydrogen is replaced with —CN are preferred as well. In those groups, a straight-chain ones are preferred over branched ones. Even when Ra is a branched group, that is preferred when it is optically active. More preferred Ra is alkyl, alkoxy, alkenyl and alkenyloxy.

Preferred steric configuration of —CH=CH— in alkenyl depends upon the position of a double bond. A trans-configuration is preferred in an alkenyl such as 1-propenyl, 1-butenyl, 1-pentenyl, 1-hexenyl, 3-pentenyl and 3-hexenyl. A cis-configuration is preferred in an alkenyl such as 2-butenyl, 2-pentenyl and 2-hexenyl. Alkenyl having a preferred steric configuration has a high clear point or has a broad temperature range for liquid crystal phase. Detailed illustration is available in *Mol. Cryst. Liq. Cryst.*, 131, 109 (1985) and *Mol. Cryst. Liq. Cryst.*, 131, 327 (1985).

Specific examples of Ra are methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, 1-propynyl and 1-pentynyl.

Specific examples of Ra are also 2-fluoroethyl, 3-fluoropropyl, 2,2,2-trifluoroethyl, 2-fluorovinyl, 2,2-difluorovinyl, 3-fluoro-1-propenyl, 3,3,3-trifluoro-1-propenyl and 4,4-difluoro-3-butenyl. Among the specific examples of Ra, the particularly preferred Ra are ethyl, propyl and pentyl.

$A^1$, $A^2$ and $A^3$ are independently 1,4-cycolohexylene, 1,4-cyclohexenylene, 1,4-phenylene, naphthalene-2,6-diyl, 1,2,3,4-tetrahydronaphthalene-2,6-diyl, decahydronaphthalene-2,6-diyl or 1,4-bicyclo[2.2.2]octylene and, in such a ring, any —$CH_2$— may be replaced with —O—, any —CH= may be replaced with —N= and any hydrogen may be replaced with halogen.

Preferred $A^1$, $A^2$ or $A^3$ is 1,4-cyclohexylene, 1,4-cyclohexenylene, 1,3-dioxane-2,5-dinyl, 1,4-phenylene, 2-fluoro-1,4-phenylene, 2,3-difluoro-1,4-phenylene, 2,5-difluoro-1,4-phenylene, 2,6-difluoro-1,4-phenylene, 2,3,5-trifluoro-1,4-phenylene, pyridine-2,5-diyl, 3-fluoropyridine-2,5-diyl and pyrimidine-2,5-diyl. With regard to the steric configuration for 1,4-cyclohexylene and 1,3-dioxane-2,5-diyl, trans is preferred over cis. Since 3-fluoro-1,4-phenylene is structurally identical with 3-fluoro-1,4-phenylene, the latter was not exemplified. Such a rule is able to be applied to the relation between 3,6-difluoro-1,4-phenylene to 2,5-difluoro-1,4-phenylene, and so forth as well. That is also applicable to ring structures as such.

More preferred $A^1$, $A^2$ or $A^3$ is 1,4-cyclohexylene, 1,3-dioxane-2,5-diyl, 1,4-phenylene, 2-fluoro-1,4-phenylene, 2,5-difluoro-1,4-phenylene and 2,6-difluoro-1,4-phenylene.

More preferred $A^1$, $A^2$ or $A^3$ is 1,4-cyclohexylene, 1,4-phenylene, 2-fluoro-1,4-phenylene, 2,3-difluoro-1,4-phenylene, 2,5-difluoro-1,4-phenylene and 2,6-difluoro-1,4-phenylene as well.

$Z^1$, $Z^2$ and $Z^3$ are independently a single bond, —$(CH_2)_2$—, —$(CF_2)_2$—, —COO—, —OCO—, —$CH_2O$—, —$OCH_2$—, —$CF_2O$—, —$OCF_2$—, —CH=CH—, —CF=CF—, —C≡C—, —$(CH_2)_4$—, —$(CH_2)_3O$— or —$O(CH_2)_3$—.

Preferred $Z^1$, $Z^2$ or $Z^3$ is a single bond, —$(CH_2)_2$—, —$(CF_2)_2$—, —COO—, —OCO—, —$OCF_2$—, —$CF_2O$—, —CH=CH—, —CF=CF—, —C≡C— and —$(CH_2)_4$—. With regard to the steric configuration for —CH=CH— and —CF=CF—, trans is preferred over cis.

p and q are independently 0 or 1. Compounds where p and q are 0 have two rings. Compounds where p is 1 and q is 0 have three rings. Compounds where p and q are 1 have four rings. Since there is no big difference in physical properties of the compounds, the compound (1) may contain isotope such as $^2H$ (heavy hydrogen) and $^{13}C$ in larger amount than that in the naturally existing ratio. Steric configuration of perfluoropropenyl (—CF=$CFCF_3$) is an E substance or a Z substance. Preferred steric configuration is an E substance.

2. The compound according to item 1, wherein, in the formula (1) mentioned in item 1, Ra is alkyl having 1 to 10 carbon(s) where any —$CH_2$— in the alkyl may be replaced with —O— or —CH=CH— and any hydrogen may be replaced with halogen; $A^1$, $A^2$ and $A^3$ are independently 1,4-cyclohexylene, 1,3-dioxane-2,5-diyl, 1,4-phenylene where any hydrogen may be replaced with halogen, pyridine-2,5-diyl where any hydrogen may be replaced with halogen or pyrimidine-2,5-diyl; and $Z^1$, $Z^2$ and $Z^3$ are independently —$(CH_2)_2$—, —$CH_2O$—, —$OCH_2$—, —COO—, —OCO—, —CF$_2$O—, —OCF$_2$—, —CH=CH—, —C≡C— or —(CH$_2$)$_4$—.

3. The compound according to item 2, wherein, in the formula (1) mentioned in item 1, A$^1$, A$^2$ and A$^3$ are independently 1,4-cyclohexylene, 1,3-dioxane-2,5-diyl or 1,4-phenylene where any hydrogen may be replaced with halogen.

4. The compound according to item 2, wherein, in the formula (1) mentioned in 1., A$^1$, A$^2$ and A$^3$ are 1,4-cyclohexylene.

5. The compound according to items 1 or 2, wherein, in the formula (1) mentioned in item 1, p and q are 0.

6. The compound according to items 1 or 2, wherein, in the formula (1) mentioned in item 1, p is 1 and q is 0.

7. The compound according to items 1 or 2, wherein, in the formula (1) mentioned in item 1, p and q are 1.

8. A compound which is represented by any one of the following formulas (1-a) to (1-c).

(1-a)

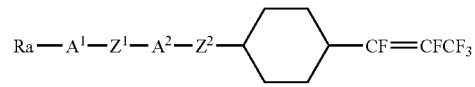

(1-b)

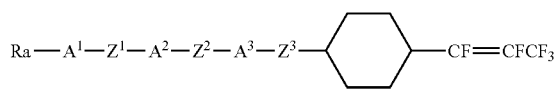

(1-c)

wherein Ra is alkyl having 1 to 10 carbon(s) and, in that alkyl, any —CH$_2$— may be replaced with —O— or —CH=CH— and any hydrogen may be replaced with fluorine; A$^1$, A$^2$ and A$^3$ are independently 1,4-cyclohexylene, 1,3-dioxane-2,5-diyl or 1,4-phenylene where any hydrogen may be replaced with fluorine; and Z$^1$, Z$^2$ and Z$^3$ are independently a single bond, —(CH$_2$)$_2$—, —CH$_2$O—, —OCH$_2$—, —COO—, —OCO—, —CF$_2$O—, —OCF$_2$—, —CH=CH—, —C≡C— or —(CH$_2$)$_4$—.

9. The compound according to item 8, wherein, in the formulas (1-a) to (1-c) mentioned in item 8, Ra is alkyl, alkoxy, alkenyl or alkenyloxy; and A$^1$, A$^2$ and A$^3$ are independently 1,4-cyclohexylene, 1,3-dioxane-2,5-diyl or 1,4-phenylene.

10. The compound according to item 8, wherein, in the formulas (1-a) to (1-c) mentioned in item 8, Ra is alkyl, alkoxy, alkenyl or alkenyloxy; and at least one of A$^1$, A$^2$ and A$^3$ is 2-fluoro-1,4-phenylene or 2,6-difluoro-1,4-phenylene.

11. The compound according to item 8, wherein, in the formulas (1-a) to (1-c) mentioned in item 8, Ra is alkyl, alkoxy, alkenyl or alkenyloxy; and at least one of A$^1$, A$^2$ and A$^3$ is 2,3-difluoro-1,4-phenylene.

12. The compound according to items 8 to 11, wherein, in the formulas (1-a) to (1-c) mentioned in item 8, Z$^1$, Z$^2$ and Z$^3$ are independently a single bond or —(CH$_2$)$_2$—.

13. The compound according to item 8, wherein, in the formulas (1-a) mentioned in item 8, A$^1$ is 1,4-cyclohexylene and Z$^1$ is a single bond.

14. The compound according to item 8, wherein, in the formulas (1-b) mentioned in item 8, A$^1$ and A$^2$ are 1,4-cyclohexylene and Z$^1$ and Z$^2$ are a single bond.

15. A liquid crystal composition containing at least one compounded mentioned in any one of items 1 to 14.

16. The composition according to item 15, wherein it further contains at least one compound selected from the group of the compounds represented by the following formulas (2), (3) and (4).

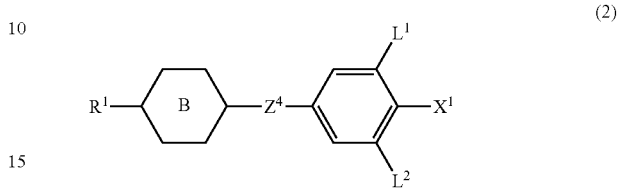

(2)

(3)

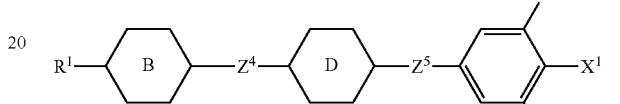

(4)

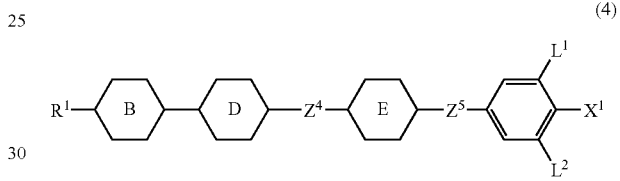

wherein R$^1$ is alkyl having 1 to 10 carbon(s) and, in this alkyl, any —CH$_2$— may be replaced with —O— or —CH=CH— and any hydrogen may be replaced with fluorine; X$^1$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$; ring B and ring D are independently 1,4-cyclohexylene, 1,3-dioxane-2,5-diyl or 1,4-phenylene where any hydrogen may be replaced with fluorine and ring E is 1,4-cyclohexylene or 1,4-phenylene where any hydrogen may be replaced with fluorine; Z$^4$ and Z$^5$ are independently —(CH$_2$)$_2$—, —(CH$_2$)$_4$—, —COO—, —CF$_2$O—, —OCF$_2$—, —CH=CH— or a single bond; and L$^1$ and L$^2$ are independently hydrogen or fluorine, 17. The compound according to item 15 which further contains at least one compound selected from the group of compounds represented by the following formulas (5) and (6).

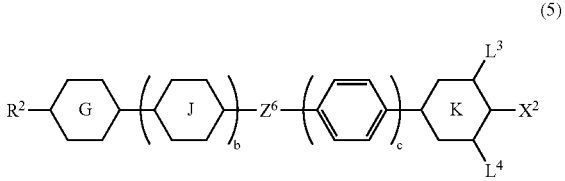

(5)

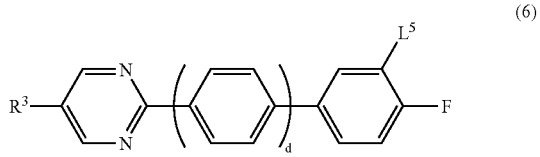

(6)

wherein $R^2$ and $R^3$ are independently alkyl having 1 to 10 carbon(s) and, in that alkyl, any —$CH_2$— may be replaced with —O— or —CH=CH— and any hydrogen may be replaced with fluorine; $X^2$ is —CN or —C≡C—CN; ring G is 1,4-cyclohexylene, 1,4-phenylene, 1,3-dioxane-2,5-diyl or pyrimidine-2,5-diyl; ring J is 1,4-cyclohexylene, pyrimidine-2,5-diyl or 1,4-phenylene where any hydrogen may be replaced with fluorine; ring K is 1,4-cyclohexylene or 1,4-phenylene; $Z^6$ is —$(CH_2)_2$—, —COO—, —$CF_2$O—, —$OCF_2$— or a single bond; $L^3$, $L^4$ and $L^5$ are independently hydrogen or fluorine; and b, c and d are independently 0 or 1.

18. The composition according to item 15, wherein it further contains at least one compound selected from the group of compounds represented by the following formulas (7), (8) and (9).

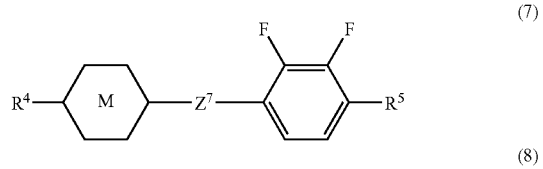

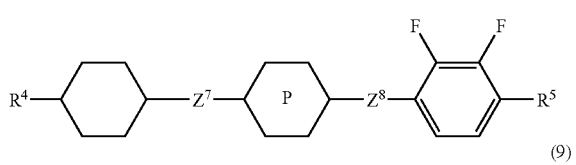

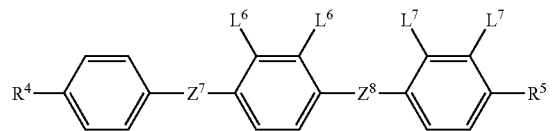

wherein $R^4$ and $R^5$ are independently alkyl having 1 to 10 carbon(s) and, in that alkyl, any —$CH_2$— may be replaced with —O— or —CH=CH— and any hydrogen may be replaced with fluorine; ring M and ring P are independently 1,4-cyclohexylene or 1,4-phenylene; $Z^7$ and $Z^8$ are independently —$(CH_2)_2$—, —COO— or a single bond; and $L^6$ and $L^7$ are independently hydrogen or fluorine where at least one of $L^6$ and $L^7$ is fluorine.

19. The composition according to item 15, wherein it further contains at least one compound selected from the group of compounds represented by the following formulas (10), (11) and (12).

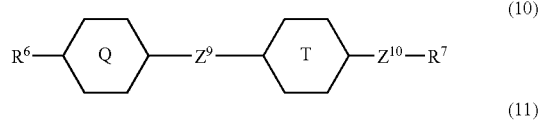

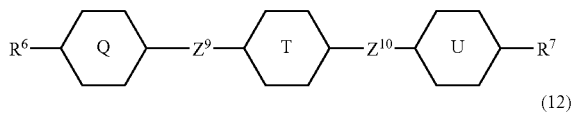

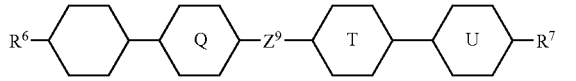

wherein $R^6$ and $R^7$ are independently alkyl having 1 to 10 carbon(s) and, in that alkyl, any —$CH_2$— may be replaced with —O— or —CH=CH— and any hydrogen may be replaced with fluorine; ring Q, ring T and ring U are independently 1,4-cyclohexylene, pyrimidine-2,5-diyl or 1,4-phenylene where any hydrogen may be replaced with fluorine; and $Z^9$ and $Z^{10}$ are independently —C≡C—, —COO—, —$(CH_2)_2$, —CH=CH— or a single bond.

20. The composition according to item 16, wherein it further contains at least one compound selected from the group of the compounds represented by the formulas (10), (11) and (12) mentioned in item 19.

21. The composition according to item 17, wherein it further contains at least one compound selected from the group of the compounds represented by the formulas (10), (11) and (12) mentioned in item 19.

22. The composition according to item 18, wherein it further contains at least one compound selected from the group of the compounds represented by the formulas (10), (11) and (12) mentioned in item 19.

23. The composition according to item 16, wherein it further contains at least one compound selected from the group of the compounds represented by the formulas (5) and (6) mentioned in item 17.

24. The composition according to item 23, wherein it further contains at least one compound selected from the group of the compounds represented by the formulas (10), (11) and (12) mentioned in item 19.

25. The composition according to any one of items 15 to 24, wherein it further contains at least one optically active compound.

26. A liquid crystal display element which contains the composition mentioned in any one of items 15 to 25.

Preferred groups in the compound (2) to the compound (12) are as follows. A straight-chain alkyl is preferred over a branched alkyl. With regard to a steric configuration of 1,4-cyclohexylene and 1,3-dioxane-2,5-diyl, trans is preferred over cis. Meaning of the passage reading "in that alkyl, any —$CH_2$— may be replaced with —O— or —CH=CH—" was already mentioned in 1. which is one of embodiments of the present invention. Symbols such as $R^1$ and ring B are used for plural compounds. $R^1$ (or ring B and so forth.) as such may be same or different. Since there is no big difference in physical properties of the compounds, those compounds may contain isotope such as $^2H$ (heavy hydrogen) and $^{13}C$ in more amount than the amount of the naturally existing ratio.

The compound (1) has a general characteristic necessary for the compound, low viscosity, appropriate optical anisotropy, appropriate dielectric anisotropy and excellent phase solubility with other liquid crystal compounds. A composition containing such a compound has broad temperature range for a nematic phase, low viscosity, appropriate optical anisotropy and low threshold voltage. An display element containing the composition has short response time, low electricity consumption, high contrast and high voltage retaining rate.

Firstly, the compound (1) of the present invention will be further illustrated. The compound (1) is a bicyclic, tricyclic or tetracyclic compound having perfluoropropenyl (—CF=CFCF₃) as a end group. This compound is very stable both physically and chemically under the condition where the display element is usually used. This compound has physical properties that viscosity is low, optical anisotropy is appropriate, dielectric anisotropy is appropriate and miscibility with other liquid crystal compound is good. Values of the optical anisotropy are dependent upon the chemical structure of the compound (1). Dielectric anisotropy of the compound (1) is relatively big to positive and big or nearly zero (small) to negative.

Dielectric anisotropy of the compound (1) has such a characteristic that it is big as compared with that of the compound having alkyl or 2,2-difluoroethenyl (—CH=CF$_2$) as a end group. The compound (1) where A$^1$, A$^2$ and A$^3$ are 1,4-cyclohexylene has a physical property that dielectric anisotropy is relatively big to positive and optical anisotropy is particularly small. Compounds having such a physical property are useful in the preparation of a composition. On the other hand, the compound (1) having 2,3-difluoro-1,4-phenylene has a big dielectric anisotropy to negative.

It is possible to freely adjust the physical property value by an appropriate selection of end group, ring and bonding group of the compound (1). Effect of the end group Ra, the rings A$^1$ to A$^3$ and the bonding groups Z$^1$ to Z$^3$ on the physical property of the compound (1) will be illustrated. When the compound (1) is added to the composition, the physical property of the compound (1) is reflected on to that of the composition.

When Ra of the compound (1) is straight-chain, temperature range of liquid crystal phase is broad and viscosity is low. When Ra is branched, miscibility with other liquid crystal compounds is good. A compound where Ra is an optically active group is useful as a chiral dopant. When the compound is added to the composition, reversed twisted domain generated in the display element can be prevented. A compound where Ra is not an optically active group is useful as a component for the composition.

When the ring A$^1$, A$^2$ or A$^3$ of the compound (1) is 1,3-dioxane-2,5-diyl, pyridine-2,5-diyl or 1,4-phenylene where any hydrogen may be replaced with halogen, dielectric anisotropy is high. When the ring is pyridazine-3,6-diyl, pyrimidine-2,5-diyl, pyridine-2,5-diyl or 1,4-phenylene where any hydrogen may be replaced with halogen, optical anisotropy is high. When the ring is 1,4-cyclohexylene, 1,4-cyclohexenylene or 1,3-dioxane-2,5-diyl, optical anisotropy is low.

When at least two rings are 1,4-cyclohexylene, clear point is high, optical anisotropy is low and viscosity is low. When at least one ring is 1,4-phenylene, optical anisotropy is relatively high and orientational order parameter is high. When at least two rings are 1,4-phenylene, optical anisotropy is high, temperature range for liquid crystal phase is broad and clear point is high.

When the bonding group Z$^1$, Z$^2$ or Z$^3$ is a single bond, —(CH$_2$)$_2$—, —CH$_2$O—, —CF$_2$O—, —OCF$_2$—, —CH=CH—, —CF=CF— or —(CH$_2$)$_4$—, viscosity is low. When the bonding group is a single bond, —(CH$_2$)$_2$—, —OCF$_2$—, —CF$_2$O—, —CH=CH— or —(CH$_2$)$_4$—, viscosity is lower. When the bonding group is —CF=CF— or —CH=CH—, temperature range of liquid crystal phase is broad and elastic constant ratio is big. When the bonding group is —C≡C—, optical anisotropy is high.

When the compound (1) has two rings or three rings, viscosity is low. The compound having two rings has lower viscosity. When the compound (1) has three rings or four rings, clear point is high. The compound having four rings has higher clear point. When it has three rings, there are low viscosity and high clear point. As mentioned above, it is possible to prepare a compound having an aimed physical property by an appropriate selection of type of end group, ring and bonding group and numbers of the ring. Accordingly, the compound (1) is particularly useful as a component for the composition used for display element in a mode such as TN, STN, TN-TFT, IPS and VA.

Preferred examples of the compound (1) will be shown as follows. The first examples are compounds (1-a) to (1-c). More specific second examples are compounds (1-a-1) to (1-c-6). Particularly specific third examples are compounds (1-aa-1) to (1-cc-8). Meanings of the symbols Ra, A$^1$, A$^2$, A$^3$, Z$^1$, Z$^2$ and Z$^3$ used in those compounds are the same as those mentioned in item 1 of the embodiments of the present invention. In the second example, the following symbols were also used.

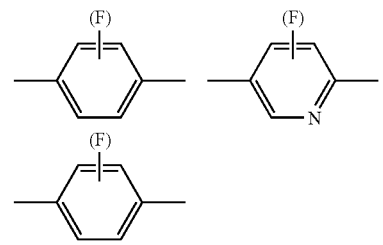

The symbol 1,4-phenylene or pyridine-2,5-diyl where F in the parentheses is bonded by a vertical line is 1,4-phenylene or pyridine-2,5-diyl where any hydrogen may be replaced with fluorine. The symbol 1,4-phenylene where F is bonded by a vertical line is 1,4-phenylene where any hydrogen is replaced with fluorine.

Preferred Ra in the compounds (1-a) to (1-c), the compounds (1-a-1) to (1-c-6) and the compounds (1-aa-1) to (1-cc-8) is alkyl, alkoxy, alkoxyalkyl, alkoxyalkoxy, alkylthio, alkylthioalkoxy, alkenyl, alkenyloxy, alkenyloxyalkyl, alkoxyalkenyl, alkynyl or alkynyloxy. The group as above where at least one hydrogen is replaced with fluorine is preferred as well. More preferred Ra is alkyl, alkoxy, alkenyl and alkenyloxy. In such a group, any hydrogen may be replaced with fluorine.

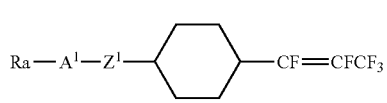

(1-a)

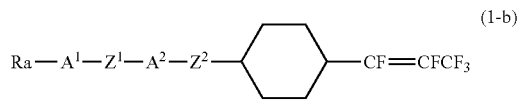

(1-b)

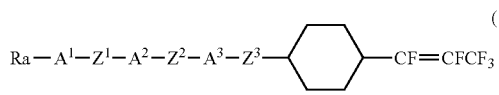

(1-c)

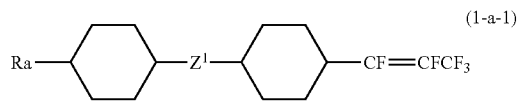

(1-a-1)

-continued
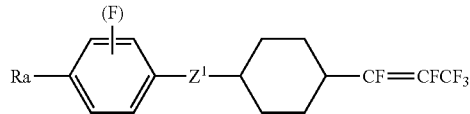
(1-a-2)
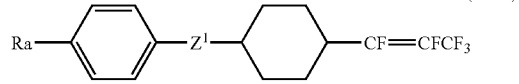
(1-a-3)
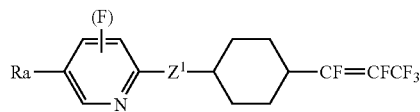
(1-a-4)
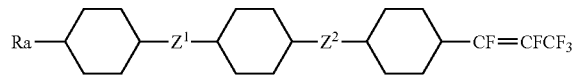
(1-b-1)
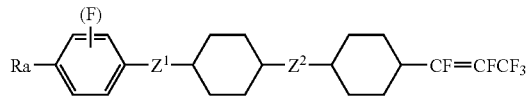
(1-b-2)
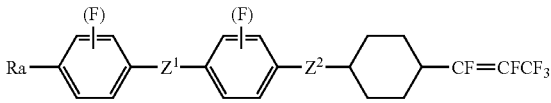
(1-b-3)
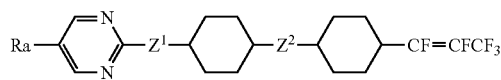
(1-b-4)
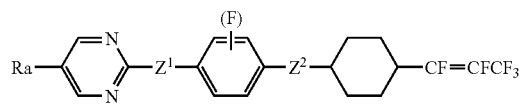
(1-b-5)
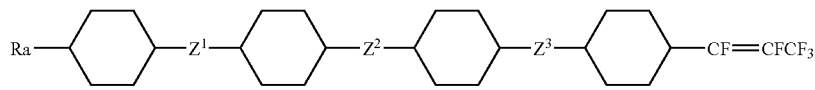
(1-c-1)
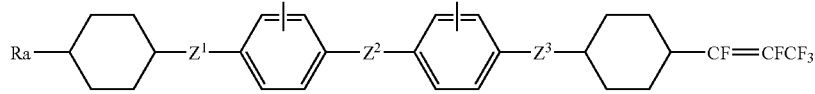
(1-c-2)
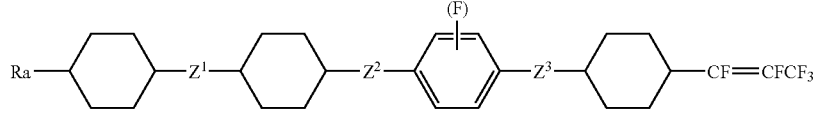
(1-c-3)
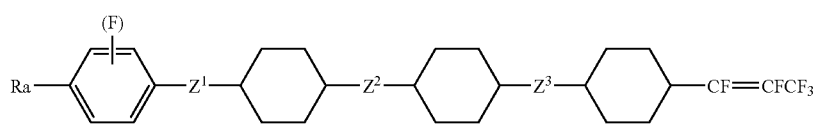
(1-c-4)
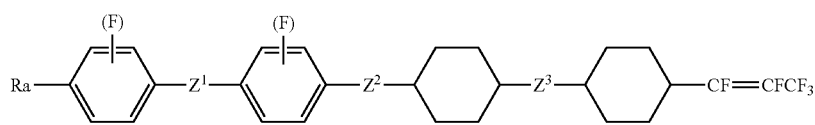
(1-c-5)
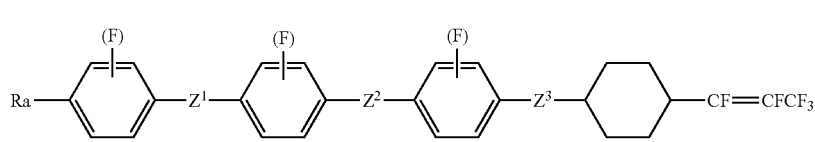
(1-c-6)
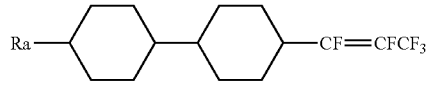
(1-aa-1)
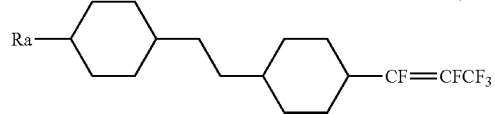
(1-aa-2)
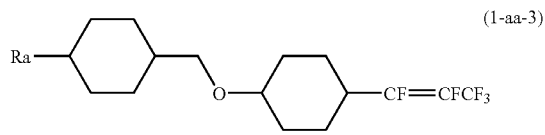
(1-aa-3)
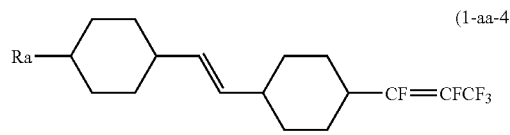
(1-aa-4)

-continued
(1-aa-5)
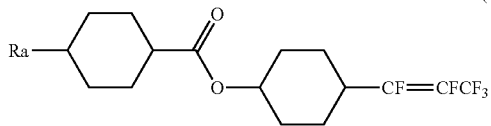
(1-aa-6)
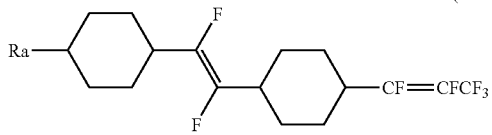
(1-aa-7)
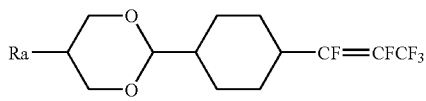
(1-ab-1)
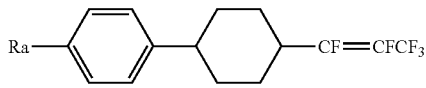
(1-ab-2)
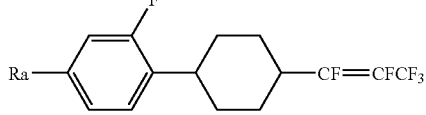
(1-ab-3)
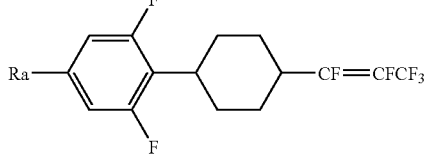
(1-ab-4)
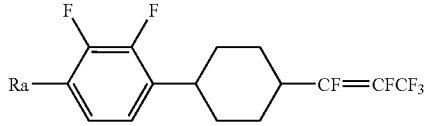
(1-ab-5)
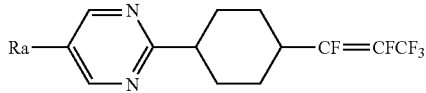
(1-ab-6)
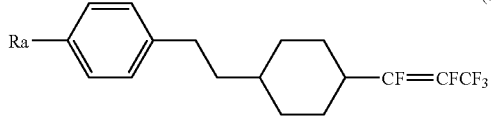
(1-ab-7)
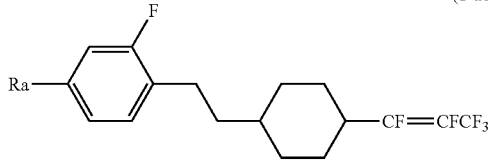
(1-ab-8)
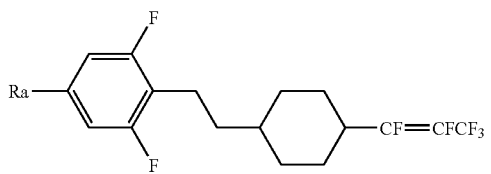
(1-ab-9)
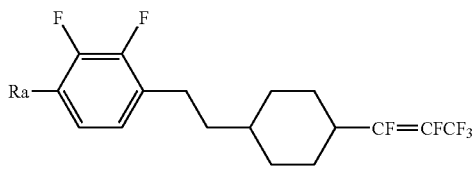
(1-ab-10)
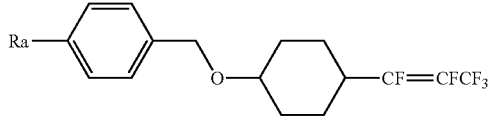
(1-ab-11)
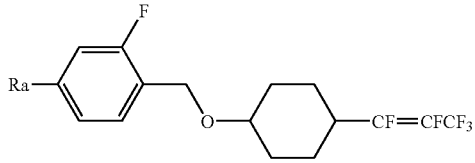
(1-ab-12)
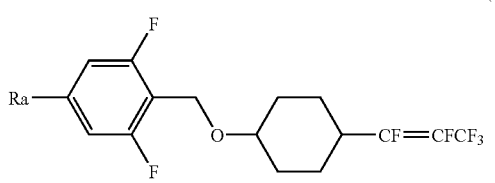
(1-ab-13)
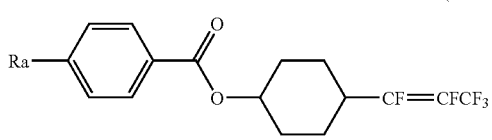
(1-ab-14)
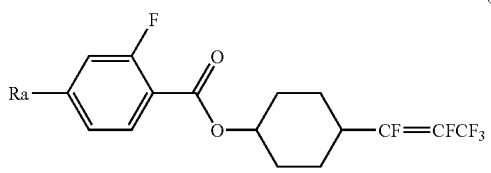
(1-ab-15)
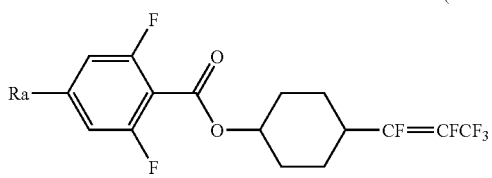

-continued
(1-ab-16)
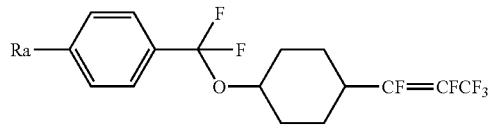
(1-ab-17)
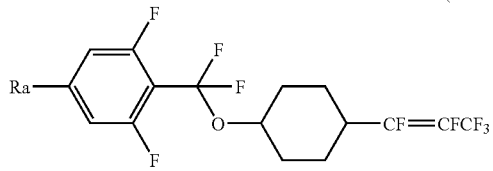
(1-ab-18)
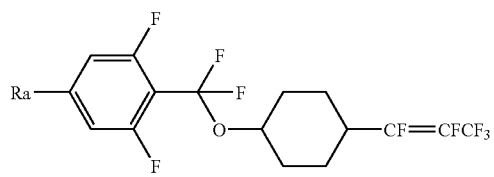
(1-ba-1)
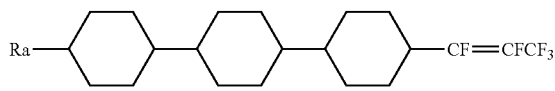
(1-ba-2)
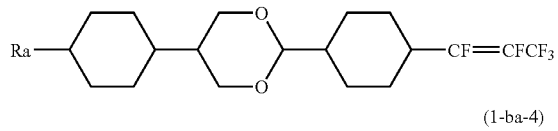
(1-ba-3)
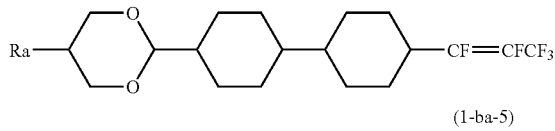
(1-ba-4)
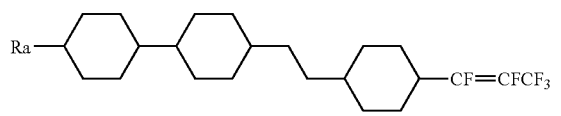
(1-ba-5)
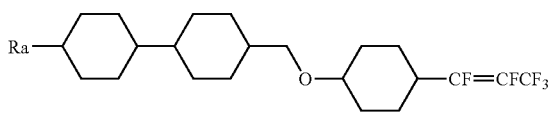
(1-ba-6)
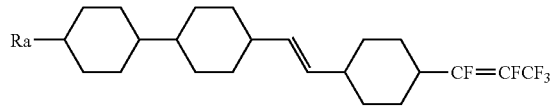
(1-ba-7)
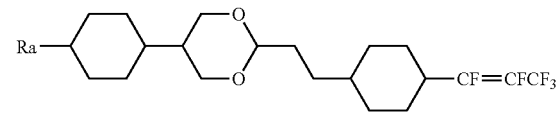
(1-ba-8)
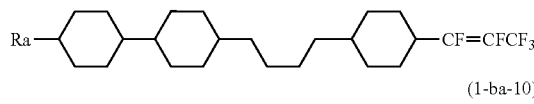
(1-ba-9)
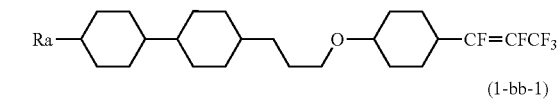
(1-ba-10)
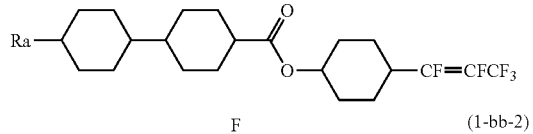
(1-bb-1)
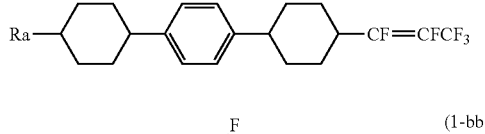
(1-bb-2)
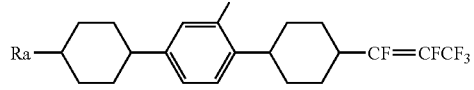
(1-bb-3)
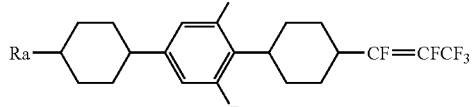
(1-bb-4)
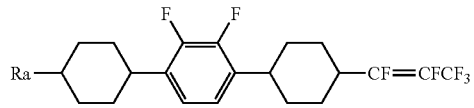
(1-bb-5)
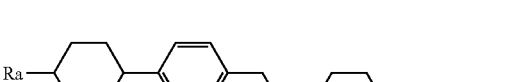
(1-bb-6)
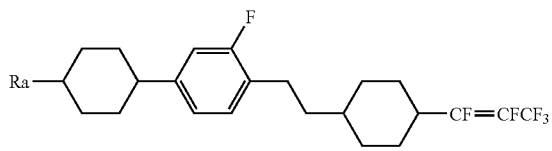
(1-bb-7)
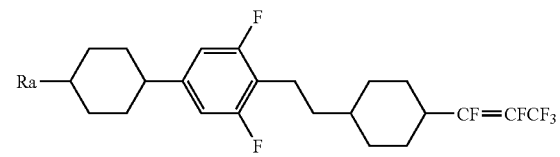

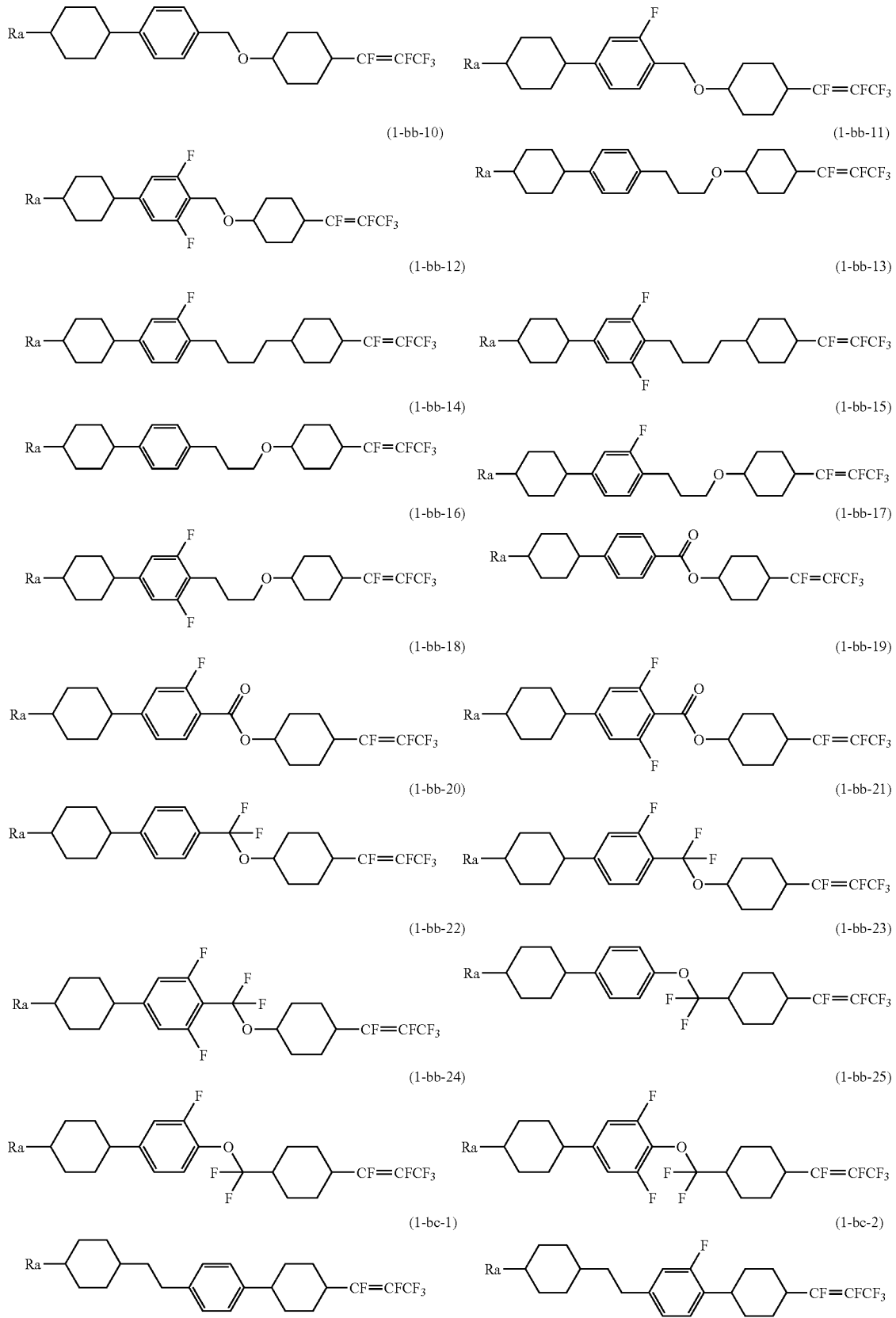

-continued
(1-bc-3)
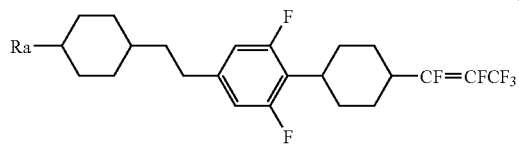
(1-bc-3)
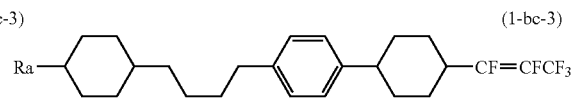
(1-bc-5)
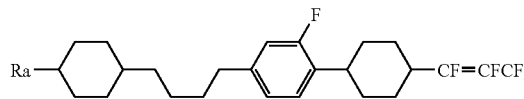
(1-bc-6)
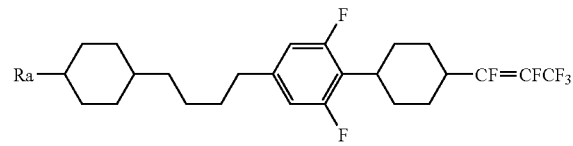
(1-bd-1)
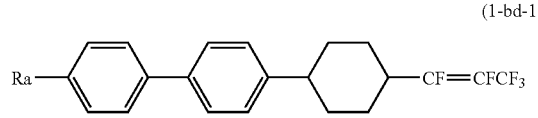
(1-bd-2)
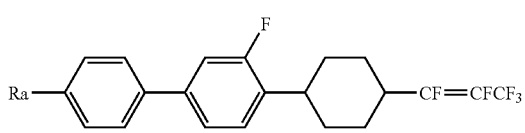
(1-bd-3)
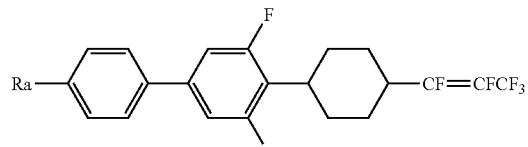
(1-bd-4)
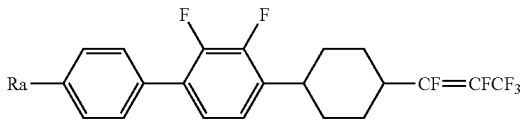
(1-bd-5)
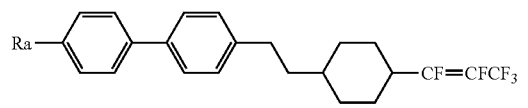
(1-bd-6)
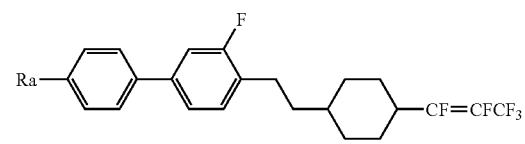
(1-bd-7)
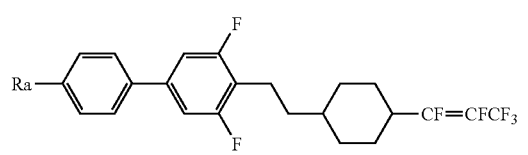
(1-bd-8)
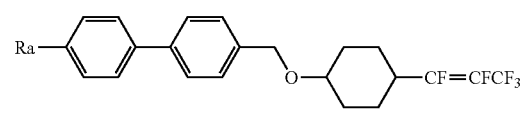
(1-bd-9)
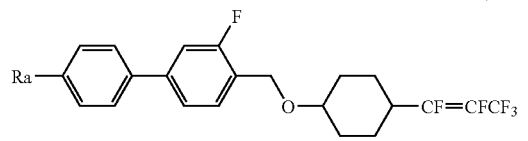
(1-bd-10)
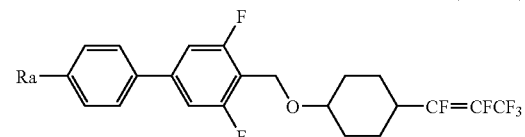
(1-bd-11)
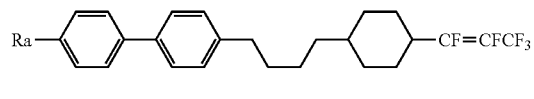
(1-bd-12)
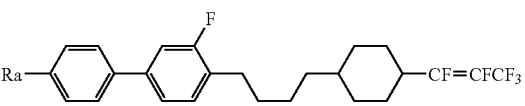
(1-bd-13)
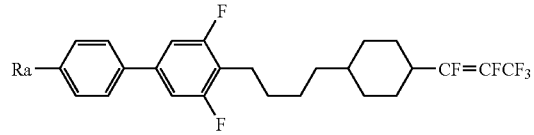
(1-bd-14)
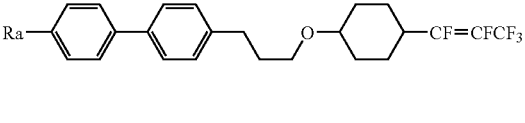
(1-bd-15)
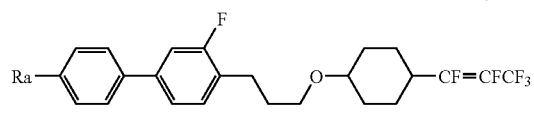
(1-bd-16)
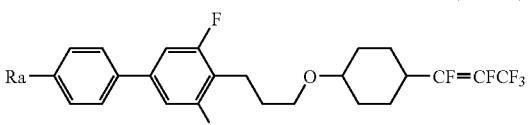

-continued
(1-bd-17)
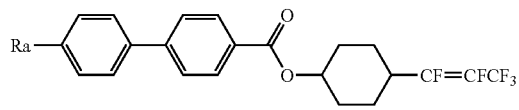
(1-bd-18)
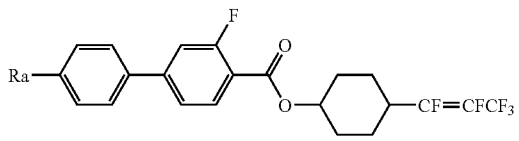
(1-bd-19)
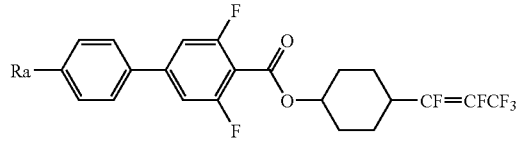
(1-bd-20)
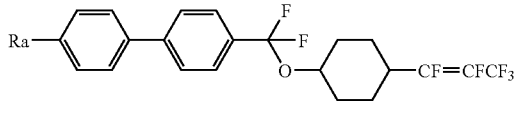
(1-bd-21)
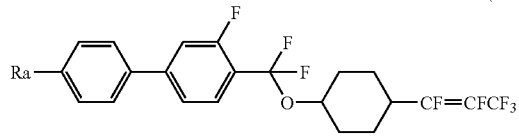
(1-bd-22)
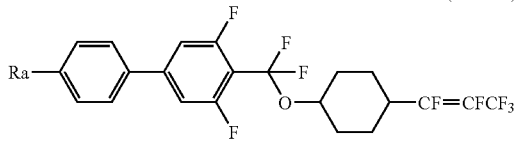
(1-bd-23)
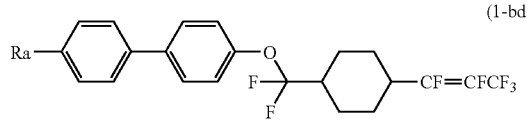
(1-bd-24)
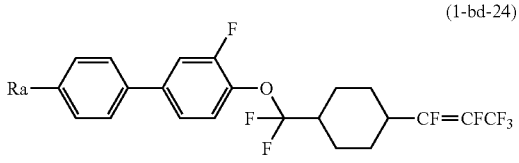
(1-bd-25)
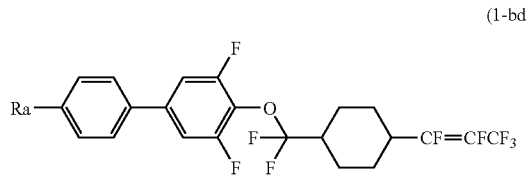
(1-be-1)
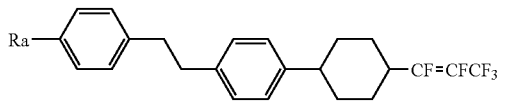
(1-be-2)
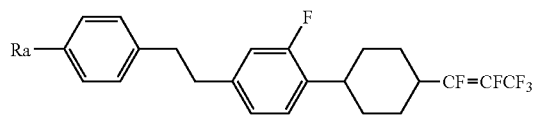
(1-be-3)
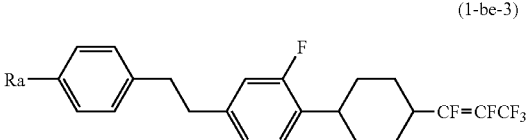
(1-be-4)
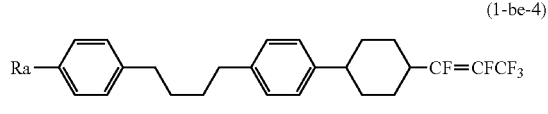
(1-be-5)
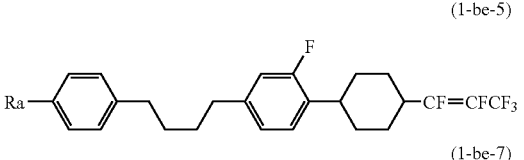
(1-be-6)
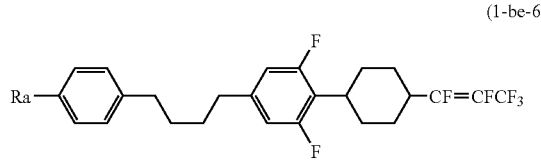
(1-be-7)
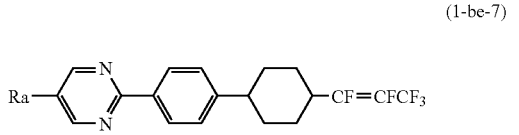
(1-be-8)
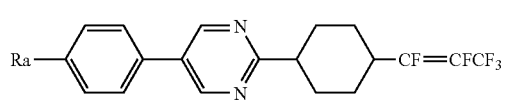
(1-bf-1)
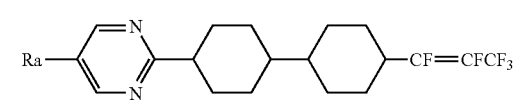
(1-bf-2)
(1-ca-1)
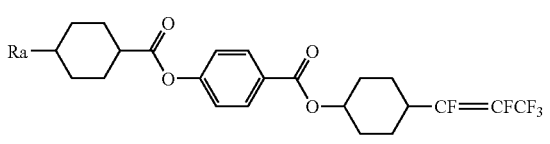

-continued
(1-ca-2)
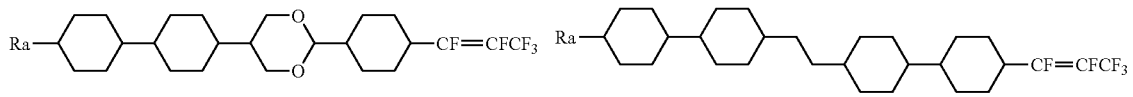
(1-ca-3)
(1-ca-4)
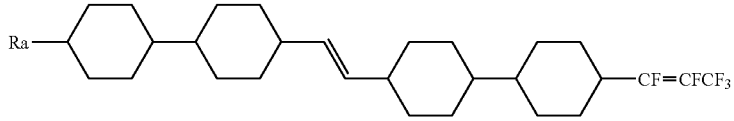
(1-ca-5)
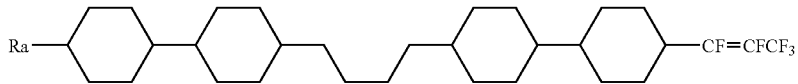
(1-ca-6)
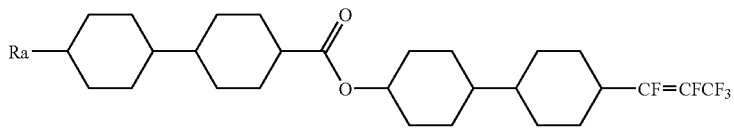
(1-ca-7)
(1-cb-1)
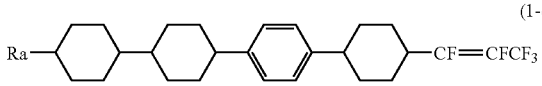
(1-cb-2)
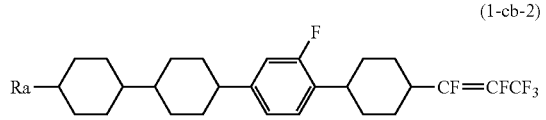
(1-cb-3)
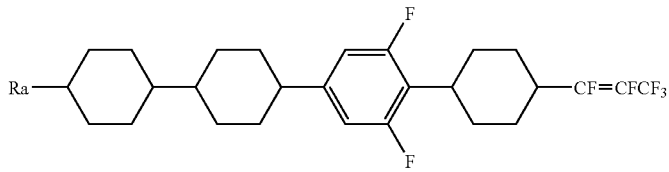
(1-cb-4)
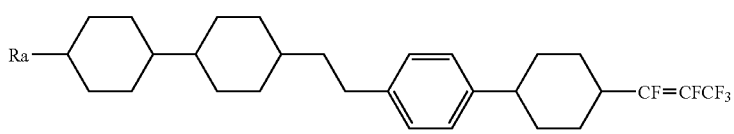
(1-cb-5)
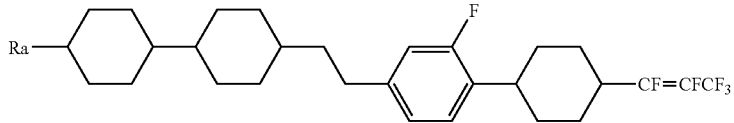
(1-cb-6)
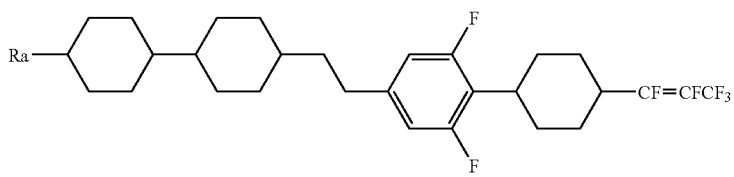
(1-cb-7)
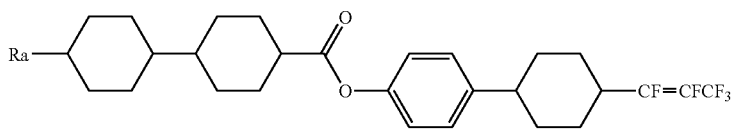

-continued
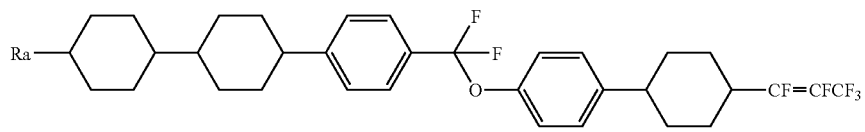 (1-cb-8)
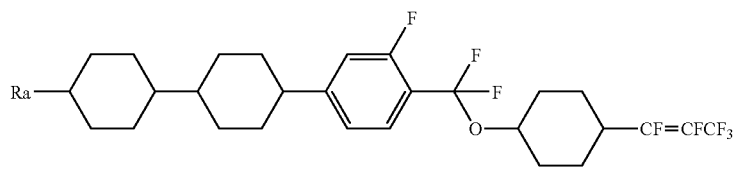 (1-cb-9)
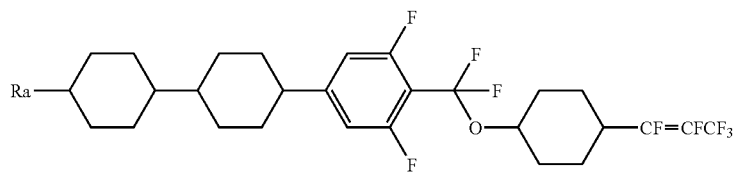 (1-cb-10)
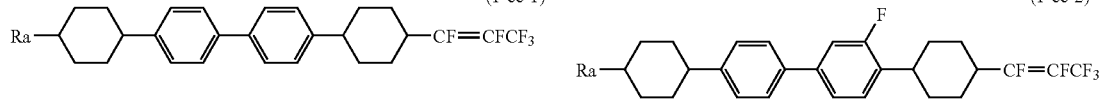
(1-cc-1) (1-cc-2)
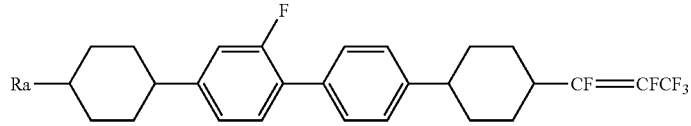 (1-cc-3)
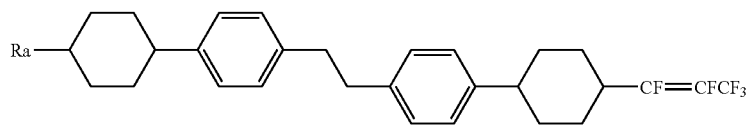 (1-cc-4)
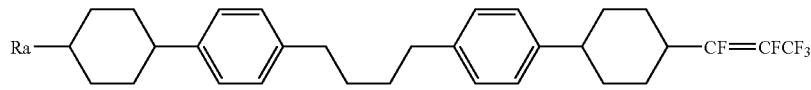 (1-cc-5)
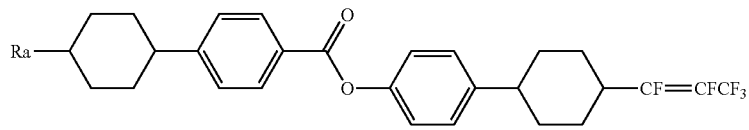 (1-cc-6)
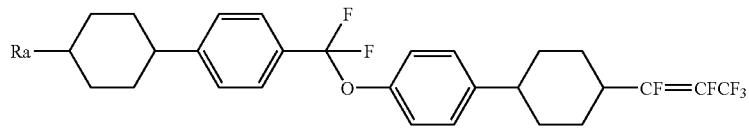 (1-cc-7)
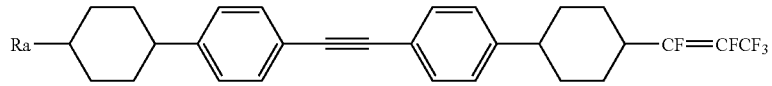 (1-cc-8)

The compound (1) is able to be synthesized by combining the means of organic synthetic chemistry. Methods for the introduction of aimed end group, ring and bonding group are mentioned in reference books such as "Organic Syntheses" (John Wiley & Sons, Inc.), "Organic Reactions" (John Wiley & Sons, Inc.), "Comprehensive Organic Synthesis" (Pergamon Press) and "Shin Jikkenn Kagaku Koza" (New Experimental Chemistry) (Maruzen).

An example for the introduction of perfluoropropenyl into a cyclohexane ring is as follows.

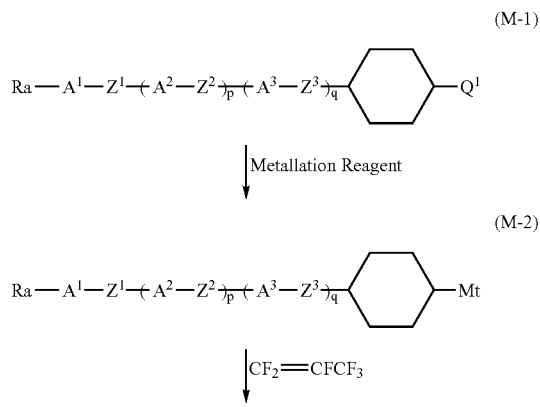

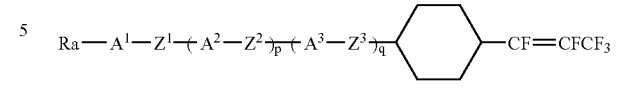

In the above scheme, meanings of the symbols Ra, $A^1$, $A^2$, $A^3$, $Z^1$, $Z^2$, $Z^3$, p and q are the same as those of the symbols in item 1 for the embodiments of the present invention. $Q^1$ is halogen and Mt is Li, K, MgBr, MgCl, ZnBr or ZnCl. When the compound (I-1) is made to react with a single substance of metal such as lithium and magnesium or an organometallic reagent such as alkyl lithium, alkyl zinc, alkyl potassium and alkyl cadmium, an organometallic compound (M-2) is prepared. When 1,1,2,3,3,3-hexafluoropropene is made to react with the compound (M-2), a compound (1) is prepared in a good yield.

With regard to a method for the production of a bonding group $Z^1$, $Z^2$ or $Z^3$, a scheme will be firstly shown and then explanation will be made in the following items (I) to (XI). In the scheme, $MSG^1$ or $MSG^2$ is a monovalent organic group having a ring. Plural $MSG^1$ (or $MSG^2$) used in the scheme may be either same or different. The compounds (1A) to (1K) correspond to the compound (1).

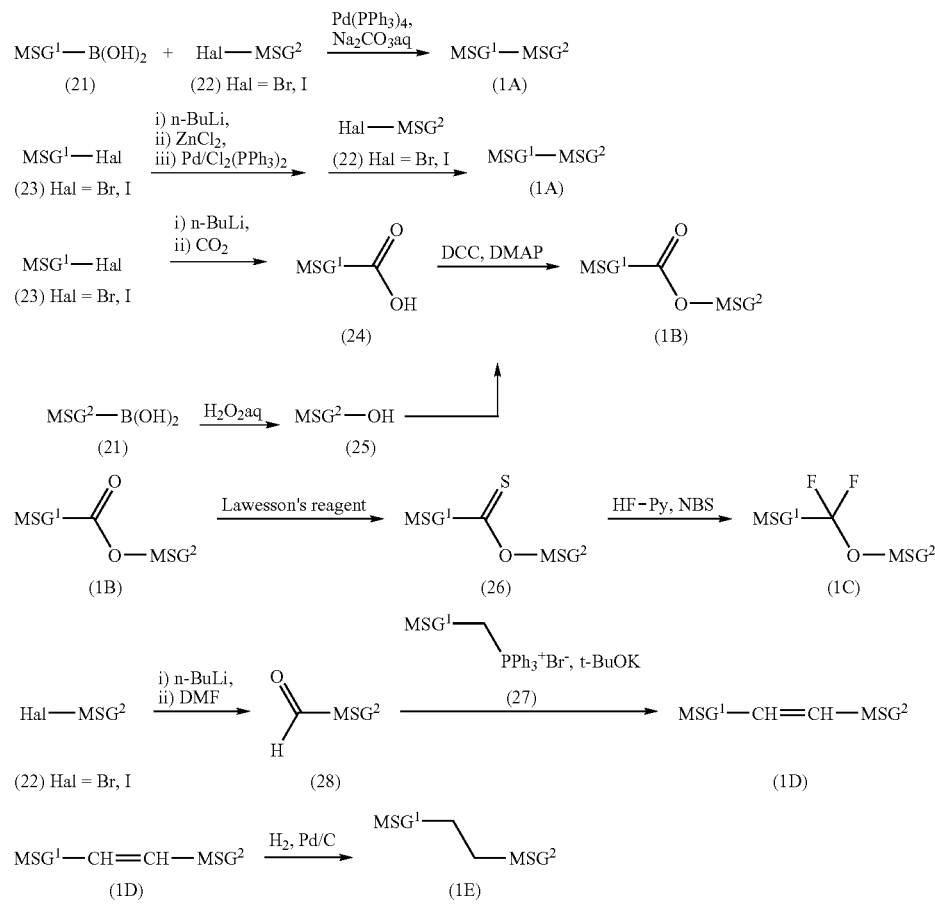

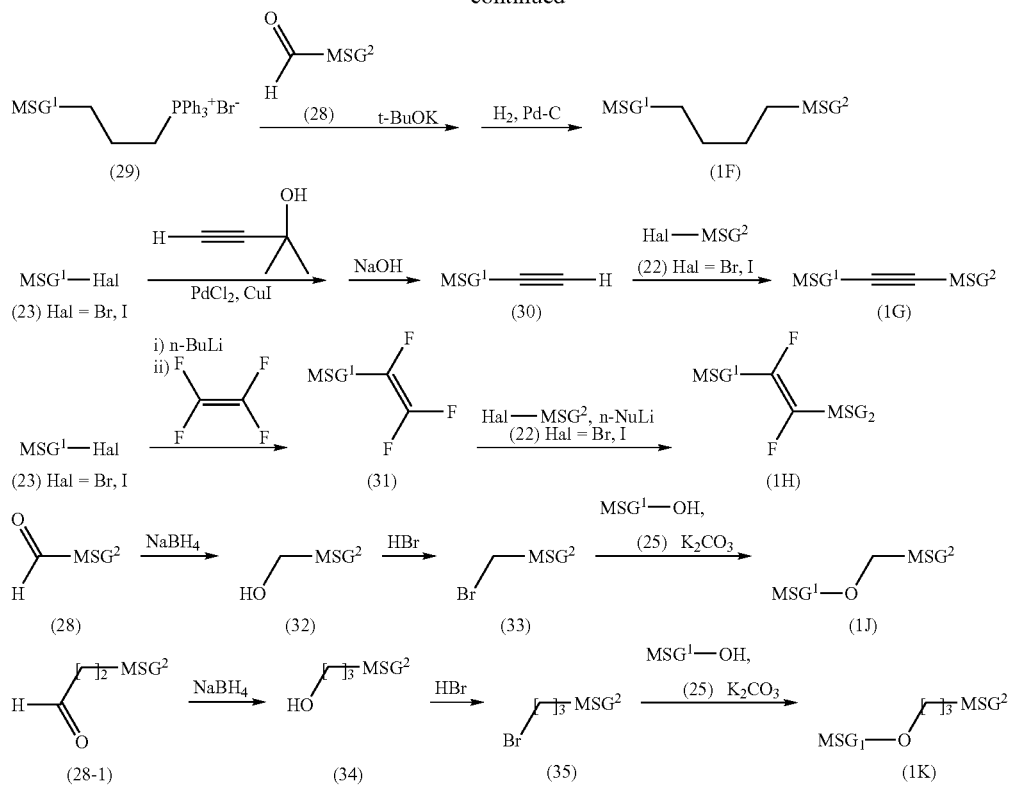

(I) Production of a Single Bond

Arylboric acid (21) is made to react with (22) which was synthesized by a known method in the presence of a catalyst such as an aqueous solution of carbonate and tetrakistriphenyl phosphine palladium to synthesize a compound (1A). It is also possible to synthesize this compound (1A) in such a manner that a compound (23) synthesized by a known method is made to react with n-butyl lithium and then successively made to react with a catalyst such as zinc chloride or dichlorobistriphenyl phosphine palladium and a compound (22).

(II) Production of —COO— and —OCO—

After the compound (23) is made to react with n-butyl lithium, it is made to react with carbon dioxide to give a carboxylic acid (24). This compound is dehydrated together with an alcohol (25) or a phenol (25) synthesized by a known method in the presence of 1,3-dicyclohexyl carbodiimide (DDC) and DMAP (4-dimethylaminopyridine) to synthesize a compound (1B) having —COO—. A compound having —OCO— is able to be synthesized by that method as well.

(III) Production of —CF$_2$O— and —OCF$_2$—

The compound (1B) is treated with a sulfurizing agent such as a Lawson reagent to give a compound (26). The compound (26) is fluorinated with a hydrogen fluoride-pyridine complex and an NBS (N-bromosuccinimide) to synthesize a compound (1C) having —CF$_2$O— (M. Kuroboshi, et al., *Chem. Lett.*, 827 (1992)). It is also possible to synthesize the compound (1C) by fluorination of the compound (26) with diethylamino sulfur trifluoride (William H. Bunnelle, et al., *J. Org. Chem.*, 55, 768 (1990)). A compound having —OCF$_2$— is able to be synthesized by this method as well.

(IV) Production of —CH=CH—

A compound (27) synthesized by a known method is treated with a base such as potassium tert-butoxide to generate phosphorus ylide. In the meanwhile, the compound (22) is treated with n-butyl lithium and then made to react with a formamide such as N,N-dimethylformamide to give an aldehyde (28). This is made to react with phosphorus ylide to synthesize a compound (1D). Since a cis substance is produced under some reaction conditions, it is isomerized by a known method to a trans substance if necessary.

(V) Production of —(CH$_2$)$_2$—

The compound (1D) is subjected to a catalytic hydrogenation in the presence of a catalyst such as palladium carbon to synthesize a compound (1E).

(VI) Production of —(CH$_2$)$_4$—

The method of (IV) was conducted using a compound (29) instead of the compound (27) to produce —CH=CH— followed by subjecting to a catalytic hydrogenation to synthesize a compound (1F).

(VII) Production of —C≡C—

In the presence of a catalyst comprising dichloropalladium and copper halide, the compound (23) is made to react with 2-methyl-3-butyn-2-ol and a deprotection was carried out under a basic condition to give a compound (30). In the presence of a catalyst comprising dichloropalladium and copper halide, the compound (30) is made to react with the compound (22) to synthesize a compound (1G).

(VIII) Production of —CF=CF—

After treating the compound (23) with n-butyl lithium, it is made to react with tetrafluoroethylene to give a compound (31). The compound (22) treated with n-butyl lithium is made to react with the compound (31) to synthesize a compound (1H).

(IX) Production of —CH$_2$O— or —OCH$_2$—

The compound (28) is reduced with a reducing agent such as sodium borohydride to give a compound (32). This is halogenated with hydrogen bromide or the like to give a compound (33). The compound (33) is made to react with the compound (25) in the presence of potassium carbonate or the like to synthesize a compound (1I).

(X) Production of —(CH$_2$)$_3$O— or —O(CH$_2$)$_3$—

The method of (IX) was carried out using a compound (34) instead of the compound (32) to synthesize a compound (1K).

(XI) Production of —(CF$_2$)$_2$—

Diketone (—COCO—) is fluorinated with sulfur tetrafluoride in the presence of a hydrogen fluoride catalyst according to *J. Am. Chem. Soc.*, 2001, 123, 5414 to give a compound having —(CF$_2$)$_2$—.

Secondly, the composition of the present invention will be further illustrated. The composition containing the compound (1) has characteristics such as broad temperature range for nematic phase, low viscosity, appropriate optical anisotropy and low threshold voltage. The compound (1) shows various physical properties depending upon its chemical structure. The dielectric anisotropy of this compound is relatively big to positive and big or nearly zero (small) to negative. A composition is prepared by selecting the compound (1) together with taking the physical property such as dielectric anisotropy and type of mode of element into consideration.

Amount (percentage) of the compound mentioned below is in terms of % by weight on the basis of the total weight of the composition. The composition may comprise only plural compound selected from the compound (1). A preferred composition contains at least one compound selected from the compound (1) in an amount of 1 to 99%. The composition may also contain at least one compound selected from the group consisting of the compounds (2), (3) and (4), at least one compound selected from the group consisting of the compounds (5) and (6) or at least one compound selected from the group consisting of the compounds (7), (8) and (9). For an object of adjustment of threshold voltage, temperature range for liquid crystal phase, optical anisotropy, dielectric anisotropy or viscosity, at least one compound selected from the group consisting of the compounds (10), (11) and (12) may be further added to the composition. Other compounds may also be added thereto for an object of adjusting the physical property of the resulting composition.

In the compounds (2), (3) and (4), dielectric anisotropy is big in positive and both thermal stability and chemical stability are excellent and, therefore, they are mostly used for a composition for a TN-TFT mode. In the composition, the amount of such compounds is 1 to 99%. Preferably, it is 10 to 97% and, more preferably, it is 15 to 95%. The compounds (10), (11) or (12) may be further added to the composition in order to adjust temperature range of liquid crystal phase, optical anisotropy, dielectric anisotropy, viscosity or threshold voltage.

In the compounds (5) and (6), dielectric anisotropy is very big in positive and, therefore, they are mostly used in a composition for STN and TN modes. Those compounds are used for an object of making the temperature range of liquid crystal phase of the composition broad, adjusting the optical anisotropy and the viscosity, lowering the threshold voltage, improving the sudden change in threshold voltage and so forth. In the composition for an STN or TN mode, amount of the compound (5) or (6) is within a range of 1 to 99%. Preferably, it is 10 to 80% and, more preferably, it is 15 to 60%. The compound (10), (11) or (12) may be further added to the composition in order to adjust temperature range of liquid crystal phase, viscosity, optical anisotropy, dielectric anisotropy or threshold voltage.

Since the compounds (7), (8) and (9) have negative dielectric anisotropy, they are mostly used for a composition for a VA mode. The compound (7) is used for an object of adjustment of viscosity, optical anisotropy, threshold voltage and so forth. The compound (8) is used for an object of making the clear point high, making the optical anisotropy big, making the threshold voltage low and so forth. When amount of such a compound is increased, threshold voltage of the composition becomes low while viscosity becomes high. Accordingly, in order to make the threshold voltage low, the small amount is preferred. In those compounds, dielectric anisotropy is negative and its absolute value is not more than 5 and, therefore, its amount is preferably not less than 40%. More preferably, it is 40 to 80%. Those compounds may be added to a composition where dielectric anisotropy is positive with an object of adjustment of elastic constant and voltage transmission rate curve. The amount in that case is preferably not more than 30%.

Absolute value of dielectric anisotropy of the compounds (10), (11) and (12) is small. The compound (10) is mostly used with an object of adjustment of optical anisotropy and viscosity. The compounds (11) and (12) are used with an object that clear point is made high so as to make the temperature range for liquid crystal phase broad or that optical anisotropy is adjusted. When amount of the compound (10), (11) or (12) is increased, threshold voltage of the composition becomes high and viscosity becomes low. Accordingly, the compound may be used in a large amount within such an extent that the threshold voltage of the composition does not become too high. In a composition for a TN-TFT mode, amount of such a compound is preferably not more than 40% and, more preferably, not more than 35%. In a composition for an STN or TN mode, amount of such a compound is preferably not more than 90% or, more preferably, not more than 80%.

Preferred compounds for the compounds (2) to (12) are compounds (2-1) to (2-9), compounds (3-1) to (3-97), compounds (4-1) to (4-33), compound (5-1) to (5-56), compounds (6-1) to (6-3), compounds (7-1) to (7-3), compounds (8-1) to (8-5), compounds (9-1) to (9-3), compounds (10-1) to (10-11), compounds (11-1) to (11-18) and compounds (12-1) to (12-6), respectively. In those compounds, meanings of the symbols $R^1$, $R^2$, $R^3$, $R^4$, $R^5$, $R^6$, $R^7$, $X^1$ and $X^2$ are the same as those of the symbols mentioned in items 16 to 19 of embodiments of the present invention.

(2-1)

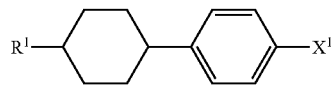

(2-1)

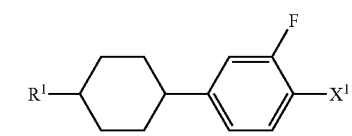

-continued
(2-3) 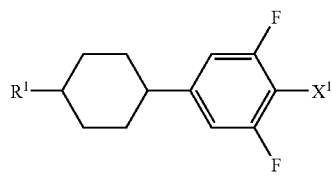
(2-4) 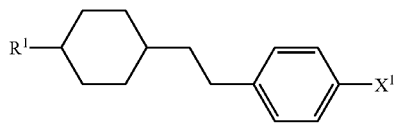
(2-5) 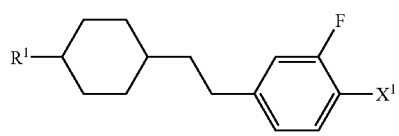
(2-6) 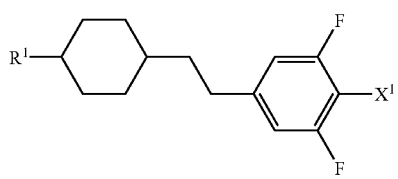
(2-7) 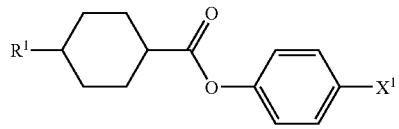
(2-8) 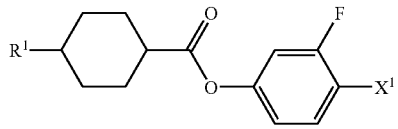
(2-9) 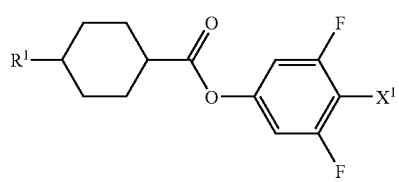
(3-1) 
(3-2) 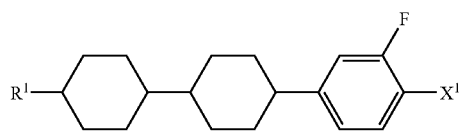
(3-3) 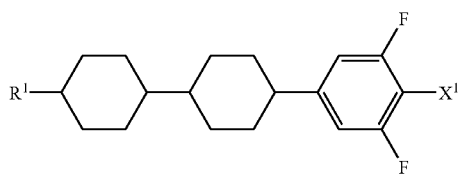
(3-4) 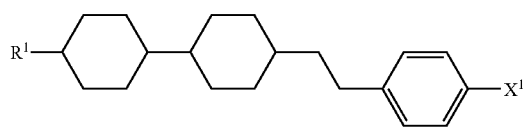
(3-5) 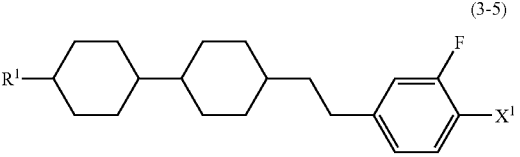
(3-6) 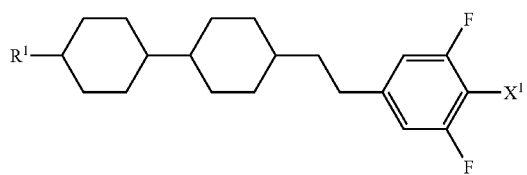
(3-7) 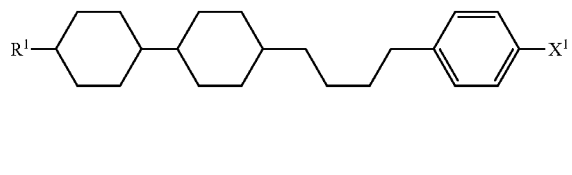

-continued
(3-8)
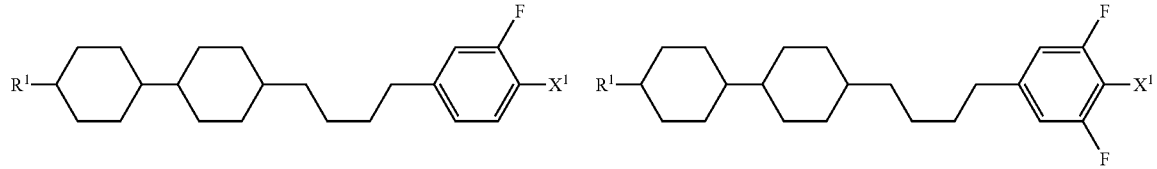
(3-9)
(3-9)
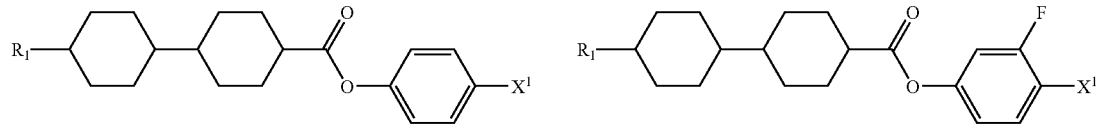
(3-10)
(3-12)
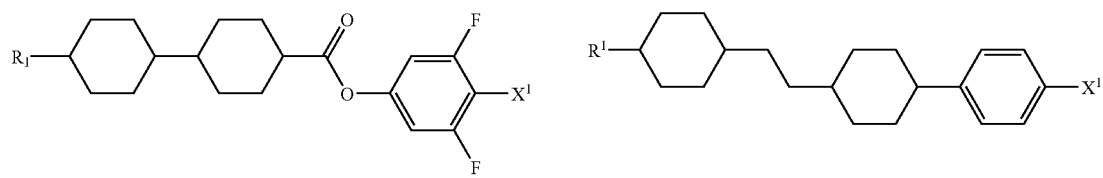
(3-13)
(3-14)
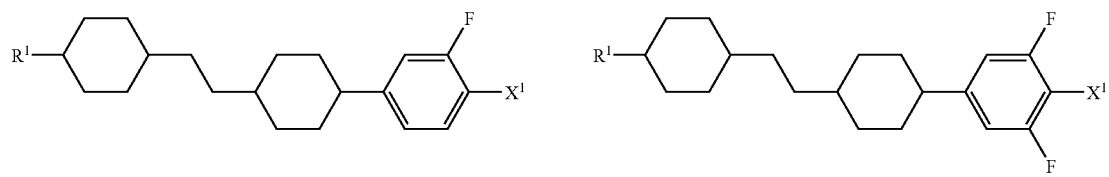
(3-15)
(3-16)
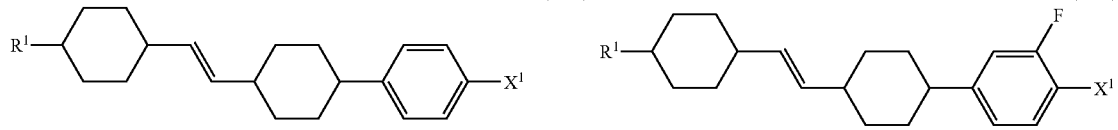
(3-17)
(3-18)
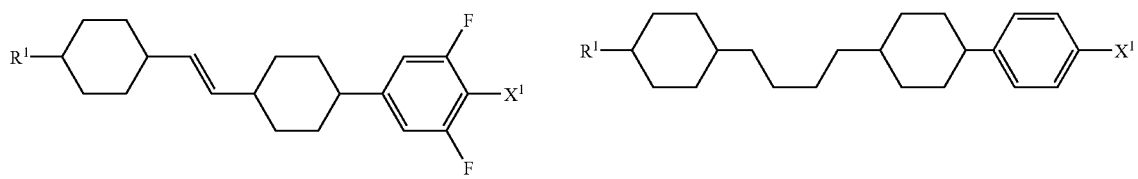
(3-19)
(3-20)
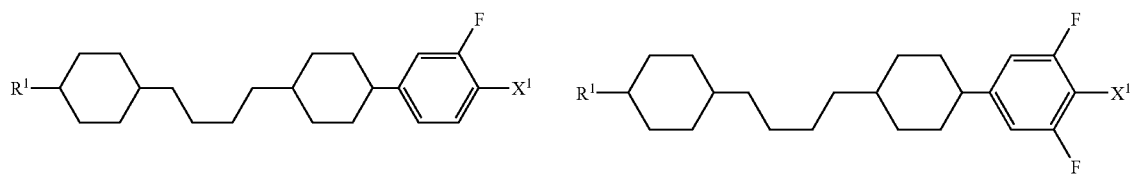
(3-21)

-continued
(3-22)
(3-23)
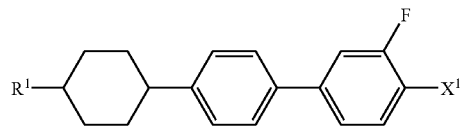
(3-24)
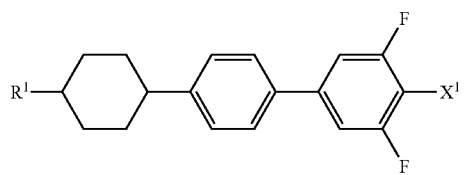
(3-25)
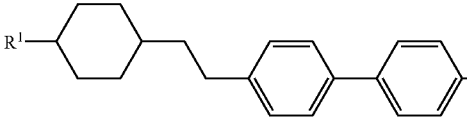
(3-26)
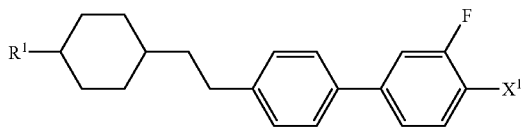
(3-27)
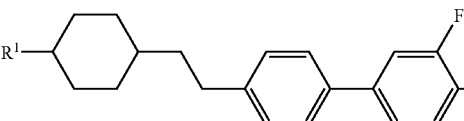
(3-28)
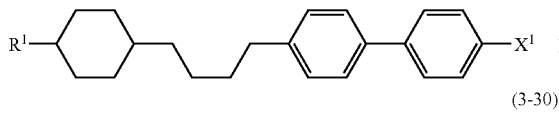
(3-29)
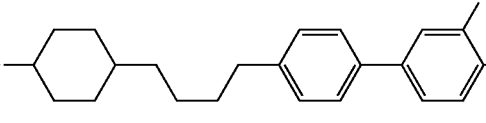
(3-30)
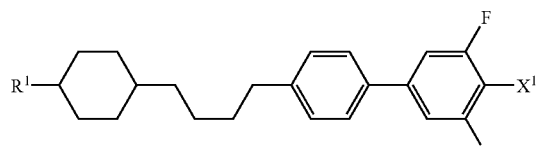
(3-31)
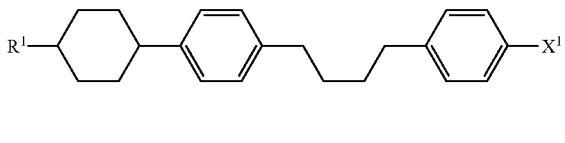
(3-32)
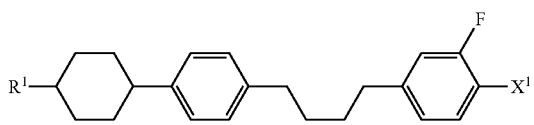
(3-33)
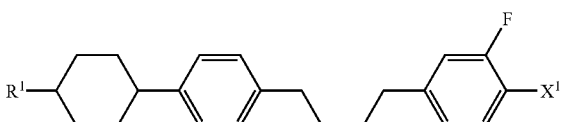
(3-34)
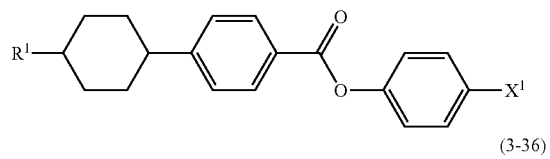
(3-35)
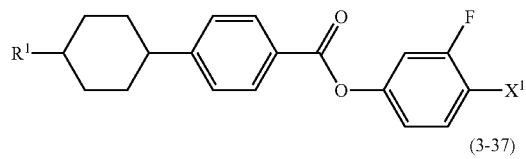
(3-36)
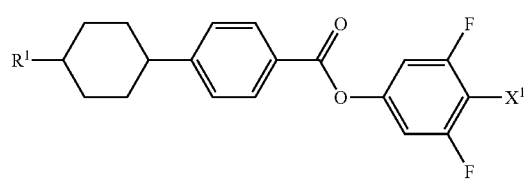
(3-37)
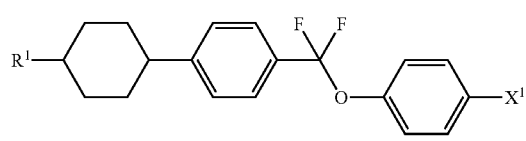

-continued
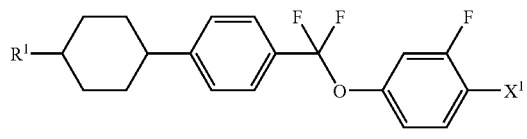
(3-38)
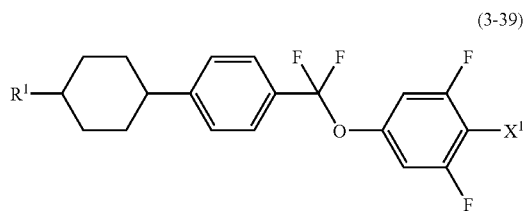
(3-39)
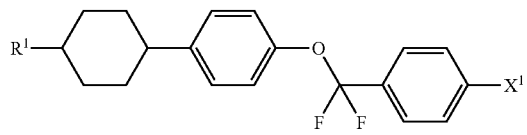
(3-40)
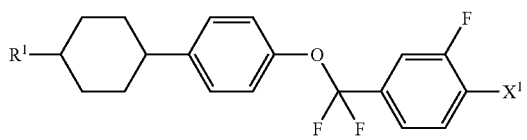
(3-41)
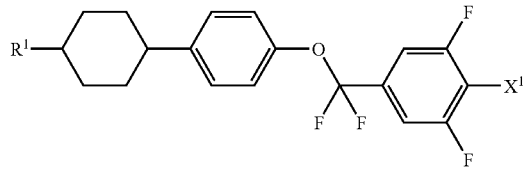
(3-42)
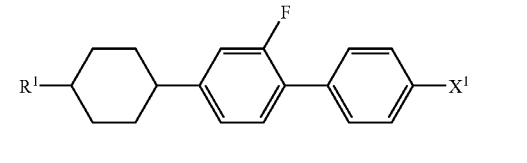
(3-43)
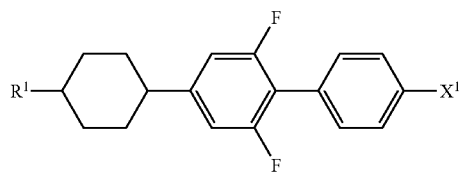
(3-44)
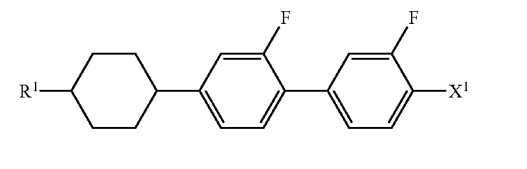
(3-45)
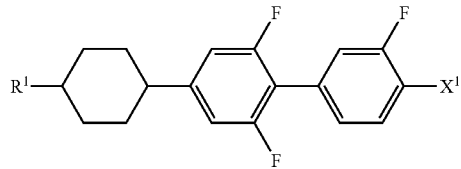
(3-46)
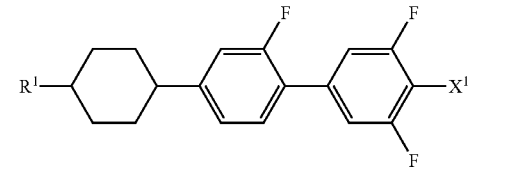
(3-47)
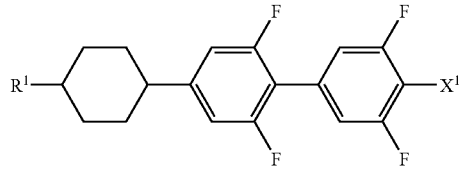
(3-48)
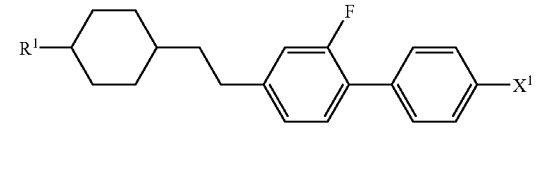
(3-49)
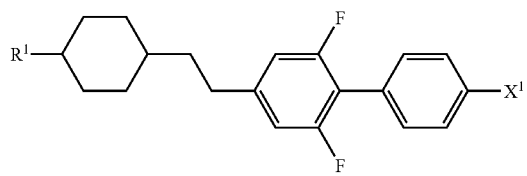
(3-50)
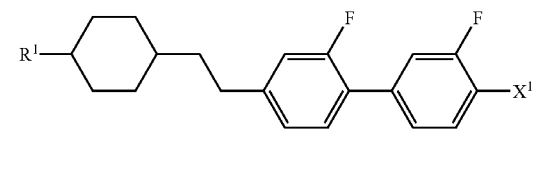
(3-51)

-continued
(3-52)
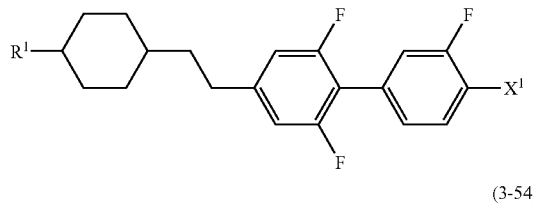
(3-53)
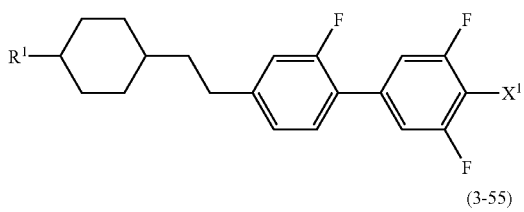
(3-54)
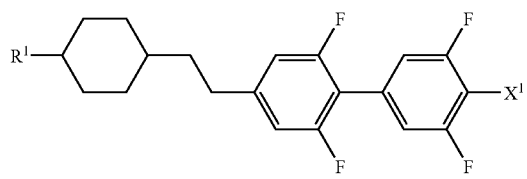
(3-55)
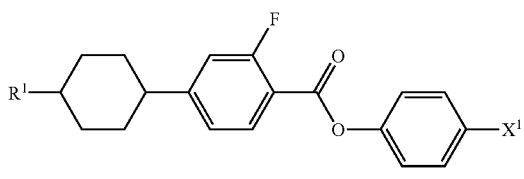
(3-56)
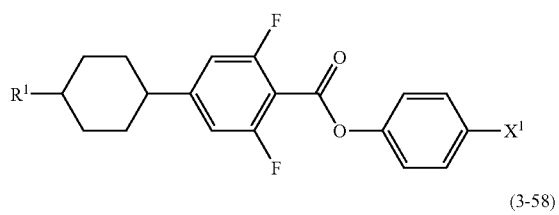
(3-57)
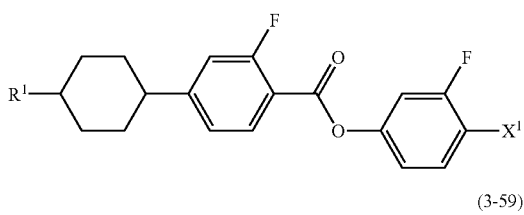
(3-58)
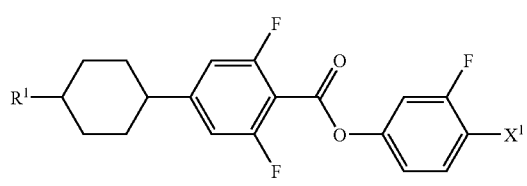
(3-59)
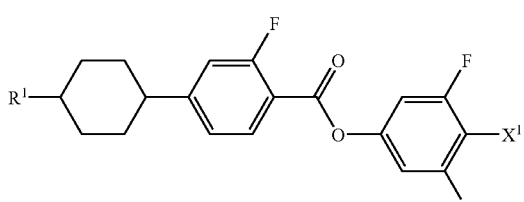
(3-60)
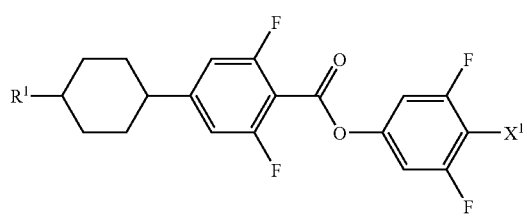
(3-61)
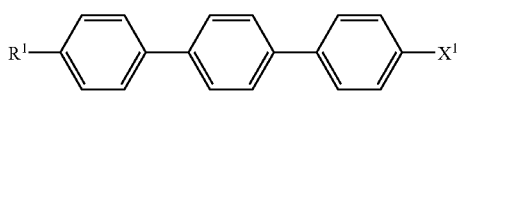
(3-62)
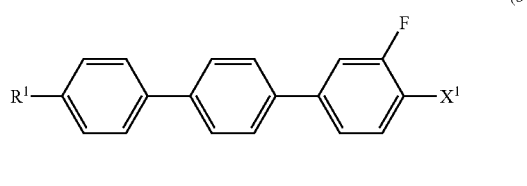
(3-63)
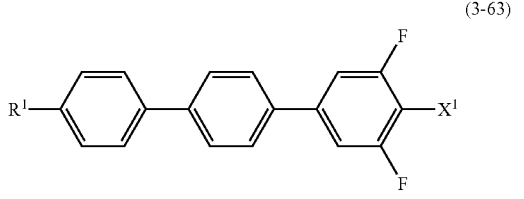
(3-64)
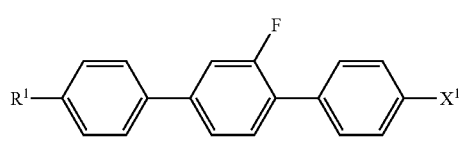
(3-65)
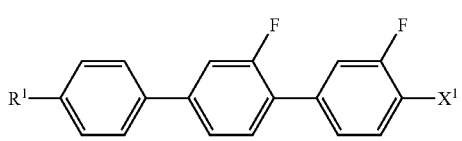

-continued
(3-66)
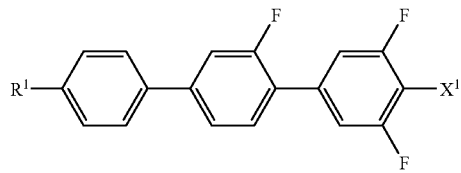
(3-67)
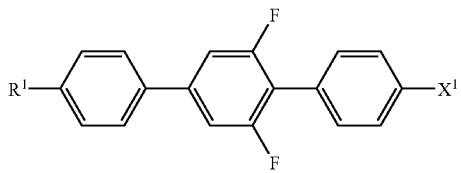
(3-68)
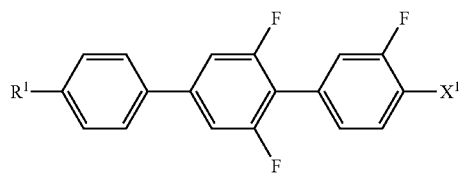
(3-69)
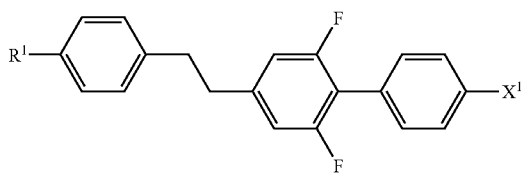
(3-70)
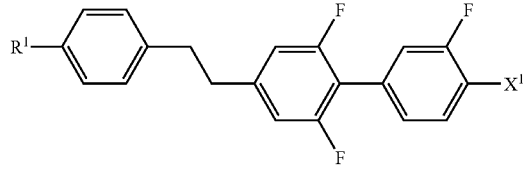
(3-71)
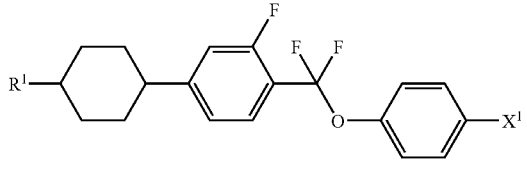
(3-72)
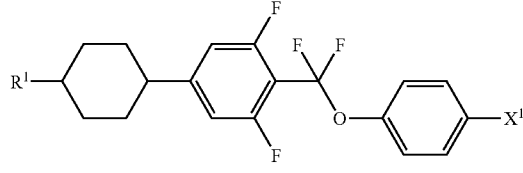
(3-73)
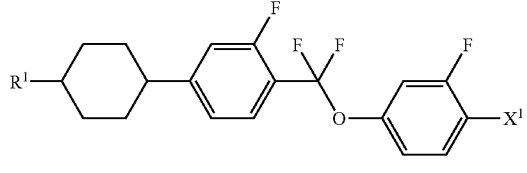
(3-74)
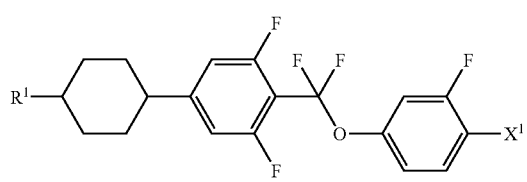
(3-75)
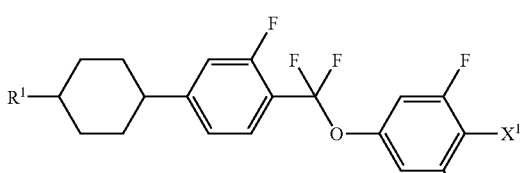
(3-76)
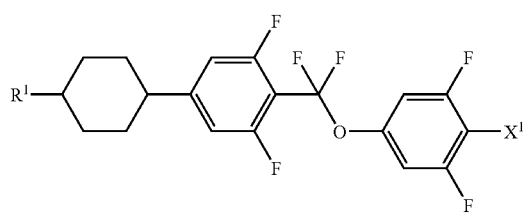
(3-77)
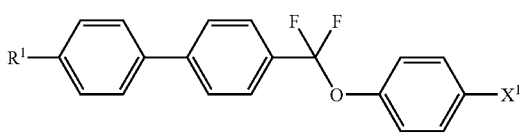
(3-78)
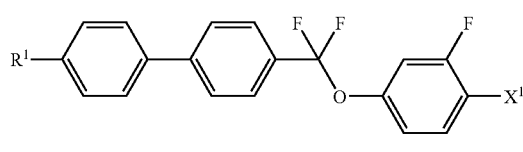
(3-79)
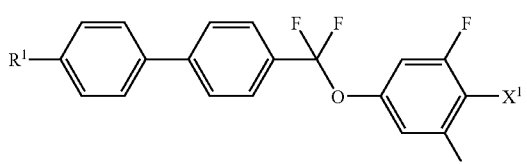

-continued
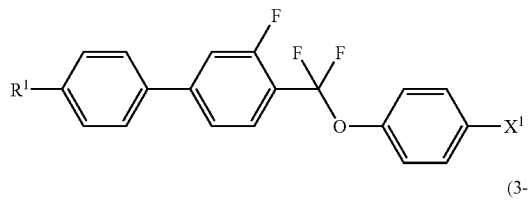 (3-80)
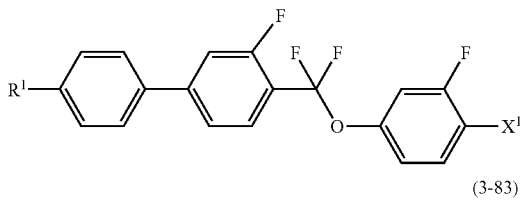 (3-81)
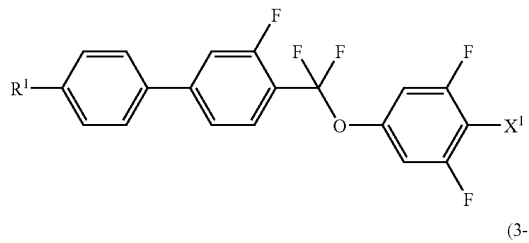 (3-82)
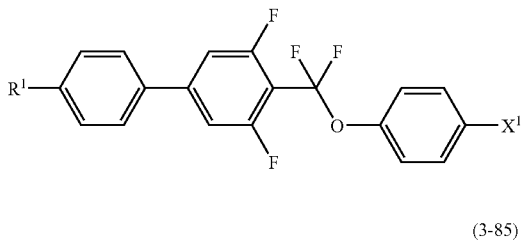 (3-83)
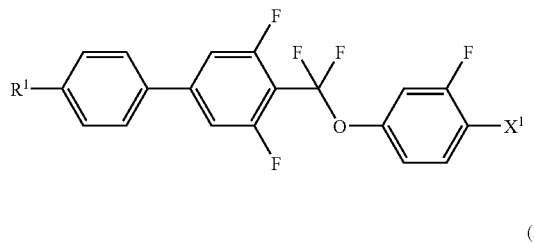 (3-84)
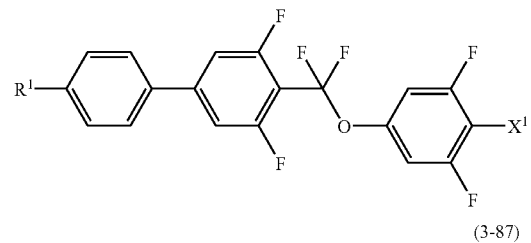 (3-85)
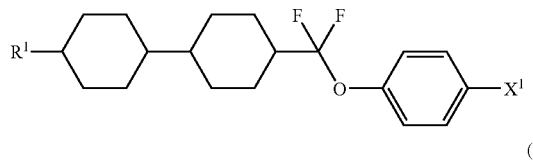 (3-86)
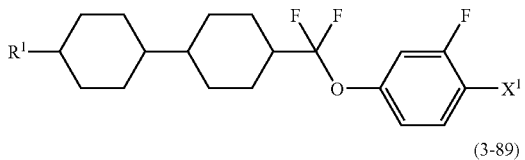 (3-87)
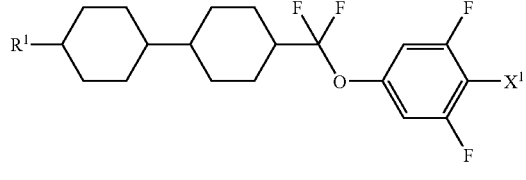 (3-88)
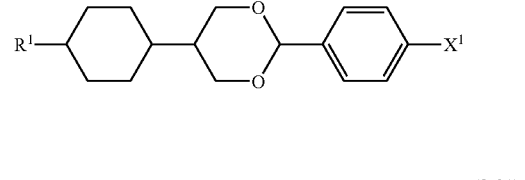 (3-89)
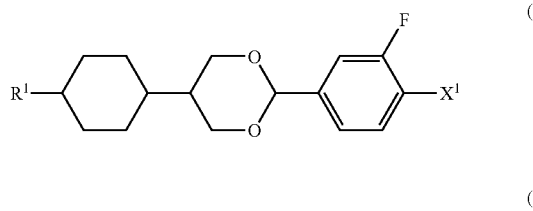 (3-90)
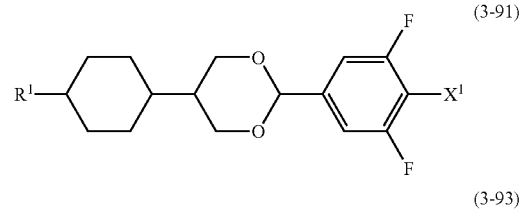 (3-91)
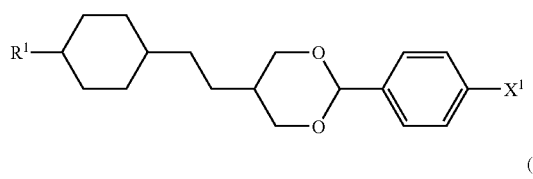 (3-92)
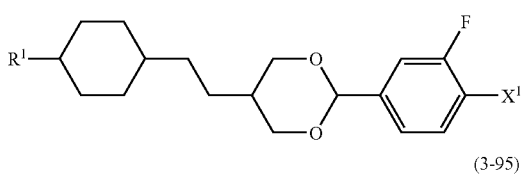 (3-93)
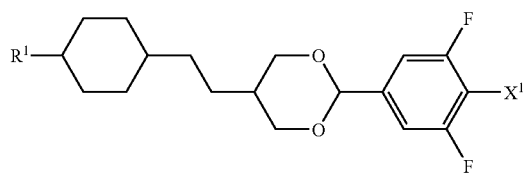 (3-94)
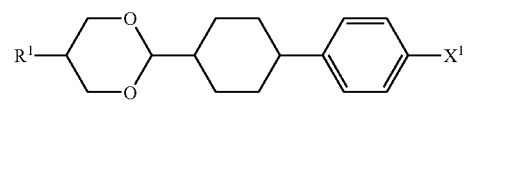 (3-95)

-continued
(3-96)
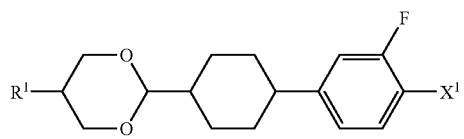
(3-96)
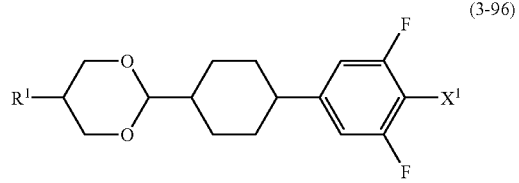
(4-1)
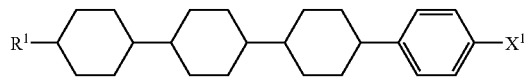
(4-2)
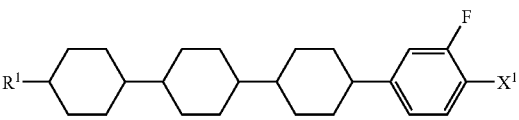
(4-3)
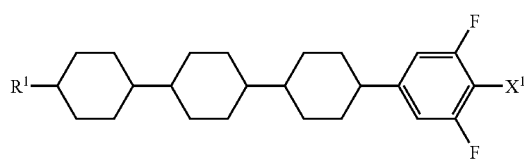
(4-4)
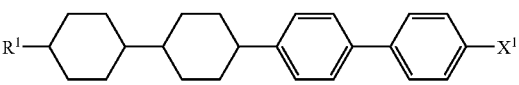
(4-5)
(4-6)
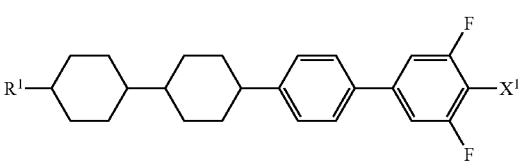
(4-7)
(4-8)
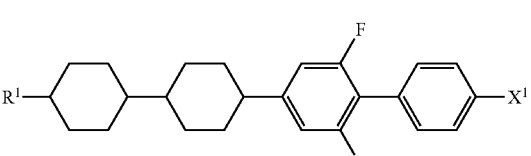
(4-9)
(4-10)
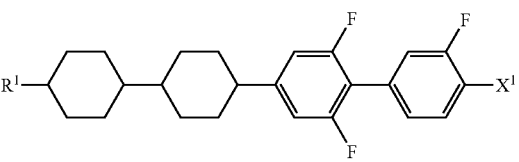
(4-11)
(4-12)
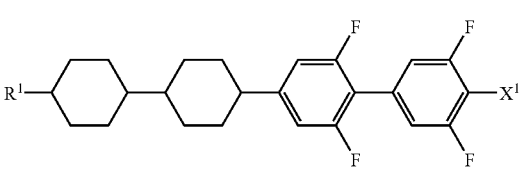
(4-13)
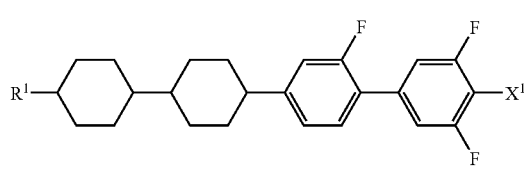
(4-14)
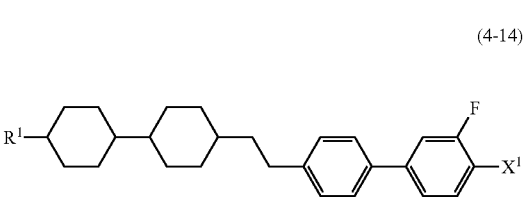

-continued
(4-15)
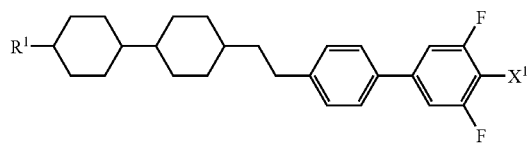
(4-16)
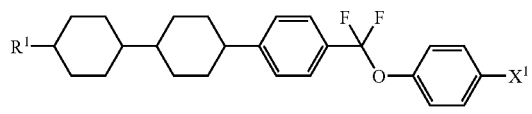
(4-17)
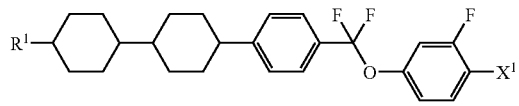
(4-18)
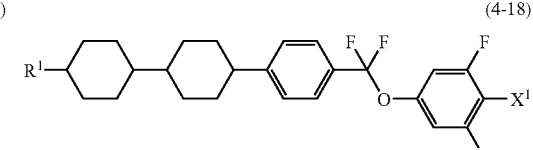
(4-19)
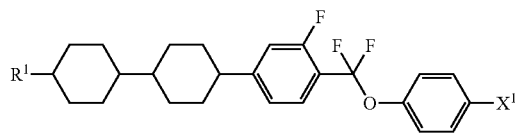
(4-20)
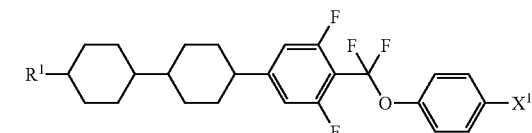
(4-21)
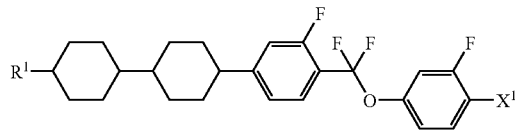
(4-22)
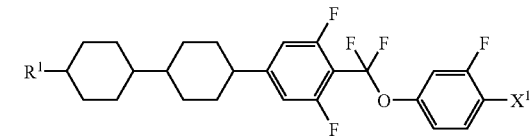
(4-23)
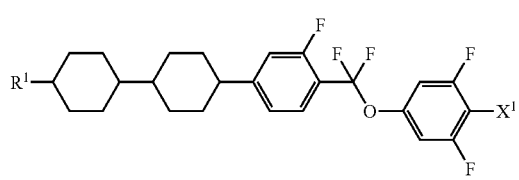
(4-24)
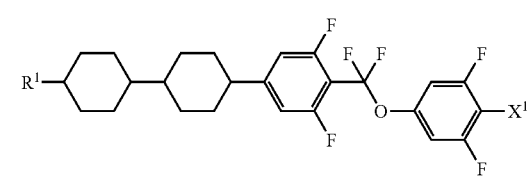
(4-25)
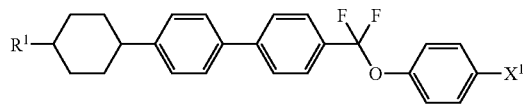
(4-26)
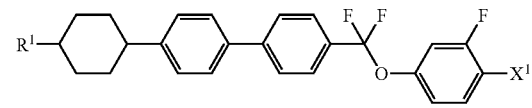
(4-27)
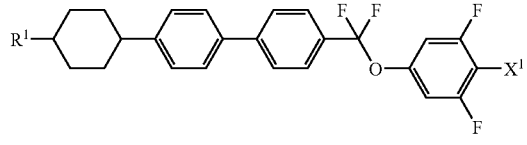
(4-28)
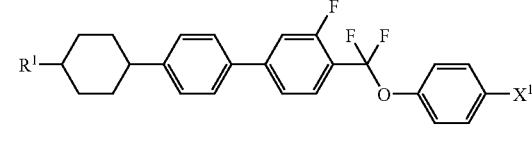
(4-29)
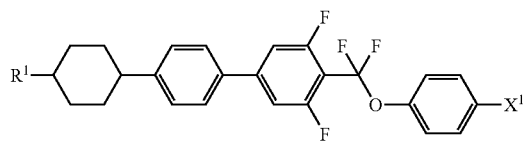
(4-30)
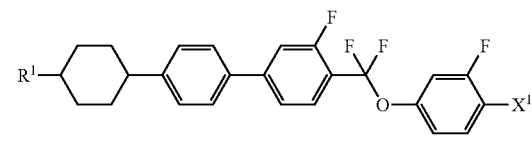
(4-31)
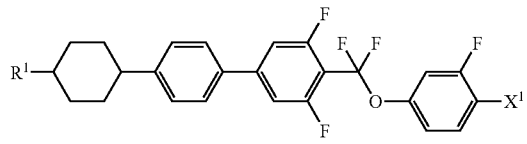

-continued
(4-33) 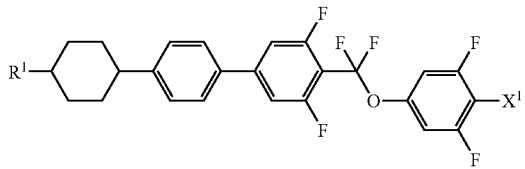
(5-1) 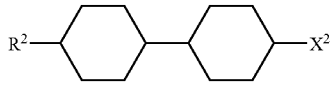
(5-2) 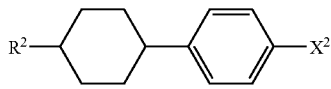
(5-3) 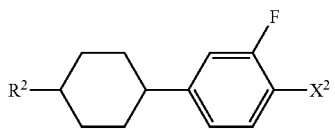
(5-4) 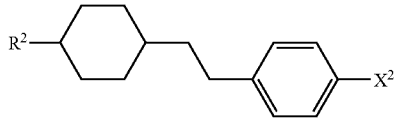
(5-5) 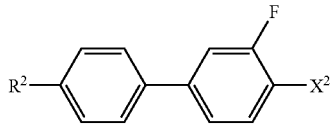
(5-6) 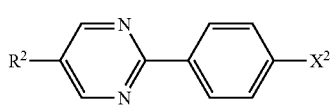
(5-7) 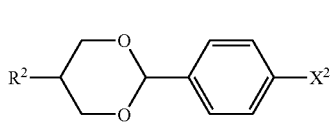
(5-8) 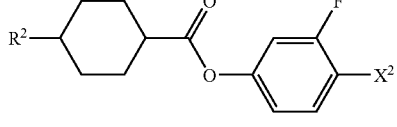
(5-9) 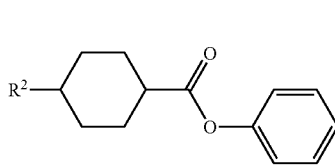
(5-10) 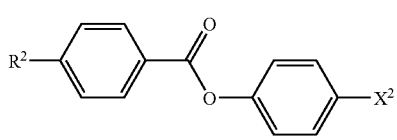
(5-11) 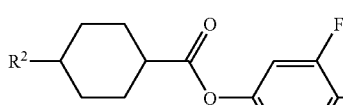
(5-12) 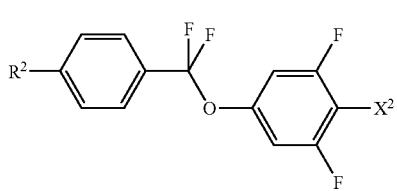
(5-13) 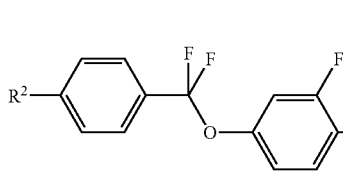
(5-14) 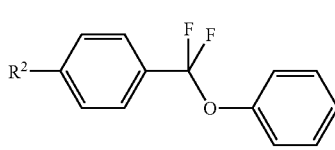
(5-15) 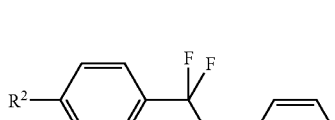
(5-16) 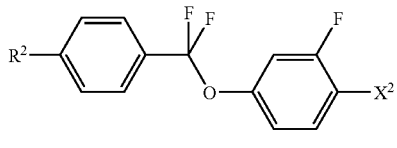
(5-17) 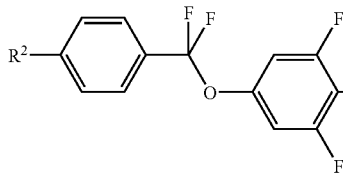

-continued
(5-18) 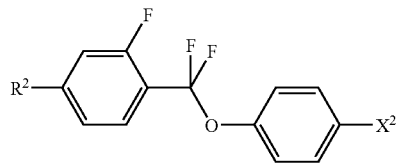
(5-19) 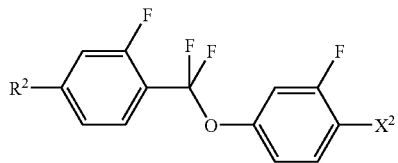
(5-20) 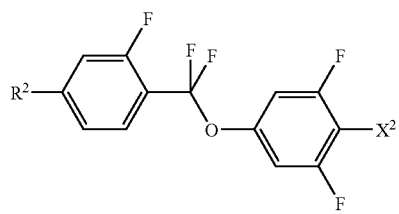
(5-21)
(5-22) 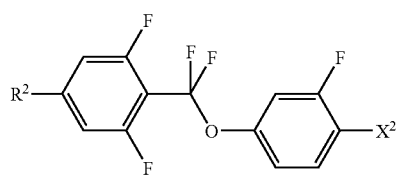
(5-23) 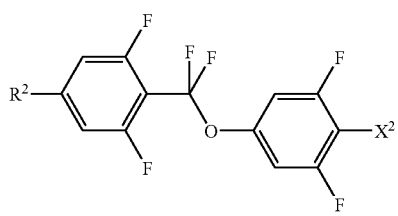
(5-24) 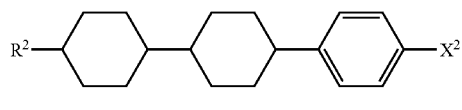
(5-25) 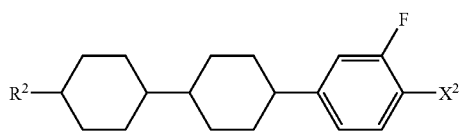
(5-26) 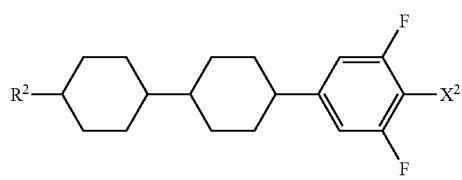
(5-27) 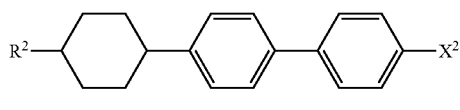
(5-28) 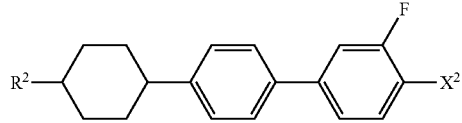
(5-29) 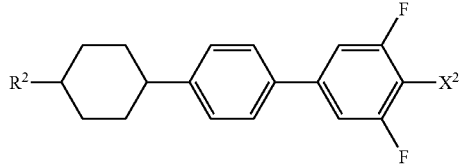
(5-30) 
(5-31) 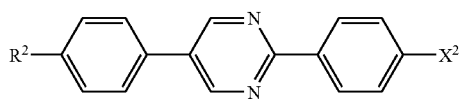
(5-32) 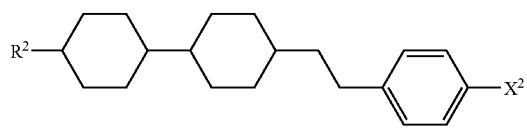
(5-33) 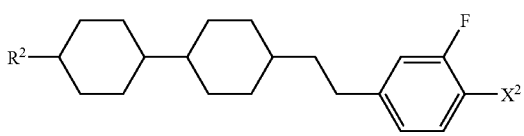

-continued
(5-34)
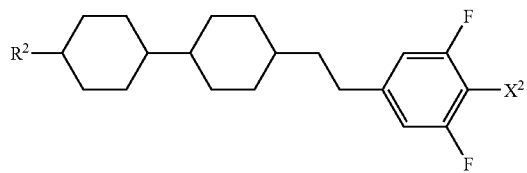
(5-35)
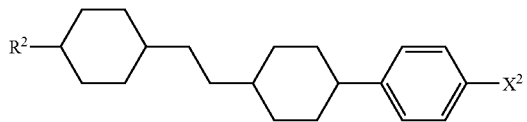
(5-36)
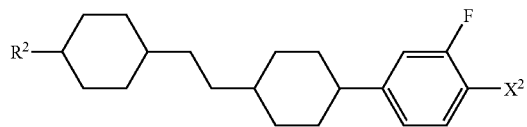
(5-37)
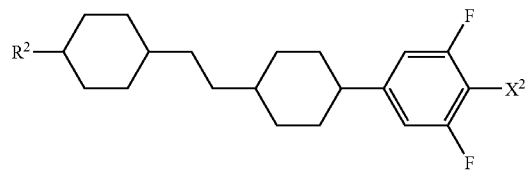
(5-38)
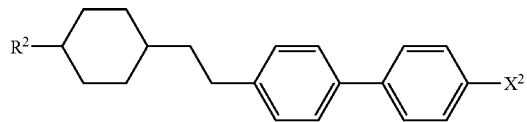
(5-39)
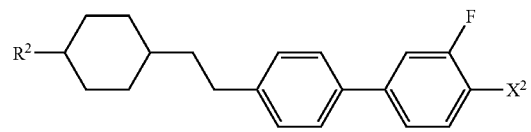
(5-40)
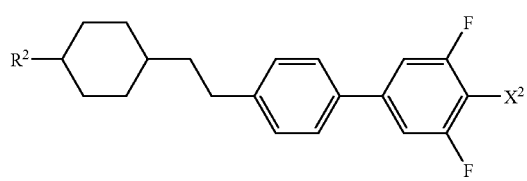
(5-41)
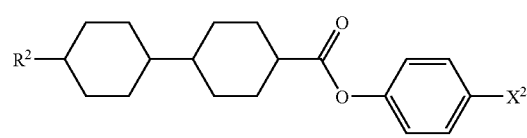
(5-42)
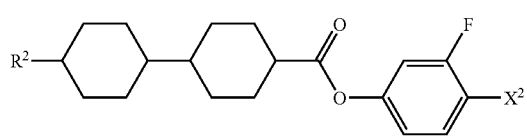
(5-43)
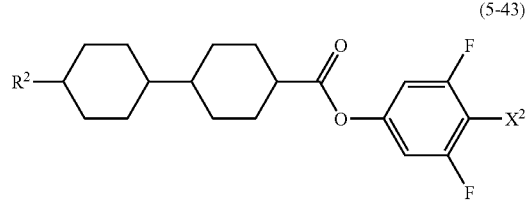
(5-44)
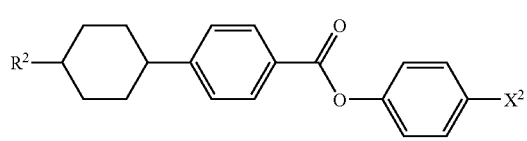
(5-45)
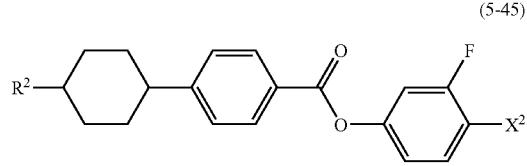
(5-46)
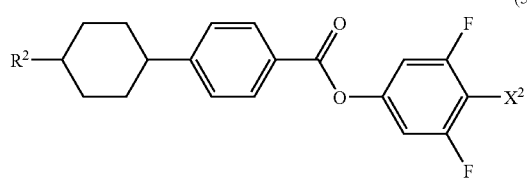
(5-47)
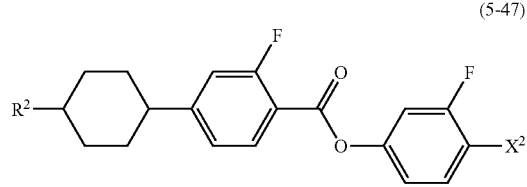
(5-48)
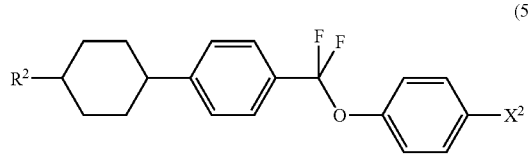
(5-49)

-continued
(5-50) 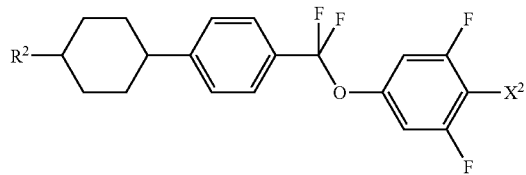
(5-51) 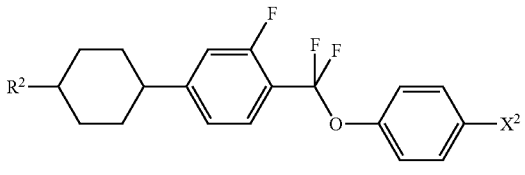
(5-52) 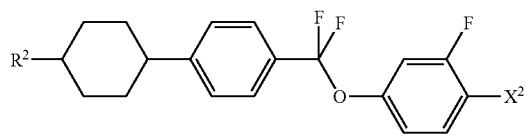
(5-53) 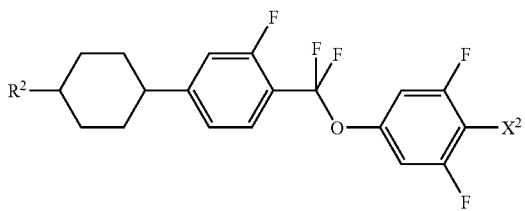
(5-54) 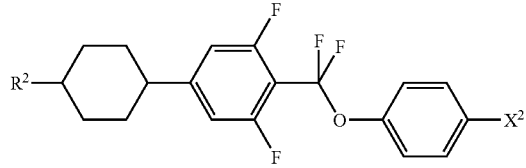
(5-55) 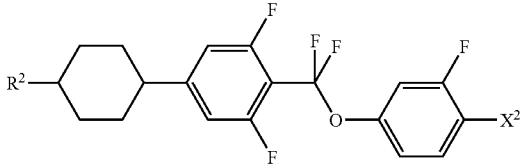
(5-56) 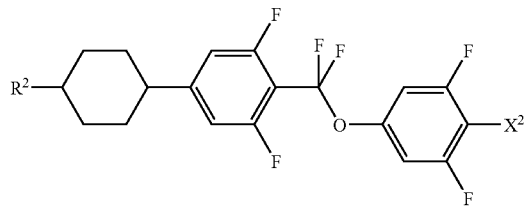
(6-1) 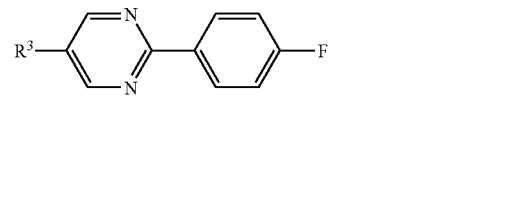
(6-2) 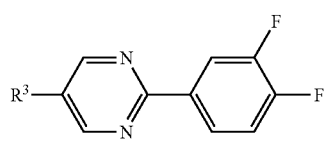
(6-3) 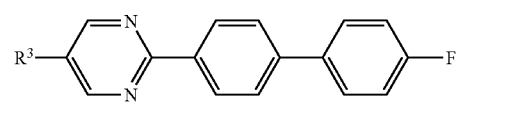
(7-1) 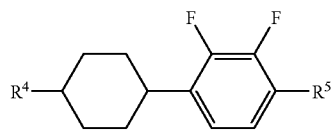
(7-2) 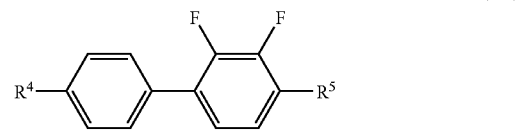
(7-3) 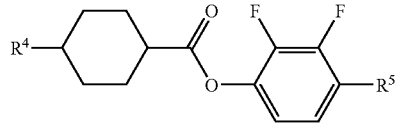
(8-1) 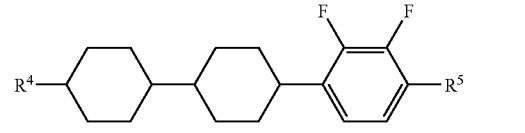
(8-2) 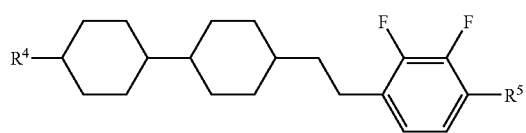
(8-3) 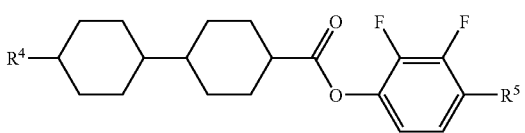

-continued
(8-4)
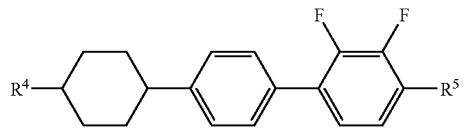
(8-5)
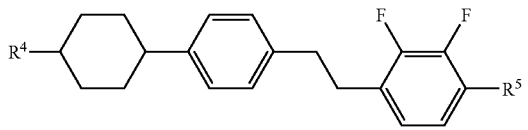
(9-1)
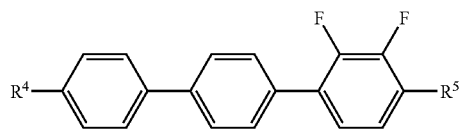
(9-2)
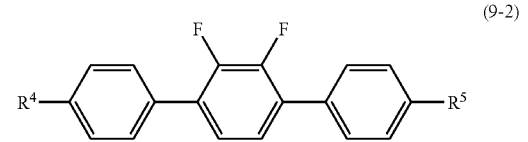
(9-3)
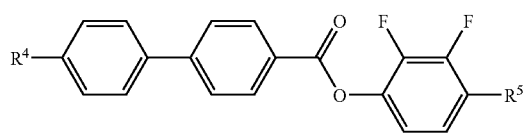
(10-1)
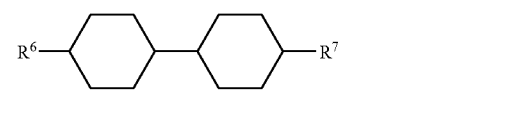
(10-2)
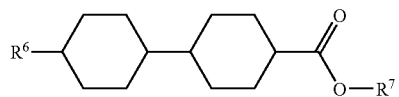
(10-3)
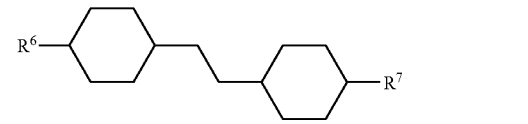
(10-4)
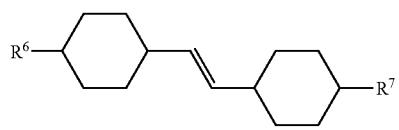
(10-5)
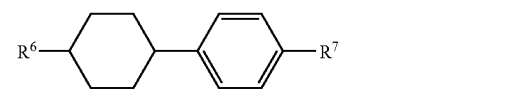
(10-6)
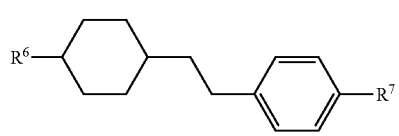
(10-7)
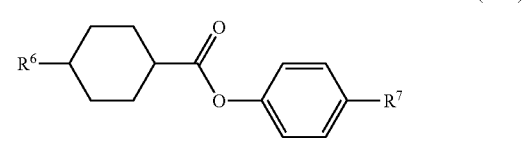
(10-8)
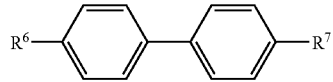
(10-9)
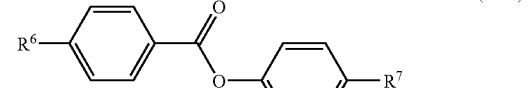
(10-10)
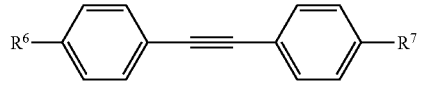
(10-11)
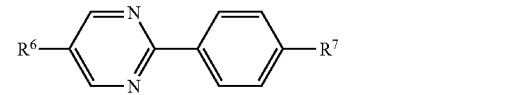
(11-1)
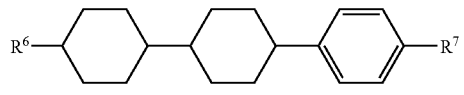
(11-2)
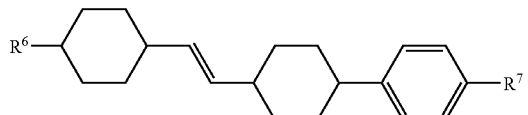
(11-3)
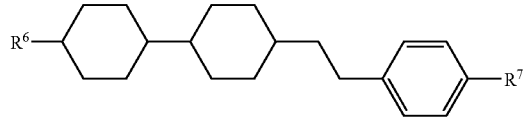
(11-4)
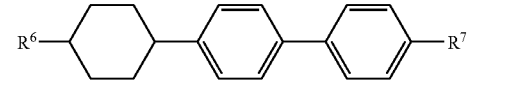
(11-5)
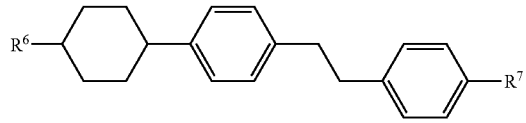
(11-6)
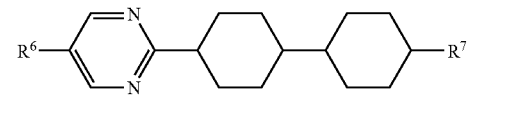

-continued
(11-7) 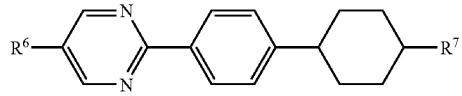
(11-8) 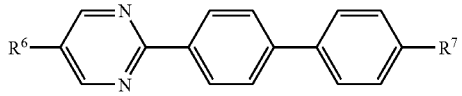
(11-9) 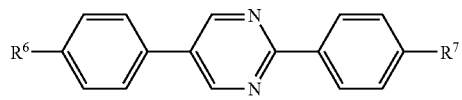
(11-10) 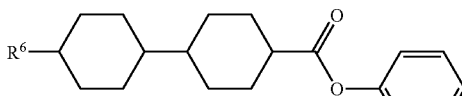
(11-11) 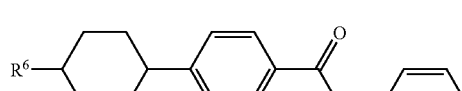
(11-12) 
(11-13) 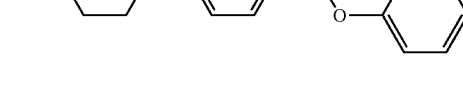
(11-14) 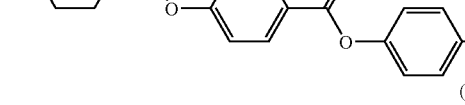
(11-15) 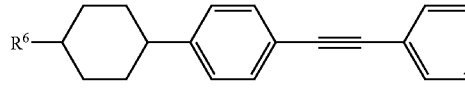
(11-16) 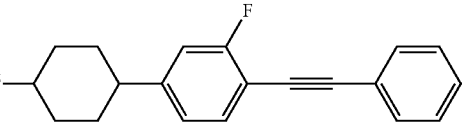
(11-17) 
(11-18) 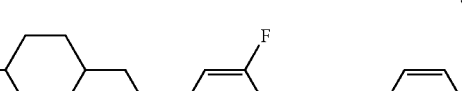
(12-1) 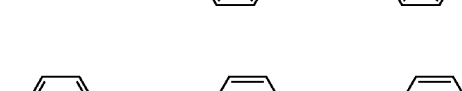
(12-2) 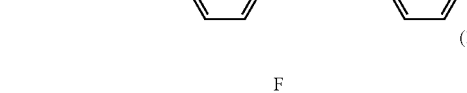
(12-3) 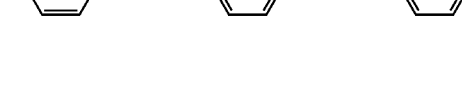
(12-4) 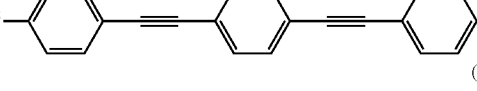
(12-5) 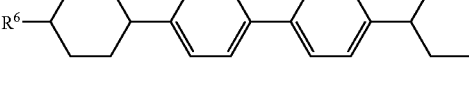
(12-6) 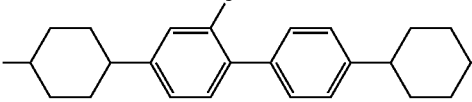
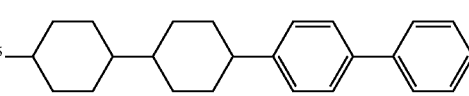
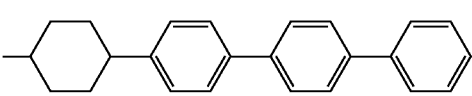
(Op-1) 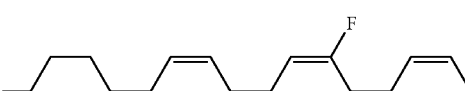
(Op-2) 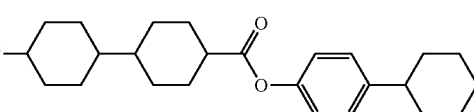
(Op-3) 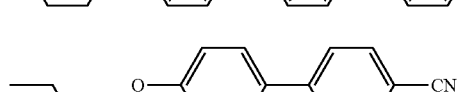

-continued
(Op-4)
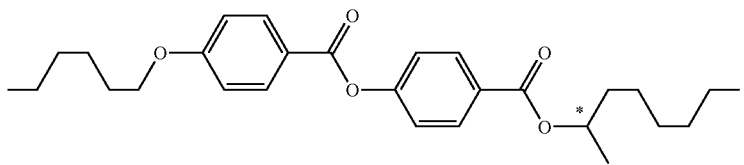
(Op-5)
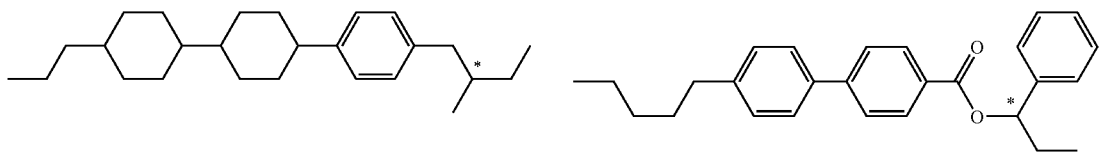
(Op-6)
(Op-7)
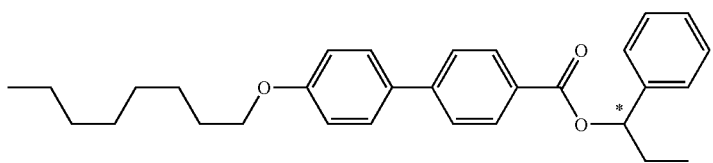
(Op-8)
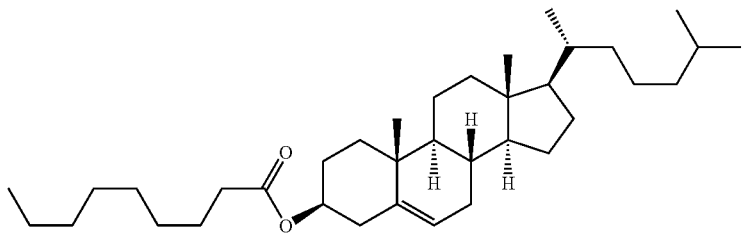
(Op-9)
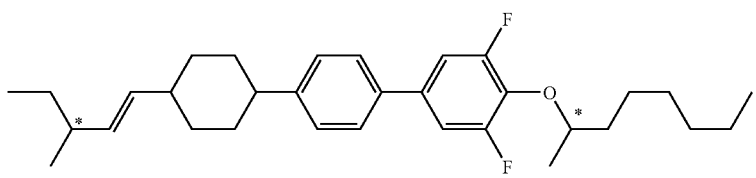
(Op-10)
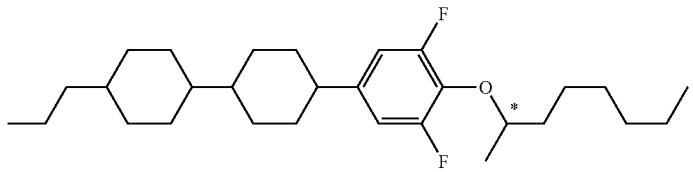
(Op-11)
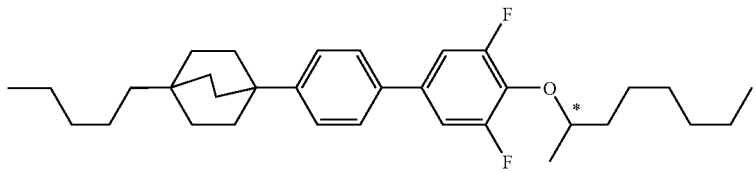
(Op-12)
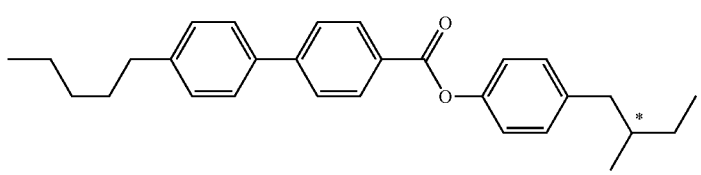

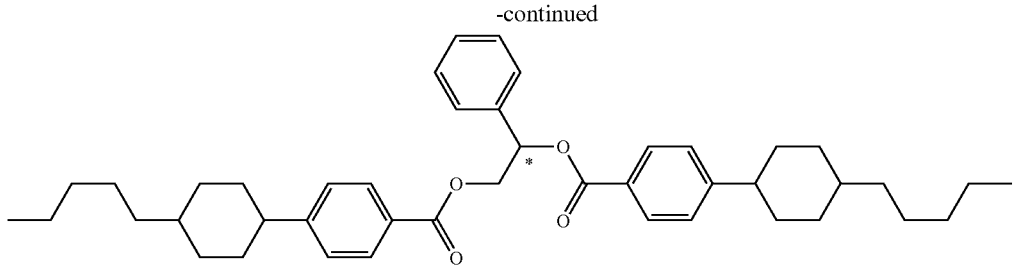
(Op-13)

The composition of the present invention is prepared by a known method. For example, compounds which are the components are mixed followed by heating so that they are dissolved each other. It is also possible to add an appropriate additive to the composition to adjust the physical property of the composition. The additive as such has been well known among persons skilled in the art. For an object of inducing a helical structure of liquid crystal to give a necessary torsion angle preventing a reversed torsion, a chiral dopant is added. Examples of the chiral dopant are the above-mentioned optically active compounds (Op-1) to (Op-13).

A chiral dopant is added to the composition to adjust the pitch of the torsion. With regard to the pitch of the torsion, the range of 40 to 200 μm is preferred for TN and TN-TFT modes and the range of 6 to 20 μm is preferred for an STN mode. For a bistable twisted nematic mode, the range of 1.5 to 4 μm is preferred. A dichromatic dye which is a compound such as merocyanine, styryl, azo, azomethine, azoxy, quinophthalone, anthraquinone or tetrazine is added to prepare a composition for a GH mode. In a composition for a PC mode, a chiral dopant is added in a relatively large amount. Generally, in order to adjust the temperature-dependency of pitch, at least two chiral dopants may be added.

The composition of the present invention may be used for display elements of the mode such as TN, TN-TFT, bistable TN, STN, IPS, GH, DS, VA, OCB, ECB and PC. The composition may also be used for an NCAP prepared by making nematic liquid crystals into microcapsules and a polymer dispersed liquid crystal display element (PD-LCD) where three-dimensional network polymer is formed in liquid crystal such as a polymer network liquid crystal display element (PN-LCD). The display element of the present invention using the composition has short response time, small electricity consumption, high contrast and high voltage retaining rate.

EXAMPLES

The present invention will now be illustrated in detail by way of the following Examples. The present invention is not limited by those Examples. The resulting compounds were identified by the methods such as nuclear magnetic resonance spectrum and mass spectrum. In the phase transition temperature of the compound, C, SmB, SmE, SmG, N and I stand for crystal, smectic B phase, smectic E phase, smectic G phase, nematic phase and isotropic phase, respectively. Unit of the temperature is ° C. An expression reading "C 50.6 SmB 53.7 N 56.2 I." means that transition temperature from C phase to SmB phase is 50.6° C., transition temperature of SmB phase to N phase is 53.7° C. and transition temperature of N phase to I phase is 56.2° C. Method for the measurement of the phase transition temperature of the compound is the same as that for the measurement of transition temperature of nematic phase-isotropic phase (NI) in a composition. Viscosity, optical anisotropy and dielectric anisotropy of the compound were measured after dissolving the compound in appropriate mother liquid crystals. An example of the mother liquid crystal is a composition as shown below.

| | |
|---|---|
| $C_3H_7$—⟨⟩—⟨⟩—CN | 24% |
| $C_5H_{11}$—⟨⟩—⟨⟩—CN | 36% |
| $C_7H_{15}$—⟨⟩—⟨⟩—CN | 25% |
| $C_5H_{11}$—⟨⟩—⟨⟩—⟨⟩—CN | 15% |

Miscibility of the Compound: Several compounds having similar structure were mixed to prepare a mother liquid crystal having a nematic phase. A composition was prepared by mixing the compound to be measured and the mother liquid crystal. An example of the mixing rate is 15% of the compound and 85% of the mother liquid crystal. The composition was preserved for 30 days at the temperature of as low as −20° C. or −30° C. It was observed whether a part of the composition changed to crystal (or smectic phase). The mixing ratio and the preserving temperature were adjusted if necessary. From the result of the measurement conducted by that method, the condition where the crystal (or smectic phase) was separated and the crystal (or smectic phase) was not separated were determined.

Example 1

Manufacture of (E)-1,2,3,3,3-hexafluoro-1-(trans-4-(trans-4-pentylcyclohexyl)cyclohexyl)propene (1-aa-1, Ra=$C_5H_{11}$)

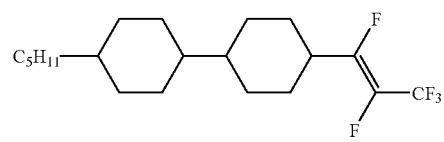

In a nitrogen atmosphere, 100 mmol of lithium were gradually added at 0° C. to a solution of 50 mmol of 4,4'-di-tert-butyl biphenyl in 100 ml of THF followed by stirring at the same temperature for 2 hours more. After that, the reaction mixture was cooled to −70° C. and a solution of 25 mmol of 1-chloro-trans-4-(trans-4-pentylcyclohexyl)-cyclohexane in 50 ml of THF was dropped thereinto with stirring at the same temperature. After stirring for 2 hours, 100 mmol of 1,1,2,3,3,3-hexafluoropropene was blown thereinto at the same temperature under stirring. After 30 minutes, the reaction mixture was poured into 0.1N hydrochloric acid cooled with ice. The reaction mixture was extracted with toluene and the extract was washed with water and dried over anhydrous magnesium sulfate. The solvent was evaporated in vacuo and the resulting residue was purified by a column chromatography (silica gel; developing solvent: heptane). Recrystallization from ethanol gave 8 mmol of the title compound. Colorless needles.

C 50.6 SmB 53.7 N 56.2 I.

Example 2

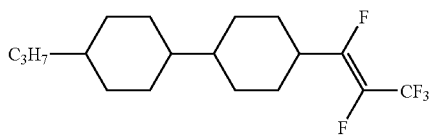

Manufacture of (E)-1,2,3,3,3-hexafluoro-1-(trans-4-(trans-4-propylcyclohexyl)cyclohexyl)propene (1-aa-1, Ra=C$_3$H$_7$)

The title compound was manufactured using 1-chloro-trans-4-(trans-4-propylcyclohexyl)cyclohexane instead of 1-chloro-trans-4-(trans-4-pentylcyclohexyl)-cyclohexane in Example 1.

C 49.5 SmB 62.6 I.

Example 3

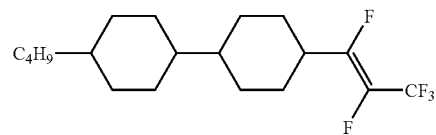

Manufacture of (E)-1,2,3,3,3-hexafluoro-1-(trans-4-(trans-4-butylcyclohexyl)cyclohexyl)propene (1aa-1, Ra=C$_4$H$_9$)

The title compound was manufactured using 1-chloro-trans-4-(trans-4-butylcyclohexyl)cyclohexane instead of 1-chloro-trans-4-(trans-4-pentylcyclohexyl)-cyclohexane in Example 1.

C 18.9 SmE 31.7 SmB 41.9 I.

Example 4

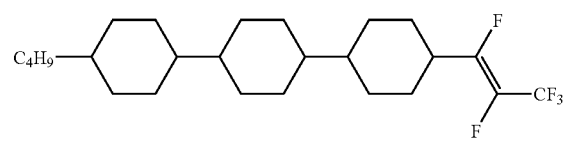

Manufacture of (E)-1,2,3,3,3-hexafluoro-1-(trans-4-(trans-4-(trans-4-butylcyclohexyl)cyclohexyl)cyclohexyl)-propene (1-ba-1, Ra=C$_4$H$_9$)

The title compound was manufactured using 1-chloro-trans-4-(trans-4-(trans-4-butylcyclohexyl)cyclohexyl)-cyclohexane instead of 1-chloro-trans-4-(trans-4-pentylcyclohexyl)-cyclohexane in Example 1.

C 61.0 EmG 171.5 SmB 194.5 N 223.0 I.

A compound (1-aa-1) to a compound (1-cc-15) are synthesized according to Examples 1 to 4 or to a method mentioned in referential books. Those compounds were listed under the formula (1). For example, the compound (1-aa-1) means the following five. Thus, they are C$_3$H$_7$—H—H—CF=CFCF$_3$, C$_4$H$_9$—H—H—CF=CFCF$_3$, C$_5$H$_{11}$—H—H—CF=CFCF$_3$, CH$_3$OCH$_2$—H—H—CF=CFCF$_3$ and CH$_2$=CHC$_2$H$_4$—H—H—CF=CFCF$_3$. The symbols H is 1,4-cyclohexylene.

| Ra | |
|---|---|
| | 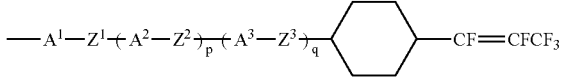 |
| (1-aa-1) | C$_3$H$_7$, C$_4$H$_9$, C$_5$H$_{11}$, CH$_3$OCH$_2$, CH$_2$=CHC$_2$H$_4$ |
| |  |
| (1-aa-2) | C$_2$H$_5$, C$_5$H$_{11}$, C$_7$H$_{15}$, C$_2$H$_5$O, CH$_3$CH=CH |
| | 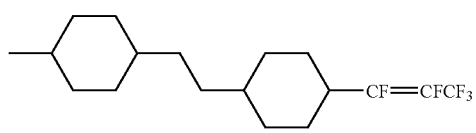 |

-continued

| Ra | $-A^1-Z^1+(A^2-Z^2)_p+(A^3-Z^3)_q$ —⟨cyclohexyl⟩—CF=CFCF$_3$ |
|---|---|
| (1-aa-3) | C$_3$H$_7$, C$_5$H$_{11}$, C$_6$H$_{13}$, CH$_3$OCH$_2$, CH$_2$=CH |
| (1-aa-4) | C$_3$H$_7$, C$_5$H$_{11}$, C$_7$H$_{15}$, C$_3$H$_7$O, CH$_2$=CH |
| (1-aa-5) | C$_3$H$_7$, C$_4$H$_9$, C$_6$H$_{13}$, CH$_3$O, CH$_2$=CHC$_2$H$_4$ |
| (1-aa-6) | C$_2$H$_5$, C$_3$H$_7$, C$_5$F$_{11}$, C$_4$H$_9$O, CH$_3$CH=CHCH$_2$ |
| (1-aa-7) | C$_2$H$_5$, C$_3$H$_7$, C$_7$H$_{15}$, C$_4$H$_9$O, CH$_2$=CH |
| (1-aa-8) | C$_3$H$_7$, C$_5$H$_{11}$, C$_6$H$_{13}$, CH$_3$O, CH$_2$=CHCH$_2$ |
| (1-ab-1) | C$_3$H$_7$, C$_4$H$_9$, C$_5$H$_{11}$, C$_2$H$_5$OCH$_2$, CH$_3$CH=CHC$_2$H$_4$ |
| (1-ab-2) | C$_3$H$_7$, C$_5$H$_{11}$, C$_6$H$_{13}$, C$_3$H$_7$CO, CH$_3$CH=CH |
| (1-ab-3) | C$_3$H$_7$, C$_5$H$_{11}$, C$_7$H$_{15}$, CH$_3$OCH$_2$, CH$_2$=CHC$_2$H$_4$ |
| (1-ab-4) | C$_2$H$_5$, C$_3$H$_7$, C$_6$H$_{13}$, C$_2$H$_5$O, CH$_2$=CHCH$_2$O |
| (1-ab-5) | C$_3$H$_7$, C$_4$H$_9$, C$_5$H$_{11}$, C$_5$H$_{11}$O, CH$_2$=CHC$_3$H$_6$ |

-continued

| | Ra | —A¹—Z¹—(A²—Z²)ₚ—(A³—Z³)_q—⌬—CF=CFCF₃ |
|---|---|---|
| (1-ab-6) | C₂H₅, C₃H₇, C₅H₁₁, C₄H₉O, CH₃CH=CHCH₂ | —⌬—CH₂CH₂—⌬—CF=CFCF₃ |
| (1-ab-7) | C₃H₇, C₄H₉, C₅H₁₁, C₂H₅O, CH₂=CHC₂H₄ | —⌬(F)—CH₂CH₂—⌬—CF=CFCF₃ |
| (1-ab-8) | C₃H₇, C₄H₉, C₃H₇(CH₃)CH₂, C₃H₇O, CH₃CH=CH | —⌬(F,F)—CH₂CH₂—⌬—CF=CFCF₃ |
| (1-ab-9) | CH₃, C₃H₇, NCC₇H₁₄, CH₃O, CH₃CH=CHCH₂O | —⌬(F,F)—CH₂CH₂—⌬—CF=CFCF₃ |
| (1-ab-10) | C₂H₅, C₄H₉, C₅H₁₁, C₂H₅O, CH₂=CH | —⌬—CH₂O—⌬—CF=CFCF₃ |
| (1-ab-11)–(1-ab-18) | | |
| (1-ab-11) | C₃H₇, C₄H₉, C₅H₁₁, C₂H₅O, CH₃CH=CH | —⌬(F)—CH₂O—⌬—CF=CFCF₃ |
| (1-ab-12) | C₂H₅, C₃H₇, C₅H₁₁, C₃H₇S, CH₂=CHC₂H₄ | —⌬(F,F)—CH₂O—⌬—CF=CFCF₃ |
| (1-ab-13) | C₃H₇, C₄H₉, C₅H₁₁, C₂H₅OC₂H₄, CH₂CHCH₂ | —⌬—C(=O)O—⌬—CF=CFCF₃ |
| (1-ab-14) | C₃H₇, C₅H₁₁, C₇H₁₅, CH₃OCH₂, CH₂=CHC₂H₄ | —⌬(F)—C(=O)O—⌬—CF=CFCF₃ |

-continued

| | Ra | —A¹—Z¹—(A²—Z²)$_p$—(A³—Z³)$_q$—[cyclohexyl]—CF=CFCF₃ |
|---|---|---|
| (1-ab-15) | C₂H₅, C₃H₇, C₅H₁₁, C₄H₉O, CH₃CH=CHC₂H₅ | 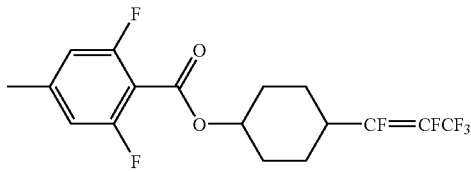 |
| (1-ab-16) | C₃H₇, C₄H₉, C₅H₁₁, CH₃OCH₂, CH₂=CHC₂H₄ | 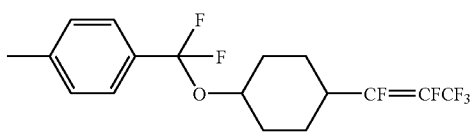 |
| (1-ab-17) | C₃H₇, C₄H₉, C₅H₁₁, CH₃O, CH₂=CHC₂H₄ | 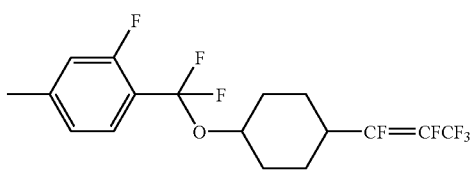 |
| (1-ab-18) | C₃H₇, C₅H₁₁, C₇H₁₅, CH₃O, CH₃CH=CH | 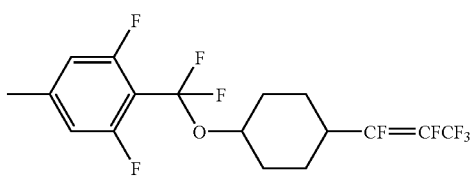 |
| (1-ba-1) | C₃H₇, C₄H₉, C₅H₁₁, CH₃OCH₂, CH₂=CH | 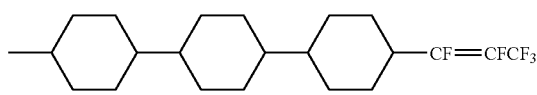 |
| (1-ba-2) | C₃H₇, C₅H₁₁, C₂H₅(C₂H₅)C₂H₄, C₂H₅O, CH₃CH=CH | 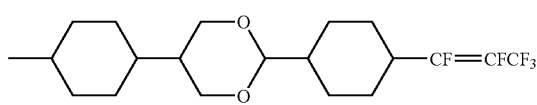 |
| (1-ba-3) | C₅H₁₁, C₇H₁₅, C₆H₁₃O, CH₂=CH | 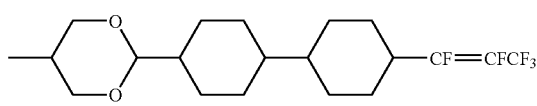 |
| (1-ba-4) | C₃H₇, C₄H₉, C₆H₁₃, C₃H₇O, CH₂=CHC₂H₄ | 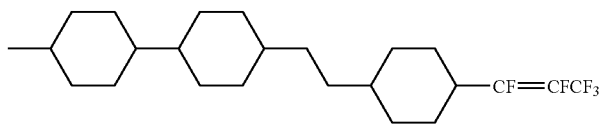 |
| (1-ba-5) | C₃H₇, C₄H₉, C₅H₁₁, C₂H₅O, CH₃CH=CH | 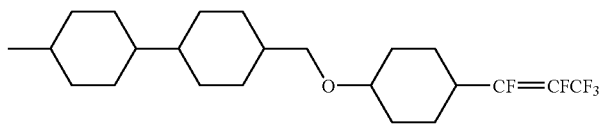 |
| (1-ba-6) | C₂H₅, C₃H₇, C₅H₁₁, C₄H₉O, C₃H₇CH=CH | 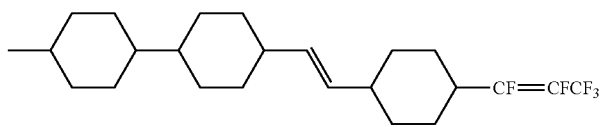 |

-continued

|  | Ra | $-A^1-Z^1-(A^2-Z^2)_p-(A^3-Z^3)_q-\bigcirc-CF=CFCF_3$ |
|---|---|---|
| (1-ba-7) | $C_3H_7, C_4H_9, C_5H_{11}, C_2H_5OC_3H_6,$ $CH_2=CH$ | 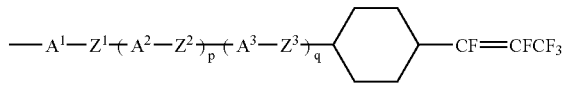 |
| (1-ba-8) | $C_2H_5, C_3H_7, C_4F_9, C_2H_5O,$ $CH_3CH=CH$ | 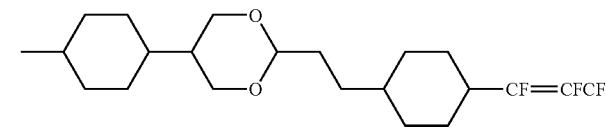 |
| (1-ba-9) | $C_2H_5, C_3H_7, C_8H_{17}, CH_3O,$ $C_2H_5CH=CHCH_2$ | 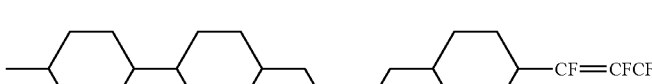 |
| (1-ba-10) | $C_4H_9, C_5H_{11}, C_4H_9O,$ $CH_2CHC_2H_4$ | 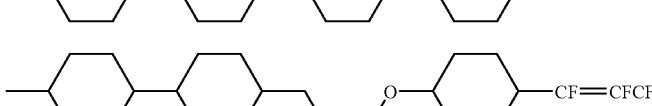 |
| (1-ba-20) | $C_2H_5, C_3H_7, C_5H_{11}, C_4H_9O,$ $C_2H_5CH=CH$ | 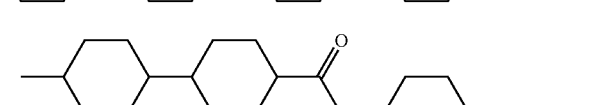 |
| (1-ba-11) | $C_3H_7, C_4H_9, C_5H_{11}, C_3H_7OCH_2,$ $CH_2=CHC_2H_4$ | 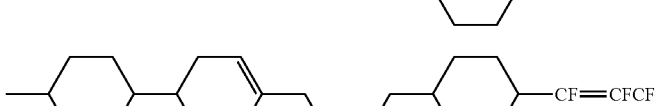 |
| (1-ba-12) | $C_3H_7, C_4H_9, C_7H_{15}, CH_3OCH_2,$ $CH_3CH=CH$ | 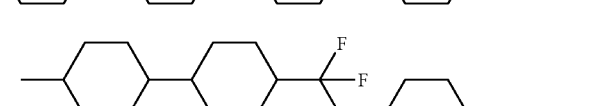 |
| (1-ba-13) | $C_2H_5, C_4H_9, C_5H_{11}, C_2H_5O,$ $CH_2=CH$ |  |
| (1-ba-14) | $C_3H_7, C_5H_{11}, C_6H_{13}, CH_3O,$ $CH_2=CH$ | 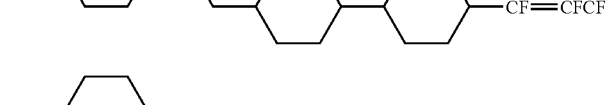 |
| (1-ba-15) | $CH_3, C_2H_5, C_3H_7, C_7H_{15}O,$ $C_3H_7CH=CH$ | 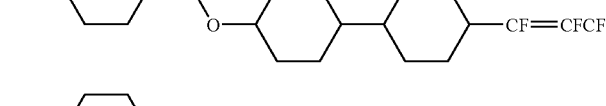 |
| (1-ba-16) | $C_2H_5, C_3H_7, C_4H_9, C_5H_{11}O,$ $C_2H_5CH=CHCH_2$ | 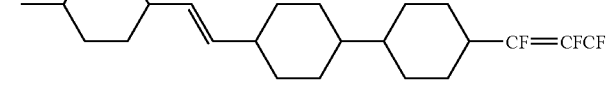 |
| (1-ba-17) | $C_3H_7, C_4H_9, C_5H_{11}, CH_3OC_2H_4,$ $C_2H_5CH=CH$ | 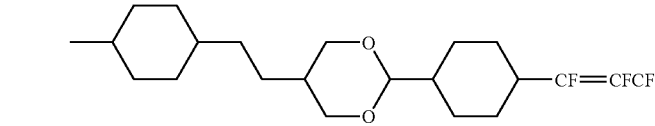 |

-continued

| Ra | $-A^1-Z^1-(A^2-Z^2)_p-(A^3-Z^3)_q-$ cyclohexyl$-CF=CFCF_3$ |
|---|---|
| (1-ba-21) $C_2H_5$, $C_3H_7$, $C_6H_{13}$, $C_2H_5O$, $CH_2=CH$ | 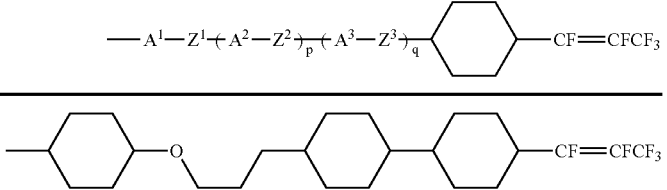 |
| (1-ba-18) $C_3H_7$, $C_4H_9$, $C_5H_{11}$, $C_4H_9O$, $CH_3CH=CH$ | 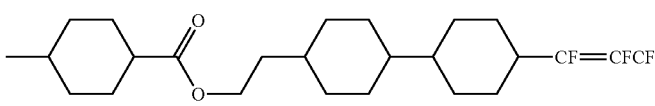 |
| (1-ba-19) $C_2H_5$, $C_3H_7$, $C_5H_{11}$, $C_2H_5OC_3H_6$, $CH_3CH=CHCH_2$ | 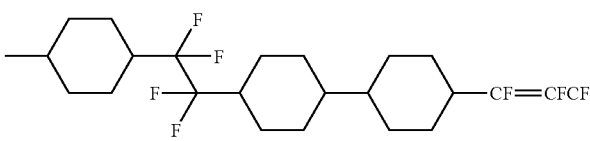 |
| (1-bb-1) $C_3H_7$, $C_5H_{11}$, $C_6H_{13}$, $C_2H_5O$, $C_3H_7CH=CH$ | 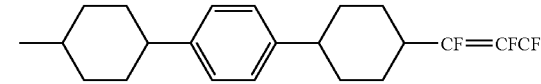 |
| (1-bb-2) $C_3H_7$, $C_4H_9$, $C_7H_{15}$, $C_3H_7O$, $CH_3CH=CH$ | 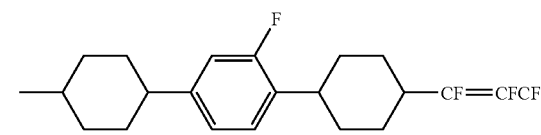 |
| (1-bb-3) $C_3H_7$, $C_5H_{11}$, $C_6H_{13}$, $C_2H_5O$, $CH_3CH=CHC_2H_4$ | 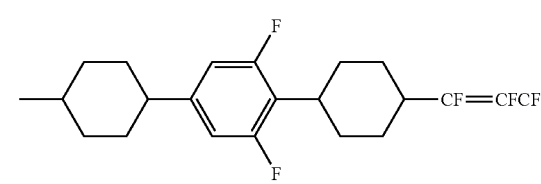 |
| (1-bb-4) $C_2H_5$, $C_3H_7$, $C_4H_9$, $C_4H_9O$, $C_2H_5CH=CHCH_2O$ | 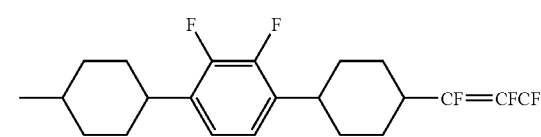 |
| (1-bb-5) $CH_3$, $C_2H_5$, $C_5H_{11}$, $CH_3OCH_2$, $CH_2=CHC_2H_4$ | 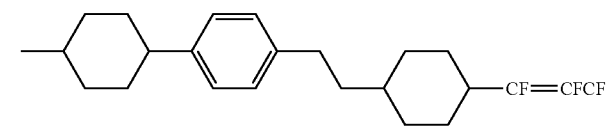 |
| (1-bb-6) $C_2H_5$, $C_3H_7$, $C_6H_{13}$, $C_2H_5OCH_2$, $CH_2=CH$ | 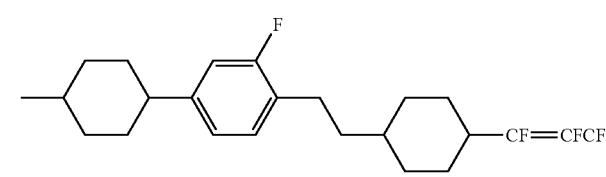 |
| (1-bb-7) $C_2H_5$, $C_3H_7$, $C_4H_9$, $C_2H_5O$, $CH_3CH=CH$ | 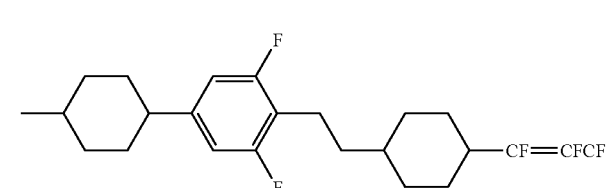 |

-continued

| Ra | $-A^1-Z^1+(A^2-Z^2)_p+(A^3-Z^3)_q$—[cyclohexyl]—CF=CFCF$_3$ |
|---|---|
| (1-bb-8) | C$_3$H$_7$, C$_4$H$_9$, C$_5$H$_{11}$, C$_5$H$_{11}$O, CH$_2$=CHC$_3$H$_6$ |
| (1-bb-9) | C$_2$H$_5$, C$_4$H$_9$, C$_5$H$_{11}$, C$_2$H$_5$O, C$_2$H$_5$CH=CHCH$_2$ |
| (1-bb-10) | C$_3$H$_7$, C$_4$H$_9$, C$_7$H$_{15}$, C$_3$H$_7$O, CH$_2$=CHC$_2$H$_4$ |
| (1-bb-11) | C$_2$H$_5$, C$_4$H$_9$, C$_5$H$_{11}$, C$_2$H$_5$O, CH$_3$CH=CH |
| (1-bb-12) | C$_3$H$_7$, C$_4$H$_9$, C$_5$H$_{11}$, CH$_3$OCH$_2$, CH$_2$=CH |
| (1-bb-13) | C$_2$H$_5$, C$_4$H$_9$, C$_5$H$_{11}$, C$_2$H$_5$O, CH$_3$CH=CH |
| (1-bb-14) | CH$_3$, C$_4$H$_9$, C$_6$H$_{13}$, CH$_3$OC$_3$H$_6$, CH$_2$=CH |
| (1-bb-15) | C$_2$H$_5$, C$_3$H$_7$, C$_5$H$_{11}$, C$_2$H$_5$O, C$_2$H$_5$CH=CHCH$_2$ |
| (1-bb-16) | C$_3$H$_7$, C$_4$H$_9$, C$_5$H$_{11}$, C$_4$H$_9$O, CH$_2$=CHC$_2$H$_4$ |
| (1-bb-17) | C$_3$H$_7$, C$_5$H$_{11}$, C$_7$H$_{15}$, C$_2$H$_5$O, CH$_2$=CH |

-continued

|  | Ra | $-A^1-Z^1+(A^2-Z^2)_p-(A^3-Z^3)_q$—⟨cyclohexyl⟩—CF=CFCF$_3$ |
|---|---|---|
| (1-bb-18) | C$_3$H$_7$, C$_5$H$_{11}$, C$_6$H$_{13}$, C$_2$H$_5$O, CH$_3$CH=CH | |
| (1-bb-19) | C$_3$H$_7$, C$_4$H$_9$, C$_6$H$_{13}$, C$_3$H$_7$O, CH$_2$=CHC$_2$H$_4$ | |
| (1-bb-20) | C$_2$H$_5$, C$_3$H$_7$, C$_4$H$_9$, CH$_3$O, CH$_3$CH=CH | |
| (1-bb-21) | C$_2$H$_5$, C$_3$H$_7$, C$_5$H$_{11}$, C$_4$H$_9$O, C$_3$H$_7$CH=CH | |
| (1-bb-22) | C$_3$H$_7$, C$_4$H$_9$, C$_5$H$_{11}$, CH$_3$O, CH$_2$=CHC$_2$H$_4$ | |
| (1-bb-23) | C$_3$H$_7$, C$_4$H$_9$, C$_6$H$_{13}$, CH$_3$OCH$_2$, CH$_2$=CH | |
| (1-bb-24) | CH$_3$, C$_5$H$_{11}$, C$_6$H$_{13}$, C$_2$H$_5$O, CH$_3$CH=CH | |
| (1-bb-25) | C$_3$H$_7$, C$_4$H$_9$, C$_6$H$_{13}$, C$_3$H$_7$O, CH$_2$=CHC$_2$H$_4$ | |
| (1-bc-1) | C$_3$H$_7$, C$_4$H$_9$, C$_5$H$_{11}$, C$_2$H$_5$O, CH$_3$CH=CH | |

-continued
| | Ra | |
|---|---|---|
| (1-bc-2) | $C_2H_5$, $C_3H_7$, $C_5H_{11}$, $C_4H_9S$, $C_3H_7CH=CH$ | |
| (1-bc-3) | $C_3H_7$, $C_4H_9$, $C_5H_{11}$, $CH_3OCH_2$, $CH_2=CH$ | |
| (1-bc-4) | $C_3H_7$, $C_4H_9$, $C_5H_{11}$, $C_2H_5OCH_2$, $CH_2=CHC_2H_4$ | |
| (1-bc-5) | $C_2H_5$, $C_4H_9$, $C_6H_{13}$, $C_3H_7O$, $CH_2=CHC_2H_4$ | |
| (1-bc-6) | $C_2H_5$, $C_5H_{11}$, $C_7H_{15}$, $C_7H_{15}O$, $CH_2=CH$ | |
| (1-bd-1) | $C_3H_7$, $C_4H_9$, $C_5H_{11}$, $C_3H_7CO$, $CH_2=CHC_2H_4$ | |
| (1-bd-2) | $C_2H_5$, $C_3H_7$, $C_7H_{15}$, $C_2H_5O$, $C_2H_5CH=CHCH_2$ | |
| (1-bd-3) | $C_3H_7$, $C_4H_9$, $C_5H_{11}$, $C_4H_9O$, $CH_2=CHC_2H_4$ | |
| (1-bd-4) | $C_2H_5$, $C_3H_7$, $C_4H_9$, $C_2H_5O$, $CH_3CH=CHCH_2O$ | |
| (1-bd-5) | $C_3H_7$, $C_4H_9$, $C_5H_{11}$, $CH_3OCH_2$, $CH_2=CHCH_2$ | |
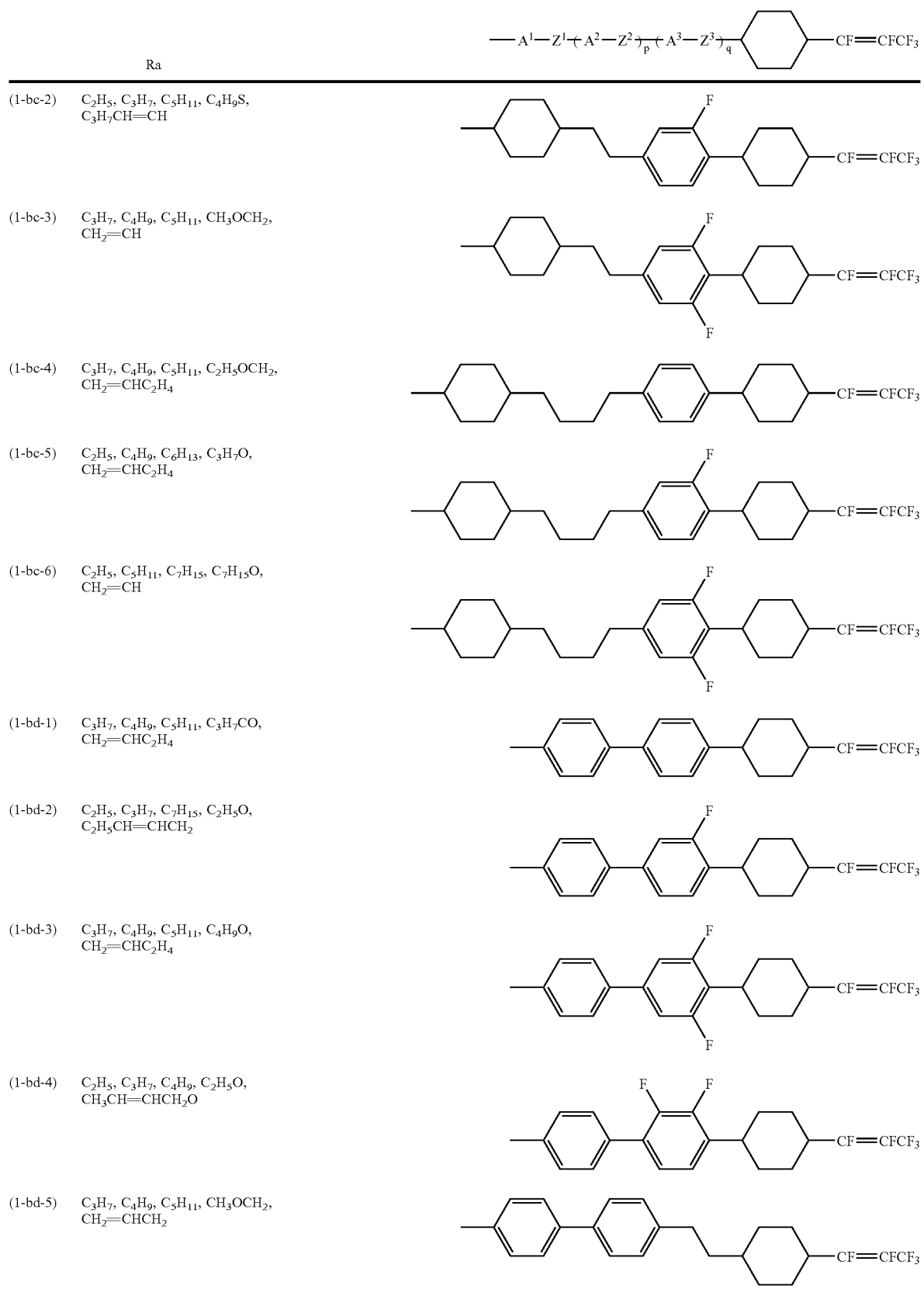

-continued

| | Ra | —A¹—Z¹—(A²—Z²)ₚ—(A³—Z³)_q—[cyclohexyl]—CF=CFCF₃ |
|---|---|---|
| (1-bd-6) | $C_2H_5$, $C_4H_9$, $C_5H_{11}$, $CH_3OCH_2$, $CH_2=CHC_3H_6$ | 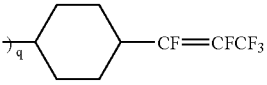 |
| (1-bd-7) | $C_3H_7$, $C_4H_9$, $C_5H_{11}$, $C_2H_5O$, $CH_3CH=CH$ | 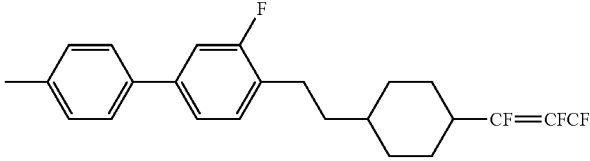 |
| (1-bd-8) | $C_2H_5$, $C_3H_7$, $C_5H_{11}$, $C_3H_7O$, $C_3H_7CH=CH$ | 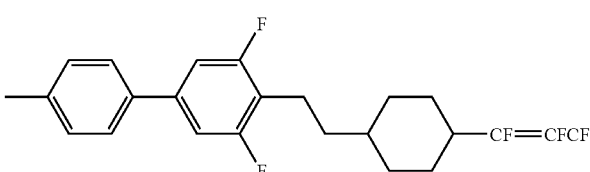 |
| (1-bd-9) | $C_2H_5$, $C_5H_{11}$, $C_7H_{15}$, $C_6H_{13}O$, $CH_3C\equiv C$ | 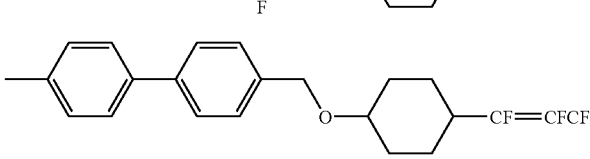 |
| (1-bd-10) | $C_3H_7$, $C_5H_{11}$, $C_8H_{17}$, $C_2H_5O$, $CH_3CH=CHC_2H_4$ | 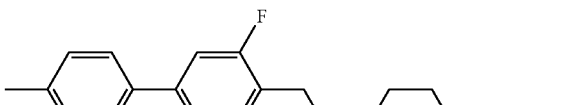 |
| (1-bd-11) | $C_2H_5$, $C_3H_7$, $C_5H_{11}$, $CH_3O$, $C_2H_5CH=CHCH_2$ | 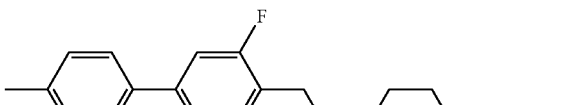 |
| (1-bd-12) | $C_2H_5$, $C_3H_7$, $C_4H_9$, $C_2H_5O$, $CH_3CH=CHCH_2$ | 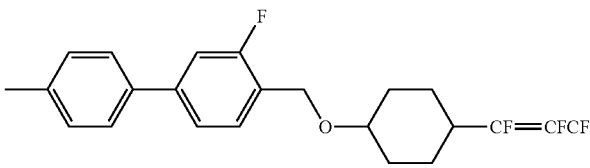 |
| (1-bd-13) | $C_3H_7$, $C_4H_9$, $C_5H_{11}$, $C_2H_5OCH_2$, $CH_2=CHC_2H_4$ | 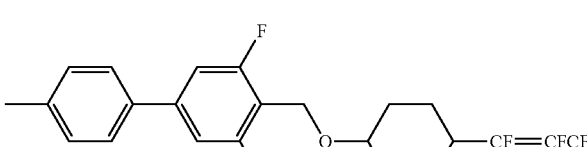 |
| (1-bd-14) | $C_3H_7$, $C_5H_{11}$, $C_7H_{15}$, $C_4H_9O$, $CH_3CH=CH$ | 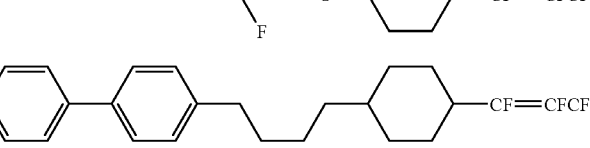 |
| (1-bd-15) | $C_3H_7$, $C_4H_9$, $C_5H_{11}$, $C_2H_5O$, $CH_3CH=CHC_2H_4$ | 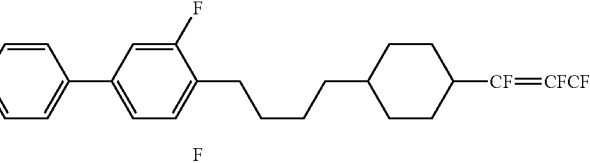 |

-continued

| Ra | $-A^1-Z^1-(A^2-Z^2)_p-(A^3-Z^3)_q$ —⌬— CF=CFCF$_3$ |
|---|---|
| (1-bd-16) C$_2$H$_5$, C$_5$H$_{11}$, C$_6$H$_{13}$, C$_2$H$_5$OCH$_2$, CH$_2$=CHCH$_2$ | |
| (1-bd-17) C$_2$H$_5$, C$_3$H$_7$, C$_5$H$_{11}$, C$_4$H$_9$O, C$_3$H$_7$CH=CH | |
| (1-bd-18) C$_3$H$_7$, C$_4$H$_9$, C$_5$H$_{11}$, CH$_3$OCH$_2$, C$_3$H$_7$C≡C | |
| (1-bd-19) C$_2$H$_5$, C$_4$H$_9$, C$_5$H$_{11}$, C$_4$H$_9$O, CH$_2$=CHC$_2$H$_4$ | |
| (1-bd-20) C$_3$H$_7$, C$_4$H$_9$, C$_6$H$_{13}$, CH$_3$O, CH$_3$CH=CHC$_2$H$_4$ | |
| (1-bd-21) C$_3$H$_7$, C$_4$H$_9$, C$_5$H$_{11}$, CH$_3$OCH$_2$, CH$_2$=CHCH$_2$ | |
| (1-bd-22) C$_3$H$_7$, C$_4$H$_9$, C$_6$H$_{13}$, C$_2$H$_5$O, CH$_2$=CHC$_2$H$_4$ | |
| (1-bd-23) NCC$_2$H$_4$, C$_3$H$_7$, C$_5$H$_{11}$, C$_4$H$_9$O, C$_2$H$_5$CH=CHCH$_2$ | |
| (1-bd-24) C$_2$H$_5$, C$_3$H$_7$, C$_8$H$_{17}$, CH$_3$O, C$_2$H$_5$CH=CHCH$_2$ | |

| Ra | —A¹—Z¹—(A²—Z²)ₚ—(A³—Z³)_q—[cyclohexyl]—CF=CFCF₃ |
|---|---|
| (1-bd-25) C₃H₇, C₄H₉, C₅H₁₁, C₃H₇O, CH₃C≡C | 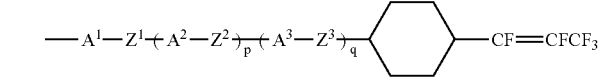 |
| (1-be-1) C₃H₇, C₅H₁₁, C₈H₁₇, CH₃O, CH₃CH=CHC₂H₄ | 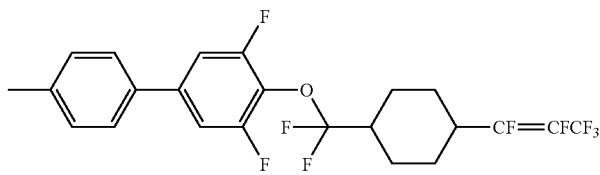 |
| (1-be-2) C₃H₇, C₄H₉, C₆H₁₃, CH₃OCH₂, CH₂=CHC₂H₄ | 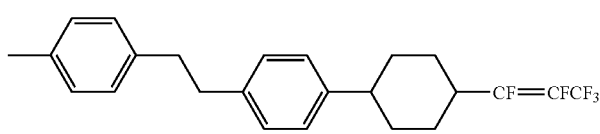 |
| (1-be-3) C₂H₅, C₄H₉, C₅H₁₁, C₂H₅O, CH₂=CHC₂H₄ | 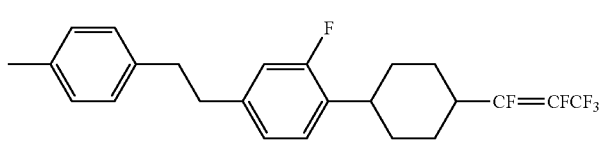 |
| (1-be-4) C₂H₅, C₅H₁₁, C₆H₁₃, C₃H₇O, CH₂=CHCH₂ | 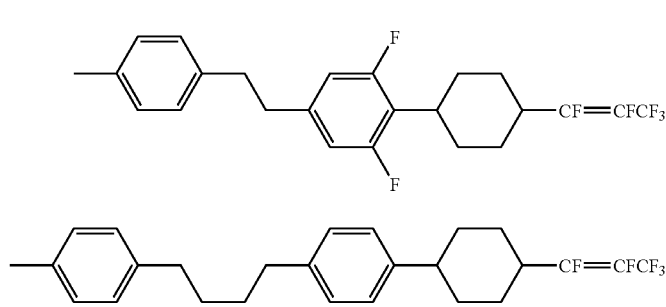 |
| (1-be-5) C₃H₇, C₄H₉, C₅H₁₁, C₄H₉O, C₃H₇CH=CHCH₂ | 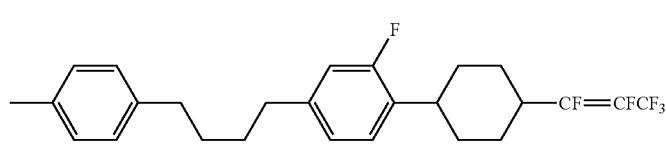 |
| (1-be-6) C₂H₅, C₃H₇, C₄H₉, C₂H₅O, CH₃CH=CHCH₂ | 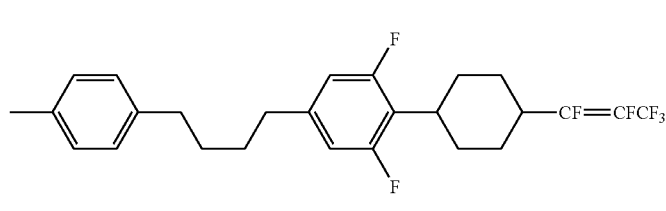 |
| (1-be-7) C₃H₇, C₄H₉, C₅H₁₁, C₂H₅O, CH₃CH=CHC₂H₄ | 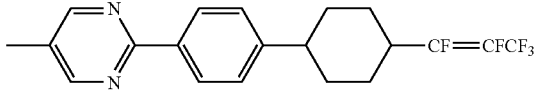 |
| (1-be-8) C₃H₇, C₄H₉, C₇H₁₅, C₃H₇O, CH₃CH=CHC₂H₄ | 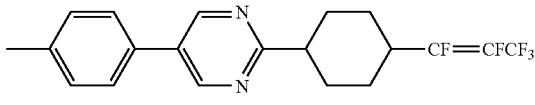 |
| (1-bf-1) C₃H₇, C₄H₉, C₅H₁₁, C₂H₅OC₂H₄, CH₂=CH | 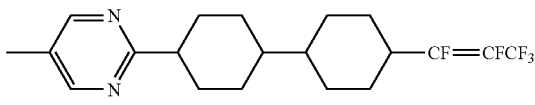 |

| | Ra | —A¹—Z¹—(A²—Z²)ₚ—(A³—Z³)_q—⌬—CF=CFCF₃ |
|---|---|---|
| (1-bf-2) | C₂H₅, C₃H₇, C₄H₉, C₂H₅O, CH₃CH=CH | 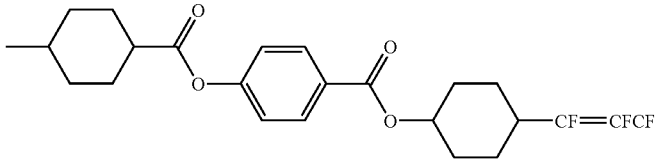 |
| (1-bf-3) | C₃H₇, C₅H₁₁, C₆H₁₃, C₂H₅O, C₂H₅CH=CHCH₂ | 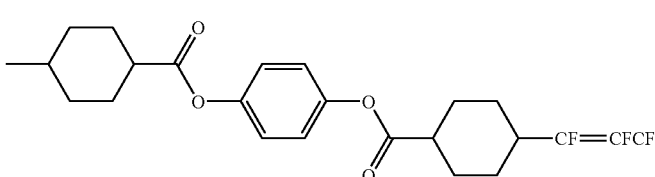 |
| (1-bf-4) | C₂H₅, C₃H₇, C₅H₁₁, CH₃O, CH₃CH=CHC₂H₄ | 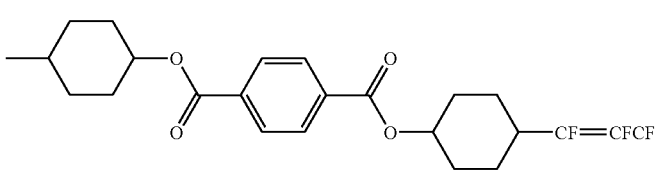 |
| (1-bf-5) | CH₃, C₃H₇, C₆H₁₃, C₂H₅OCH₂, CH₂=CHC₂H₄ | 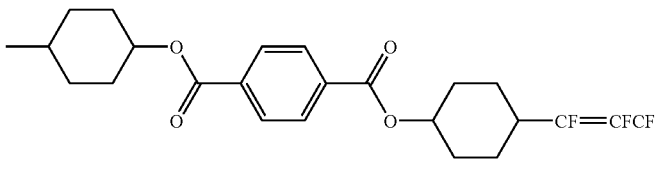 |
| (1-ca-1) | C₂H₅, C₃H₇, C₄H₉, CH₃OCH₂, CH₃CH=CH | 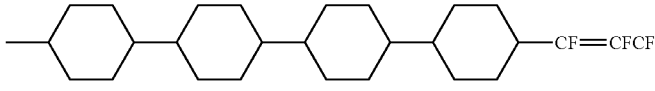 |
| (1-ca-2) | C₃H₇, C₄H₉, C₅H₁₁, C₂H₅O, CH₂=CH | 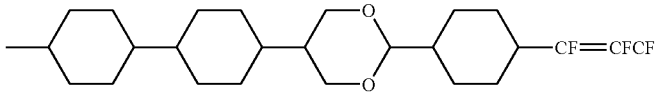 |
| (1-ca-3) | C₂H₅, C₃H₇, C₅H₁₁, CH₃O, CH₃CH=CH | 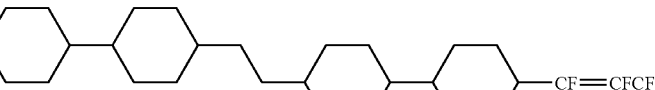 |
| (1-ca-4) | C₃H₇, C₄H₉, C₆F₁₃, C₂H₅OCH₂, CH₂=CH |  |
| (1-ca-5) | C₂H₅, C₃H₇, C₇H₁₅, C₃H₇O, CH₂=CH | 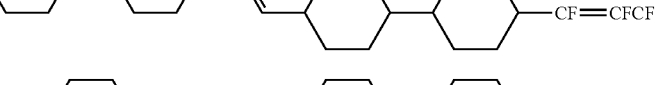 |
| (1-ca-6) | C₃H₇, C₄H₉, C₅H₁₁, C₄H₉O, CH₃CH=CHC₂H₄ | 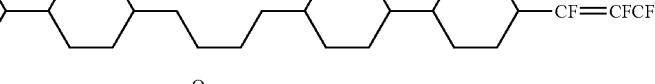 |
| (1-ca-7) | C₃H₇, C₄H₉, C₅H₁₁, C₂H₅O, CH₂=CHC₂H₄ | 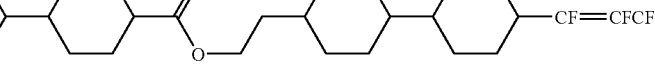 |

| | Ra | $-A^1-Z^1+(A^2-Z^2)_p+(A^3-Z^3)_q$ —[cyclohexyl]—CF=CFCF$_3$ |
|---|---|---|
| (1-cb-1) | CH$_3$, C$_2$H$_5$, C$_5$H$_{11}$, CH$_3$OCH$_2$, CH$_2$=CH | Cy–Cy–Ph–Cy–CF=CFCF$_3$ |
| (1-cb-2) | CH$_3$, C$_3$H$_7$, C$_4$H$_9$, C$_2$H$_5$O, CH$_3$CH=CH | Cy–Cy–Ph(F)–Cy–CF=CFCF$_3$ |
| (1-cb-3) | C$_2$H$_5$, C$_3$H$_7$, C$_4$H$_9$, C$_3$H$_7$O, C$_3$H$_7$CH=CH | Cy–Cy–Ph(F,F)–Cy–CF=CFCF$_3$ |
| (1-cb-4) | CH$_3$, C$_2$H$_5$, C$_5$H$_{11}$, C$_2$H$_5$O, CH$_2$=CH | Cy–Cy–CH$_2$CH$_2$–Ph–Cy–CF=CFCF$_3$ |
| (1-cb-5) | C$_3$H$_7$, C$_4$H$_9$, C$_5$H$_{11}$, C$_4$H$_9$O, CH$_2$=CHC$_2$H$_4$ | Cy–Cy–CH$_2$CH$_2$–Ph(F)–Cy–CF=CFCF$_3$ |
| (1-cb-6) | C$_2$H$_5$, C$_3$H$_7$, C$_5$H$_{11}$, CH$_3$S, CH$_3$CH=CHC$_2$H$_4$ | Cy–Cy–CH$_2$CH$_2$–Ph(F,F)–Cy–CF=CFCF$_3$ |
| (1-cb-7) | C$_2$H$_5$, C$_3$H$_7$, C$_4$H$_9$, CH$_3$OCH$_2$, CH$_3$CH=CH | Cy–Cy–COO–Ph–Cy–CF=CFCF$_3$ |
| (1-cb-8) | CH$_3$, C$_3$H$_7$, C$_4$H$_9$, C$_2$H$_5$O, CH$_3$CH$_2$=CH | Cy–Cy–Ph–CF$_2$O–Cy–CF=CFCF$_3$ |
| (1-cb-9) | C$_3$H$_7$, C$_4$H$_9$, C$_5$H$_{11}$, CH$_3$OCH$_2$, CH$_2$=CH | Cy–Cy–Ph(F)–CF$_2$O–Cy–CF=CFCF$_3$ |
| (1-cb-10) | NCC$_2$H$_4$, C$_4$H$_9$, C$_7$H$_{15}$, C$_3$H$_7$O, CH$_2$=CHC$_2$H$_4$ | Cy–Cy–Ph(F,F)–CF$_2$O–Cy–CF=CFCF$_3$ |

-continued

| | Ra | $-A^1-Z^1+(A^2-Z^2)_p+(A^3-Z^3)_q$ —[cyclohexyl]— CF=CFCF$_3$ |
|---|---|---|
| (1-cc-1) | C$_2$H$_5$, C$_3$H$_7$, C$_4$H$_9$, CH$_3$O, C$_2$H$_5$CH=CH | —[Cy]—[Ph]—[Ph]—[Cy]—CF=CFCF$_3$ |
| (1-cc-2) | CH$_3$, C$_3$H$_7$, C$_4$H$_9$, C$_2$H$_5$O, CH$_3$CH=CH | —[Cy]—[Ph]—[Ph(F)]—[Cy]—CF=CFCF$_3$ |
| (1-cc-3) | C$_3$H$_7$, C$_4$H$_9$, CH$_3$(CH$_3$)CH$_2$, CH$_3$OCH$_2$, CH$_2$=CH | —[Cy]—[Ph(F)]—[Ph]—[Cy]—CF=CFCF$_3$ |
| (1-cc-4) | CH$_3$, C$_3$H$_7$, C$_5$H$_{11}$, C$_2$H$_5$O, CH$_3$CH=CH | —[Cy]—[Ph]—CH$_2$CH$_2$—[Ph]—[Cy]—CF=CFCF$_3$ |
| (1-cc-5) | C$_2$H$_5$, C$_4$H$_9$, C$_6$H$_{13}$, C$_2$H$_5$CO, CH$_2$=CHC$_2$H$_4$ | —[Cy]—[Ph]—(CH$_2$)$_3$—[Ph]—[Cy]—CF=CFCF$_3$ |
| (1-cc-6) | C$_2$H$_5$, C$_5$H$_{11}$, C$_8$H$_{17}$, CH$_3$O, CH$_3$CH=CHC$_2$H$_4$ | —[Cy]—[Ph]—COO—[Ph]—[Cy]—CF=CFCF$_3$ |
| (1-cc-7) | C$_3$H$_7$, C$_4$H$_9$, C$_5$H$_{11}$, C$_4$H$_9$O, CH$_2$=CH | —[Cy]—[Ph]—CF$_2$O—[Ph]—[Cy]—CF=CFCF$_3$ |
| (1-cc-8) | CH$_3$, C$_2$H$_5$, C$_4$H$_9$, C$_2$H$_5$O, CH$_3$C≡C | —[Cy]—[Ph]—C≡C—[Ph]—[Cy]—CF=CFCF$_3$ |
| (1-cc-9) | CH$_3$, C$_3$H$_7$, C$_4$H$_9$, C$_2$H$_5$O, CH$_3$CH=CH | —[Cy]—[Ph]—[Ph]—[Ph]—[Cy]—CF=CFCF$_3$ |
| (1-cc-10) | C$_2$H$_5$, C$_3$H$_7$, C$_5$H$_{11}$, C$_4$H$_9$O, C$_2$H$_5$CH=CH | —[Cy]—[Pyridyl]—[Ph]—[Cy]—CF=CFCF$_3$ |
| (1-cc-11) | C$_2$H$_5$, C$_3$H$_7$, C$_5$H$_{11}$, C$_3$H$_7$O, CH$_2$=CH | —[Cy]—[Cy]—[Ph(Cl)]—[Cy]—CF=CFCF$_3$ |
| (1-cc-12) | C$_2$H$_5$, C$_3$H$_7$, C$_5$H$_{11}$, C$_3$H$_7$O, CH$_2$=CH | —[Naphthyl]—[Cy]—[Cy]—CF=CFCF$_3$ |

| Ra | —A¹—Z¹—(A²—Z²)ₚ—(A³—Z³)_q—⌬—CF=CFCF₃ |
|---|---|
| (1-cc-13) C₂H₅, C₅H₁₁, C₆H₁₃, C₂H₅O, CH₃CH=CHC₂H₄ | 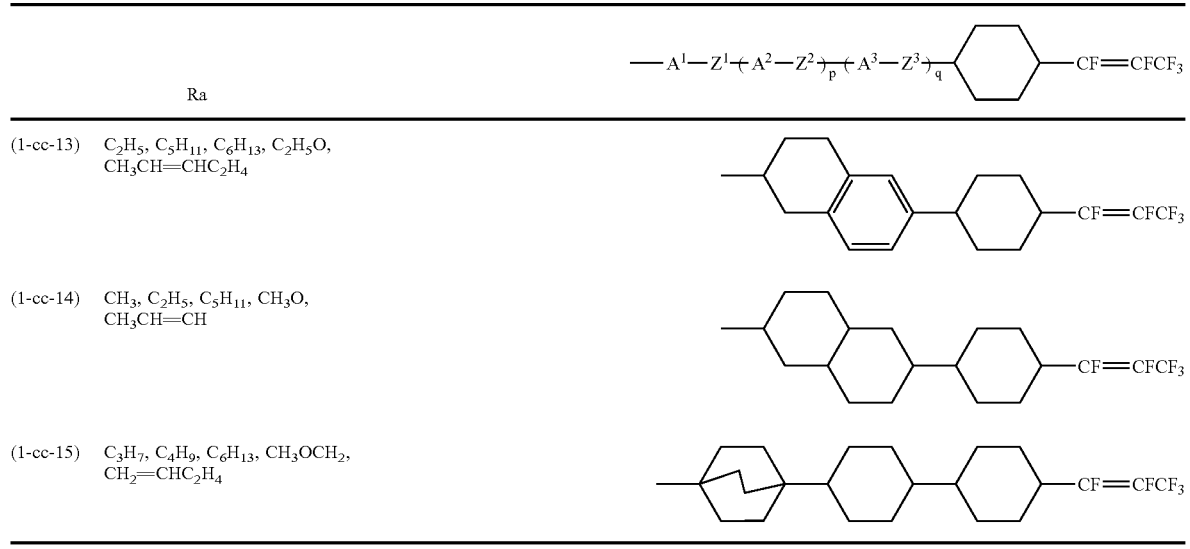 |
| (1-cc-14) CH₃, C₂H₅, C₅H₁₁, CH₃O, CH₃CH=CH | |
| (1-cc-15) C₃H₇, C₄H₉, C₆H₁₃, CH₃OCH₂, CH₂=CHC₂H₄ | |

TABLE 1

Notation of compounds using codes
R—(A₁)—Z₁— . . . —Zₙ—(Aₙ)—X

| 1) Left end group R— | Code | 3) Bonding group —Zₙ— | Code |
|---|---|---|---|
| $C_nH_{2n+1}$— | n- | —$C_2H_4$— | 2 |
| $C_nH_{2n+1}OC_mH_{2m}$— | nOm- | —$C_4H_8$— | 4 |
| $CH_2$=CH— | V- | —CH=CH— | V |
| $C_nH_{2n+1}$CH=CH— | nV- | —$CH_2O$— | 1O |
| $CH_2$=CH$C_nH_{2n}$— | Vn- | —COO— | E |
| $C_nH_{2n+1}$CH=CH$C_mH_{2m}$— | nVm- | —C≡C— | T |
| $CF_2$=CH— | VFF- | —$CF_2O$— | X |
| $CF_2$=CH$C_nH_{2n}$— | VFFn- | | |

| 2) Ring structure —Aₙ— | Code | 4) Right end group —X | Code |
|---|---|---|---|
| (benzene ring) | B | —F | —F |
| | | —Cl | —CL |
| | | —CN | —C |
| | | —$OCF_2H$ | —OCF2H |
| (fluorobenzene) | B(F) | —$OCF_3$ | —OCF3 |
| | | —$CF_3$ | —CF3 |
| | | —$C_nH_{2n+1}$ | -n |
| | | —$OC_nH_{2n+1}$ | -On |
| | | —CH=$CH_2$ | -V |
| (difluorobenzene) | B(F, F) | —$C_nH_{2n}$CH=$CH_2$ | -nV |
| | | —$C_nH_{2n}$CH=CH$C_mH_{2m+1}$ | -nVm |
| | | —CH=$CF_2$ | -VFF |
| | | —$COOCH_3$ | -EMe |
| | | —CF=$CFCF_3$ | —CF=CFCF3 |
| (2,3-difluorobenzene) | B(2F, 3F) | | |
| (pyrimidine) | Py | | |

TABLE 1-continued

Notation of compounds using codes
R—(A₁)—Z₁— ... —Zₙ—(Aₙ)—X

| Structure | Code |
|---|---|
| cyclohexane ring | H |
| 1,3-dioxane ring | G |

5) Notation example

Instance 1   7-HB(F)—F

C₇H₁₅—(cyclohexyl)—(difluorophenyl)—F

Instance 3   5-HH—CF=CFCF3

C₅H₁₁—(cyclohexyl)—(cyclohexyl)—CF=CFCF₃ (with F substituents)

Instance 2   1O1-HBBH-5

CH₃OCH₂—(cyclohexyl)—(phenyl)—(phenyl)—(cyclohexyl)—C₅H₁₁

Representative compounds of the present invention are mentioned in Examples 5 to 19. Firstly, compounds for the composition and their amounts (% by weight) are shown. According to the stipulation in the above Table 1, a compound is indicated by means of the symbols for left end group, bonding group, ring structure and right end group. Steric configuration of 1,4-cyclohexylene and 1,3-dioxane-2,5-diyl is trans. Steric configuration of perfluoropropenyl (—CF=CFCF₃) is an E substance. When there is no symbol for the end group, that means the end group is hydrogen. Numbers in the parentheses correspond to the compounds mentioned in the above Table. After that, physical property of the composition is shown. Measurement of the physical property was in accordance with a method mentioned in the Standard of Electronic Industries Association of Japan, EIAJ/ED-2521A, or with a modified method thereof.

Transition temperature of nematic phase-isotropic phase (clear point: NI; ° C.): A sample was placed on a hot plate of a melting point measuring device equipped with a polarization microscope and heated at the rate of 1° C. per minute. Temperature when a part of the sample changed from a nematic phase to an isotropic phase was measured. A phase transition temperature of the compound was also measured by that method.

Viscosity (η; measured at 20° C.; mPa·s): A viscometer of type E was used for the measurement of viscosity.

Optical anisotropy (refractive index anisotropy: Δn; measured at 25° C.): Optical anisotropy was measured by an Abbe's refractometer using light of 589 nm wavelength.

Dielectric anisotropy (Δ∈; Measured at 25° C.)

1) Composition where the value of Δ∈ is positive: A sample was placed in a liquid crystal cell where the gap of two glass substrate plates was 9 μm and the twist angle was 80°. Twenty volts were applied to this cell and dielectric constant (∈∥) in the long axis direction of the liquid crystal molecule was measured. Dielectric constant (∈⊥) of the liquid crystal molecule in the short axis direction was measured by application of 0.5 volt. Value of the dielectric anisotropy was calculated from the formula Δ∈=∈∥-∈⊥.

2) Composition where the value of Δ∈ is negative: A sample was placed in a liquid crystal cell subjected to a homeotropic orientation treatment and 0.5 volt was applied to measure the dielectric constant (∈∥). A sample was placed in a liquid crystal cell subjected to a homogeneous orientation treatment and 0.5 volt was applied to measure the dielectric constant (∈⊥). Value of the dielectric anisotropy was calculated from the formula Δ∈=∈∥-∈⊥.

Threshold voltage (Vth; measured at 25° C., volt(s)): A sample was placed in a liquid crystal display element of a normally white mode where the gap between two glass substrate plates was (0.5/Δn) μm and the twist angle was 80°. Δn is a value of optical anisotropy measured by the above method. To this element were applied square waves where frequency was 32 Hz. Voltage of the square waves was raised and the value of the voltage when the light transmission passed through the element became 90% was measured.

Helical pitch (measured at 25° C.; μm): For the measurement of helical pitch, Cano's wedge-shaped cell method was used. A sample was placed in Cano's wedge-shaped cell and interval (a; unit: μm) of disclination lines observed from the cell was measured. The helical pitch (P) was calculated from the formula P=2×a×tan θ. θ is an angle between two glass plates in the wedge-shaped cell.

Example 5

| | | |
|---|---|---|
| 3-HH—CF=CFCF3 | (1-aa-1) | 6% |
| 4-HH—CF=CFCF3 | (1-aa-1) | 5% |
| 5-HH—CF=CFCF3 | (1-aa-1) | 5% |
| 2-BEB(F)—C | (5) | 5% |
| 3-BEB(F)—C | (5) | 4% |
| 4-BEB(F)—C | (5) | 12% |
| 1V2-BEB(F,F)—C | (5) | 16% |
| 3-HB—O2 | (10-5) | 2% |
| 3-HH-4 | (10-1) | 3% |
| 3-HHB—F | (3-1) | 3% |

-continued

| | | |
|---|---|---|
| 3-HHB-1 | (11-1) | 4% |
| 3-HHB—O1 | (11-1) | 4% |
| 3-HBEB—F | (3-34) | 4% |
| 3-HHEB—F | (3-10) | 5% |
| 5-HHEB—F | (3-10) | 5% |
| 3-H2BTB-2 | (11-15) | 4% |
| 3-H2BTB-3 | (11-15) | 4% |
| 3-H2BTB-4 | (11-15) | 4% |
| 3-HB(F)TB-2 | (11-14) | 5% |

NI = 79.6° C.; Δn = 0.138; η = 39.6 mPa · s ; Δε = 28.9; Vth = 1.01 V.

Example 6

| | | |
|---|---|---|
| 5-HH—CF=CFCF3 | (1-aa-1) | 5% |
| 2-H2H—CF=CFCF3 | (1-aa-2) | 5% |
| 3-HVH—CF=CFCF3 | (1-aa-4) | 5% |
| V—HHH—CF=CFCF3 | (1-ba-1) | 5% |
| 2-HB—C | (5-2) | 5% |
| 3-HB—C | (5-2) | 12% |
| 3-HB—O2 | (10-5) | 5% |
| 2-BTB-1 | (10-10) | 3% |
| 3-HHB—F | (3-1) | 4% |
| 3-HHB-1 | (11-1) | 8% |
| 3-HHB—O1 | (11-1) | 5% |
| 3-HHB-3 | (11-1) | 4% |
| 3-HHEB—F | (3-10) | 4% |
| 5-HHEB—F | (3-10) | 4% |
| 2-HHB(F)—F | (3-2) | 7% |
| 5-HHB(F)—F | (3-2) | 7% |
| 3-HHB(F,F)—F | (3-3) | 5% |

NI = 92.9° C.; Δn = 0.092; η = 20.0 mPa · s; Δε = 5.6; Vth = 2.30 V.

Example 7

| | | |
|---|---|---|
| 4-HH—CF=CFCF3 | (1-aa-1) | 5% |
| 4-HEH—CF=CFCF3 | (1-aa-5) | 10% |
| 1O1—H2HH—CF=CFCF3 | (1-ba-12) | 6% |
| 3-BEB(F)—C | (5) | 8% |
| 3-HB—C | (5-2) | 8% |
| V—HB—C | (5-2) | 8% |
| 1V—HB—C | (5-2) | 8% |
| 3-HB—O2 | (10-5) | 3% |
| 3-HH—2V | (10-1) | 3% |
| 3-HH—2V1 | (10-1) | 3% |
| V2-HHB-1 | (11-1) | 9% |
| 3-HHB-1 | (11-1) | 5% |
| 3-HHEB—F | (3-10) | 7% |
| 3-H2BTB-2 | (11-15) | 6% |
| 3-H2BTB-3 | (11-15) | 6% |
| 3-H2BTB-4 | (11-15) | 5% |

NI = 84.3° C.; Δn = 0.127; η = 19.7 mPa · s; Δε = 9.5; Vth = 2.07 V.

Example 8

| | | |
|---|---|---|
| V—H1OH—CF=CFCF3 | (1-aa-3) | 4% |
| 3-HVHH—CF=CFCF3 | (1-ba-14) | 5% |
| 3-HEHH—CF=CFCF3 | (1-ba-18) | 5% |
| 5-BEB(F)—C | (5) | 5% |
| V—HB—C | (5-2) | 11% |
| 5-PyB—C | (5-8) | 6% |
| 4-BB-3 | (10-8) | 11% |

-continued

| | | |
|---|---|---|
| 3-HH—2V | (10-1) | 10% |
| 5-HH—V | (10-1) | 11% |
| V—HHB-1 | (11-1) | 7% |
| V2-HHB-1 | (11-1) | 7% |
| 3-HHB-1 | (11-1) | 3% |
| 1V2-HBB-2 | (11-4) | 10% |
| 3-HHEBH-3 | (12-6) | 5% |

NI = 81.7° C.; Δn = 0.109; η = 16.7 mPa · s; Δε = 5.5; Vth = 2.36 V.

Example 9

| | | |
|---|---|---|
| 3-HH—CF=CFCF3 | (1-aa-1) | 8% |
| 2-H2H—CF=CFCF3 | (1-aa-2) | 6% |
| 4-H1OHH—CF=CFCF3 | (1-ba-13) | 8% |
| 1V2-BEB(F,F)—C | (5) | 6% |
| 3-HB—C | (5-2) | 18% |
| 2-BTB-1 | (10-10) | 10% |
| 5-HH—VFF | (10-1) | 20% |
| 3-HHB-1 | (11-1) | 3% |
| VFF—HHB-1 | (11-1) | 4% |
| VFF2—HHB-1 | (11-1) | 4% |
| 3-H2BTB-2 | (11-15) | 5% |
| 3-H2BTB-3 | (11-15) | 4% |
| 3-H2BTB-4 | (11-15) | 4% |

NI = 68.9° C.; Δn = 0.123; η = 14.7 mPa · s; Δε = 7.5; Vth = 1.98 V.

Example 10

| | | |
|---|---|---|
| 5-HH—CF=CFCF3 | (1-aa-1) | 5% |
| 3-HVH—CF=CFCF3 | (1-aa-4) | 6% |
| 4-HEH—CF=CFCF3 | (1-aa-5) | 7% |
| V—HHH—CF=CFCF3 | (1-ba-1) | 7% |
| 5-HB—CL | (2-1) | 6% |
| 3-HH-4 | (10-1) | 4% |
| 3-HH-5 | (10-1) | 2% |
| 3-HHB—F | (3-1) | 2% |
| 3-HHB—CL | (3-1) | 2% |
| 4-HHB—CL | (3-1) | 2% |
| 3-HHB(F)—F | (3-2) | 10% |
| 4-HHB(F)—F | (3-2) | 9% |
| 5-HHB(F)—F | (3-2) | 9% |
| 7-HHB(F)—F | (3-2) | 8% |
| 5-HBB(F)—F | (3-23) | 4% |
| 1O1—HBBH-5 | (12-1) | 3% |
| 3-HHBB(F,F)—F | (4-6) | 2% |
| 4-HHBB(F,F)—F | (4-6) | 3% |
| 5-HHBB(F,F)—F | (4-6) | 3% |
| 3-HH2BB(F,F)—F | (4-15) | 3% |
| 4-HH2BB(F,F)—F | (4-15) | 3% |

NI = 113.6° C.; Δn = 0.089; η = 23.8 mPa · s; Δε = 4.7; Vth = 2.50 V.

Example 11

| | | |
|---|---|---|
| 4-HH—CF=CFCF3 | (1-aa-1) | 8% |
| 1O1—HH—CF=CFCF3 | (1-aa-1) | 6% |
| 4-HHH—CF=CFCF3 | (1-ba-1) | 5% |
| 3-HHB(F,F)—F | (3-3) | 9% |
| 3-H2HB(F,F)—F | (3-15) | 9% |
| 4-H2HB(F,F)—F | (3-15) | 8% |
| 5-H2HB(F,F)—F | (3-15) | 8% |
| 3-HBB(F,F)—F | (3-24) | 12% |

-continued

| | | |
|---|---|---|
| 5-HBB(F,F)—F | (3-24) | 12% |
| 3-H2BB(F,F)—F | (3-27) | 7% |
| 5-HHBB(F,F)—F | (4-6) | 3% |
| 5-HHEBB—F | (4) | 2% |
| 3-HH2BB(F,F)—F | (4-15) | 3% |
| 1O1—HBBH-4 | (12-1) | 4% |
| 1O1—HBBH-5 | (12-1) | 4% |

NI = 98.8° C.; Δn = 0.105; η = 31.7 mPa · s; Δε = 8.2; Vth = 1.93 V.

Example 12

| | | |
|---|---|---|
| V—H1OH—CF=CFCF3 | (1-aa-3) | 5% |
| 3-HEHH—CF=CFCF3 | (1-ba-18) | 5% |
| 5-HB—F | (2-1) | 12% |
| 6-HB—F | (2-1) | 9% |
| 7-HB—F | (2-1) | 7% |
| 2-HHB—OCF3 | (3-1) | 7% |
| 3-HHB—OCF3 | (3-1) | 7% |
| 4-HHB—OCF3 | (3-1) | 7% |
| 5-HHB—OCF3 | (3-1) | 5% |
| 3-HH2B—OCF3 | (3-4) | 4% |
| 5-HH2B—OCF3 | (3-4) | 4% |
| 3-HHB(F,F)—OCF2H | (3-3) | 4% |
| 3-HHB(F,F)—OCF3 | (3-3) | 5% |
| 3-HH2B(F)—F | (3-5) | 3% |
| 3-HBB(F)—F | (3-23) | 5% |
| 5-HBB(F)—F | (3-23) | 5% |
| 5-HBBH-3 | (12-1) | 3% |
| 3-HB(F)BH-3 | (12-2) | 3% |

NI = 81.4° C.; Δn = 0.084; η = 13.8 mPa · s; Δε = 4.3; Vth = 2.56 V.

Example 13

| | | |
|---|---|---|
| 3-HH—CF=CFCF3 | (1-aa-1) | 5% |
| 2-H2H—CF=CFCF3 | (1-aa-2) | 5% |
| 1O1—H2HH—CF=CFCF3 | (1-ba-12) | 5% |
| 5-HB—CL | (2-1) | 3% |
| 3-HH-4 | (10-1) | 8% |
| 3-HHB-1 | (11-1) | 5% |
| 3-HHB(F,F)—F | (3-3) | 8% |
| 3-HBB(F,F)—F | (3-24) | 20% |
| 5-HBB(F,F)—F | (3-24) | 8% |
| 3-HHEB(F,F)—F | (3-12) | 10% |
| 4-HHEB(F,F)—F | (3-12) | 3% |
| 5-HHEB(F,F)—F | (3-12) | 3% |
| 2-HBEB(F,F)—F | (3-36) | 3% |
| 3-HBEB(F,F)—F | (3-36) | 5% |
| 5-HBEB(F,F)—F | (3-36) | 3% |
| 3-HHBB(F,F)—F | (4-6) | 6% |

NI = 74.8° C.; Δn = 0.098; η = 26.7 mPa · s; Δε = 8.4; Vth = 1.62 V.

Example 14

| | | |
|---|---|---|
| V—HHH—CF=CFCF3 | (1-ba-1) | 4% |
| 4-H1OHH—CF=CFCF3 | (1-ba-13) | 6% |
| 3-HB—CL | (2-1) | 3% |
| 5-HB—CL | (2-1) | 2% |
| 3-HHB—OCF3 | (3-1) | 5% |
| 3-H2HB—OCF3 | (3-13) | 5% |
| 5-H4HB—OCF3 | (3-19) | 15% |
| V—HHB(F)—F | (3-2) | 5% |

| | | |
|---|---|---|
| 3-HHB(F)—F | (3-2) | 5% |
| 5-HHB(F)—F | (3-2) | 5% |
| 3-H4HB(F,F)—CF3 | (3-21) | 8% |
| 5-H4HB(F,F)—CF3 | (3-21) | 10% |
| 5-H2HB(F,F)—F | (3-15) | 5% |
| 5-H4HB(F,F)—F | (3-21) | 7% |
| 2-H2BB(F)—F | (3-26) | 5% |
| 3-H2BB(F)—F | (3-26) | 5% |
| 3-HBEB(F,F)—F | (3-36) | 5% |

NI = 79.2° C.; Δn = 0.095; η (20° C.) = 28.4 mPa · s; Δε = 8.6; Vth = 1.73 V.

Example 15

| | | |
|---|---|---|
| 2-H2H—CF=CFCF3 | (1-aa-2) | 7% |
| 4-HEH—CF=CFCF3 | (1-aa-5) | 7% |
| 3-HEHH—CF=CFCF3 | (1-ba-18) | 8% |
| 5-HB—CL | (2-1) | 5% |
| 7-HB(F,F)—F | (2-3) | 3% |
| 3-HH-4 | (10-1) | 10% |
| 3-HH-5 | (10-1) | 5% |
| 3-HB—O2 | (10-5) | 5% |
| 3-HHB-1 | (11-1) | 8% |
| 3-HHB—O1 | (11-1) | 5% |
| 2-HHB(F)—F | (3-2) | 7% |
| 3-HHB(F)—F | (3-2) | 7% |
| 5-HHB(F)—F | (3-2) | 7% |
| 3-HHB(F,F)—F | (3-3) | 6% |
| 3-H2HB(F,F)—F | (3-15) | 5% |
| 4-H2HB(F,F)—F | (3-15) | 5% |

NI = 75.4° C.; Δn = 0.068; η(20° C.) = 18.8 mPa · s; Δε = 3.2; Vth = 1.99 V.

Example 16

| | | |
|---|---|---|
| 3-HH—CF=CFCF3 | (1-aa-1) | 5% |
| 3-HVH—CF=CFCF3 | (1-aa-4) | 5% |
| 4-HHH—CF=CFCF3 | (1-ba-1) | 5% |
| 3-HVHH—CF=CFCF3 | (1-ba-14) | 5% |
| 5-HB—CL | (2-1) | 3% |
| 7-HB(F)—F | (2-2) | 5% |
| 3-HH-4 | (10-1) | 9% |
| 3-HH-EMe | (10-2) | 5% |
| 3-HHEB—F | (3-10) | 8% |
| 5-HHEB—F | (3-10) | 8% |
| 3-HHEB(F,F)—F | (3-12) | 10% |
| 4-HHEB(F,F)—F | (3-12) | 5% |
| 4-HGB(F,F)—F | (3-91) | 5% |
| 5-HGB(F,F)—F | (3-91) | 6% |
| 2-H2GB(F,F)—F | (3-94) | 4% |
| 3-H2GB(F,F)—F | (3-94) | 5% |
| 5-GHB(F,F)—F | (3-97) | 7% |

NI = 85.3° C.; Δn = 0.067; η = 23.2 mPa · s; Δε = 7.2; Vth = 1.48 V.

Example 17

| | | |
|---|---|---|
| 5-HH—CF=CFCF3 | (1-aa-1) | 5% |
| V—H1OH—CF=CFCF3 | (1-aa-3) | 10% |
| V—HHH—CF=CFCF3 | (1-ba-1) | 5% |
| 3-HH-4 | (10-1) | 8% |
| 3-HHB-1 | (11-1) | 6% |

-continued

| | | |
|---|---|---|
| 3-HHB(F,F)—F | (3-3) | 10% |
| 3-H2HB(F,F)—F | (3-15) | 9% |
| 3-HBB(F,F)—F | (3-24) | 5% |
| 3-BB(F,F)XB(F,F)—F | (3-85) | 25% |
| 1O1—HBBH-5 | (12-1) | 7% |
| 2-HHBB(F,F)—F | (4-6) | 3% |
| 3-HHBB(F,F)—F | (4-6) | 3% |
| 3-HH2BB(F,F)—F | (4-15) | 4% |

NI = 82.4° C.; Δn = 0.101; η = 23.1 mPa · s; Δε = 9.5; Vth = 1.47 V.

Example 18

| | | |
|---|---|---|
| 4-HH—CF=CFCF3 | (1-aa-1) | 6% |
| 2-H2H—CF=CFCF3 | (1-aa-2) | 6% |
| 1O1—H2HH—CF=CFCF3 | (1-ba-12) | 5% |
| 3-HH-4 | (10-1) | 5% |
| 3-HH-5 | (10-1) | 5% |
| 3-HH—O1 | (10-1) | 3% |
| 3-HH—O3 | (10-1) | 3% |
| 3-HB—O1 | (10-5) | 5% |
| 3-HB—O2 | (10-5) | 5% |
| 3-HB(2F,3F)—O2 | (7-1) | 10% |
| 5-HB(2F,3F)—O2 | (7-1) | 10% |
| 3-HHEH-3 | (11) | 3% |
| 3-HHEH-5 | (11) | 2% |
| 4-HHEH-3 | (11) | 2% |
| 2-HHB(2F,3F)-1 | (8-1) | 4% |
| 3-HHB(2F,3F)-2 | (8-1) | 4% |
| 3-HHB(2F,3F)—O2 | (8-1) | 12% |
| 5-HHB(2F,3F)—O2 | (8-1) | 10% |

NI = 72.8° C.; Δn = 0.075; η = 25.9 mPa · s; Δε = −2.5.

Example 19

| | | |
|---|---|---|
| 2-HHEBH—CF=CFCF3 | (1-cb-7) | 2% |
| 3-HHEBH—CF=CFCF3 | (1-cb-7) | 2% |
| 4-HHEBH—CF=CFCF3 | (1-cb-7) | 2% |
| 3-HHB(F,F)—F | (3-3) | 9% |
| 3-H2HB(F,F)—F | (3-5) | 8% |
| 4-H2HB(F,F)—F | (3-15) | 8% |
| 5-H2HB(F,F)—F | (3-15) | 8% |
| 3-HBB(F,F)—F | (3-24) | 21% |
| 5-HBB(F,F)—F | (3-24) | 20% |
| 3-H2BB(F,F)—F | (3-27) | 10% |
| 5-HHBB(F,F)—F | (4-6) | 2% |
| 5-HHEBB—F | (4) | 2% |
| 3-HH2BB(F,F)—F | (4-15) | 2% |
| 1O1—HBBH-4 | (12-1) | 2% |
| 1O1—HBBH-5 | (12-1) | 2% |

NI = 96.8° C.; Δn = 0.112; η = 35.3 mPa · s; Δε = 9.4; Vth = 1.68 V.

When an optically active compound (OP-5) in an amount of 0.25% to the composition was added in the above Example 11, the value of the helical pitch was 63.0 μm.

What is claimed is:

1. A compound represented by the formula (1):

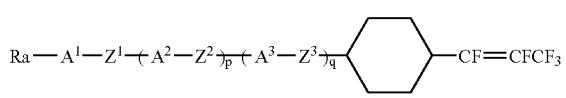

(1)

wherein Ra is alkyl having 1 to 10 carbon(s) and, in that alkyl, any of —CH$_2$— may be replaced with —O—, —S—, —CO—, —CH=CH— or —C≡C— or any of hydrogens may be replaced with halogen or —CN; A$^1$, A$^2$ and A$^3$ are independently 1,4-cycolohexylene, 1,4-cyclohexenylene, 1,4-phenylene, naphthalene-2,6-diyl, 1,2,3,4-tetrahydronaphthalene-2,6-diyl, decahydro- naphthalene-2,6-diyl or 1,4-bicyclo[2.2.2]octylene and, in such a ring, any —CH$_2$— may be replaced with —O—, any —CH= may be replaced with —N= and any hydrogen may be replaced with halogen; Z$^1$, Z$^2$ and Z$^3$ are independently a single bond, —(CH$_2$)$_2$—, —(CF$_2$)$_2$—, —COO—, —OCO—, —CH$_2$O—, —OCH$_2$—, —CF$_2$O—, —OCF$_2$—, —CH=CH—, —CF=CF—, —C≡C—, —(CH$_2$)$_4$—, —(CH$_2$)$_3$O— or —O(CH$_2$)$_3$—; p and q are independently 0 or 1.

2. A compound represented by the formula (1):

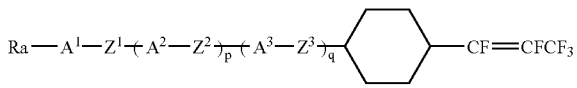

(1)

wherein Ra is alkyl having 1 to 10 carbon(s) where any —CH$_2$— in the alkyl may be replaced with —O— or —CH=CH— and any hydrogen may be replaced with halogen; A$^1$, A$^2$ and A$^3$ are independently 1,4-cyclohexylene, 1,3-dioxane-2,5-diyl, 1,4-phenylene where any hydrogen may be replaced with halogen, pyridine-2,5-diyl where any hydrogen may be replaced with halogen or pyrimidine-2,5-diyl; Z$^1$, Z$^2$ and Z$^3$ are independently —(CH$_2$)$_2$—, —CH$_2$O—, —OCH$_2$—, —COO—, —OCO—, —CF$_2$O—, —OCF$_2$—, —CH=CH—, —C≡C— or —(CH$_2$)$_4$—: and p and q are independently 0 or 1.

3. The compound according to claim 2, wherein, A$^1$, A$^2$ and A$^3$ are independently 1,4-cyclohexylene, 1,3-dioxane-2,5-diyl or 1,4-phenylene where any hydrogen may be replaced with halogen.

4. The compound according to claim 2, wherein, A$^1$, A$^2$ and A$^3$ are 1,4-cyclohexylene.

5. The compound according to claim 2, wherein, p and q are 0.

6. The compound according to claim 2, wherein, p is 1 and q is 0.

7. The compound according to claim 2, wherein, p and q are 1.

8. A compound which is represented by any one of the following formulas (1-a) to (1-c):

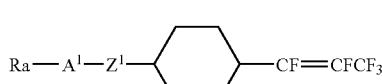

(1-a)

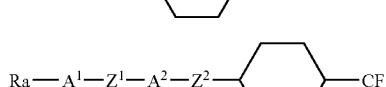

(1-b)

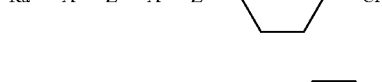

(1-c)

wherein Ra is alkyl having 1 to 10 carbon(s) and, in that alkyl, any —CH$_2$— may be replaced with —O— or —CH═CH— and any hydrogen may be replaced with fluorine; A$^1$, A$^2$ and A$^3$ are independently 1,4-cyclohexylene, 1,3-dioxane-2,5-diyl or 1,4-phenylene where any hydrogen may be replaced with fluorine; and Z$^1$, Z$^2$ and Z$^3$ are independently a single bond, —(CH$_2$)$_2$—, —CH$_2$O—, —OCH$_2$—, —COO—, —OCO—, —CF$_2$O—, —OCF$_2$—, —CH═CH—, —C≡C— or —(CH$_2$)$_4$—.

9. The compound according to claim 8, wherein, in the formulas (1-a) to (1-c), Ra is alkyl, alkoxy, alkenyl or alkenyloxy; and A$^1$, A$^2$ and A$^3$ are independently 1,4-cyclohexylene, 1,3-dioxane-2,5-diyl or 1,4-phenylene.

10. The compound according to claim 8, wherein, in the formulas (1-a) to (1-c), Ra is alkyl, alkoxy, alkenyl or alkenyloxy; and at least one of A$^1$, A$^2$ and A$^3$ is 2-fluoro-1,4-phenylene or 2,6-difluoro-1,4-phenylene.

11. The compound according to claim 8, wherein, in the formulas (1-a) to (1-c), Ra is alkyl, alkoxy, alkenyl or alkenyloxy; and at least one of A$^1$, A$^2$ and A$^3$ is 2,3-difluoro-1,4-phenylene.

12. The compound according to claim 8, wherein, in the formulas (1-a) to (1-c), Z$^1$, Z$^2$ and Z$^3$ are independently a single bond or —(CH$_2$)$_2$—.

13. The compound according to claim 8, wherein, in the formula (1-a), Ra is alkyl, alkoxy, alkenyl or alkenyloxy; A$^1$ is 1,4-cyclohexylene; and Z$^1$ is a single bond.

14. The compound according to claim 8, wherein, in the formula (1-b), Ra is alkyl, alkoxy, alkenyl or alkenyloxy; A$^1$ and A$^2$ are 1,4-cyclohexylene; and Z$^1$ and Z$^2$ are a single bond.

15. A liquid crystal composition comprising at least two compounds, at least one of which is a compound according to claim 1.

16. The composition according to claim 15, which comprises at least one compound selected from the group of the compounds represented by the following formulas (2), (3) and (4):

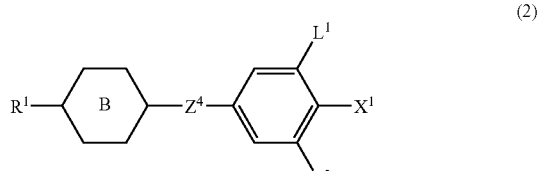

(2)

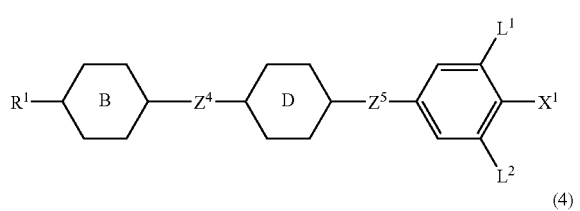

(3)

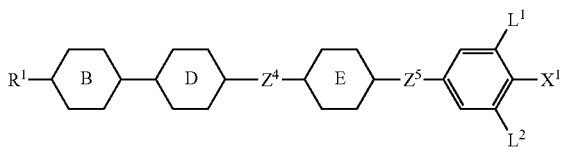

(4)

wherein R$^1$ is alkyl having 1 to 10 carbon(s) and, in this alkyl, any —CH$_2$— may be replaced with —O— or —CH═CH— and any hydrogen may be replaced with fluorine; X$^1$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$; ring B and ring D are independently 1,4-cyclohexylene, 1,3-dioxane-2,5-diyl or 1,4-phenylene where any hydrogen may be replaced with fluorine; ring E is 1,4-cyclohexylene or 1,4-phenylene where any hydrogen may be replaced with fluorine; Z$^4$ and Z$^5$ are independently —(CH$_2$)$_2$—, —(CH$_2$)$_4$—, —COO—, —CF$_2$O—, —OCF$_2$—, —CH═CH— or a single bond; and L$^1$ and L$^2$ are independently hydrogen or fluorine.

17. The compound according to claim 15 which comprises at least one compound selected from the group of compounds represented by the following formulas (5) and (6):

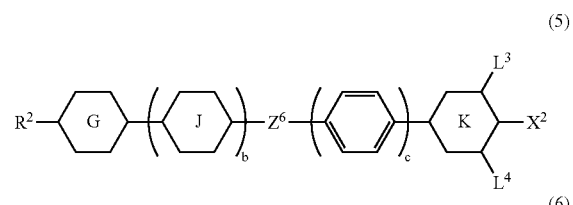

(5)

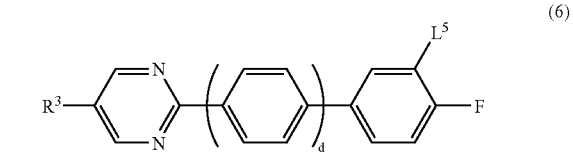

(6)

wherein R$^2$ and R$^3$ are independently alkyl having 1 to 10 carbon(s) and, in that alkyl, any —CH$_2$— may be replaced with —O— or —CH═CH— and any hydrogen may be replaced with fluorine; X$^2$ is —CN or —C≡C—CN; ring G is 1,4-cyclohexylene, 1,4-phenylene, 1,3-dioxane-2,5-diyl or pyrimidine-2,5-diyl; ring J is 1,4-cyclohexylene, pyrimidine-2,5-diyl or 1,4-phenylene where any hydrogen may be replaced with fluorine; ring K is 1,4-cyclohexylene or 1,4-phenylene; Z$^6$ is CH$_2$)$_2$—, —COO—, —CF$_2$O—, —OCF$_2$— or a single bond; L$^3$, L$^4$ and L$^5$ are independently hydrogen or fluorine; and b, c and d are independently 0 or 1.

18. The composition according to claim 15, which comprises at least one compound selected from the group of compounds represented by the following formulas (7), (8) and (9):

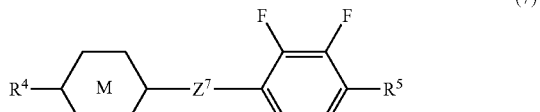

(7)

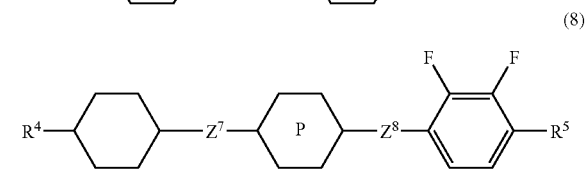

(8)

-continued

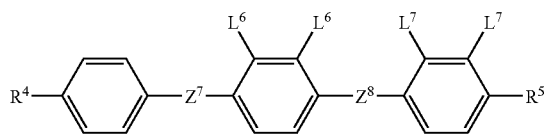
(9)

wherein $R^4$ and $R^5$ are independently alkyl having 1 to 10 carbon(s) and, in that alkyl, any —CH$_2$— may be replaced with —O— or —CH=CH— and any hydrogen may be replaced with fluorine; ring M and ring P are independently 1,4-cyclohexylene or 1,4-phenylene; $Z^7$ and $Z^8$ are independently —(CH$_2$)$_2$—, —COO— or a single bond; and $L^6$ and $L^7$ are independently hydrogen or fluorine where at least one of $L^6$ and $L^7$ is fluorine.

19. The composition according to claim 15, which comprises at least one compound selected from the group of compounds represented by the following formulas (10), (11) and (12):

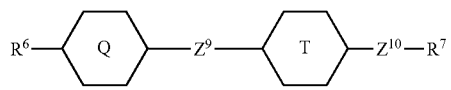
(10)

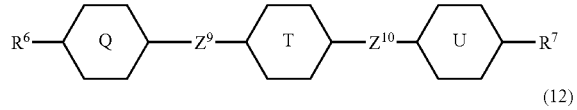
(11)

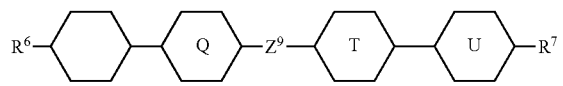
(12)

wherein $R^6$ and $R^7$ are independently alkyl having 1 to 10 carbon(s) and, in that alkyl, any —CH$_2$— may be replaced with —O— or —CH=CH— and any hydrogen may be replaced with fluorine; ring Q, ring T and ring U are independently 1,4-cyclohexylene, pyrimidine-2,5-diyl or 1,4-phenylene where any hydrogen may be replaced with fluorine; and $Z^9$ and $Z^{10}$ are independently —C≡C—, —COO—, —(CH$_2$)$_2$, —CH=CH— or a single bond.

20. The composition according to claim 16, which further comprises at least one compound selected from the group of the compounds represented by the formulas (10), (11) and (12):

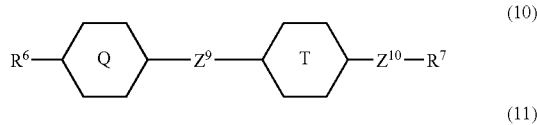
(10)

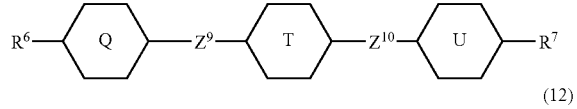
(11)

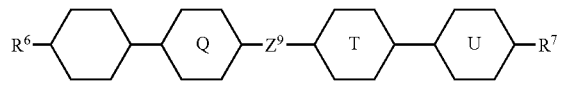
(12)

wherein $R^6$ and $R^7$ are independently alkyl having 1 to 10 carbon(s) and, in that alkyl, any —CH$_2$— may be replaced with —O— or —CH=CH— and any hydrogen may be replaced with fluorine; ring Q, ring T and ring U are independently 1,4-cyclohexylene, pyrimidine-2,5-diyl or 1,4-phenylene where any hydrogen may be replaced with fluorine; and $Z^9$ and $Z^{10}$ are independently —C≡C—, —COO—, —(CH$_2$)$_2$, —CH=CH— or a single bond.

21. The composition according to claim 17, which further comprises at least one compound selected from the group of the compounds represented by the formulas (10), (11) and (12):

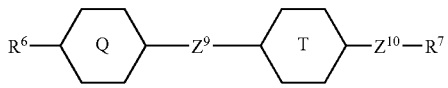
(10)

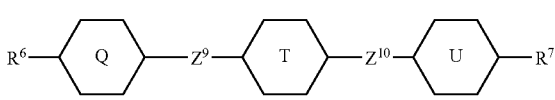
(11)

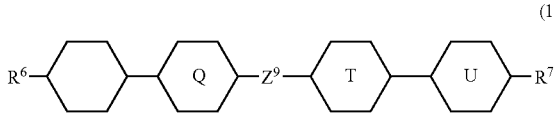
(12)

wherein $R^6$ and $R^7$ are independently alkyl having 1 to 10 carbon(s) and, in that alkyl, any —CH$_2$— may be replaced with —O— or —CH=CH— and any hydrogen may be replaced with fluorine; ring Q, ring T and ring U are independently 1,4-cyclohexylene, pyrimidine-2,5-diyl or 1,4-phenylene where any hydrogen may be replaced with fluorine; and $Z^9$ and $Z^{10}$ are independently —C≡C—, —COO—, —(CH$_2$)$_2$, —CH=CH— or a single bond.

22. The composition according to claim 18, which further comprises at least one compound selected from the group of the compounds represented by the formulas (10), (11) and (12):

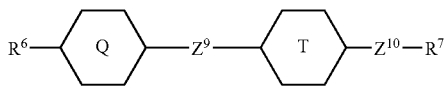
(10)

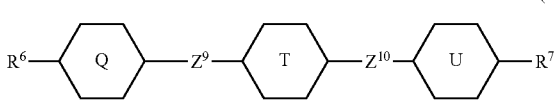
(11)

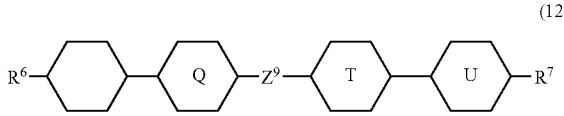
(12)

wherein $R^6$ and $R^7$ are independently alkyl having 1 to 10 carbon(s) and, in that alkyl, any —CH$_2$—, may be replaced with —O— or —CH=CH— and any hydrogen may be replaced with fluorine; ring Q, ring T and ring U are independently 1,4-cyclohexylene, pyrimidine-2,5-diyl or 1,4-phenylene where any hydrogen may be replaced with fluorine; and $Z^9$ and $Z^{10}$ are independently —C≡C—, —COO—, —(CH$_2$)$_2$, —CH=CH— or a single bond.

23. The composition according to claim 16, which further comprises at least one compound selected from the group of the compounds represented by the formulas (5) and (6):

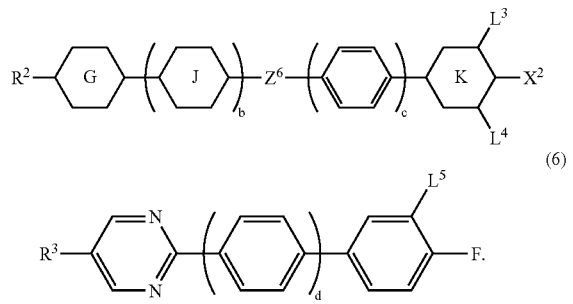

wherein $R^2$ and $R^3$ are independently alkyl having 1 to 10 carbon(s) and, in that alkyl, any —CH$_2$— may be replaced with —O— or —CH=CH— and any hydrogen may be replaced with fluorine $X^2$ is —CN or —C≡C—CN; ring G is 1,4-cyclohexylene, 1,4-phenylene, 1,3-dioxane-2,5-diyl or pyrimidine-2,5-diyl; ring J is 1,4-cyclohexylene, pyrimidine-2,5-diyl or 1,4-phenylene where any hydrogen may be replaced with fluorine; ring K is 1,4-cyclohexylene or 1,4-phenylene: $Z^6$ is —(CH$_2$)$_2$—, —COO—, —CF$_2$O—, —OCF$_2$— or a single bond; $L^3$, $L^4$ and $L^5$ are independently hydrogen or fluorine; and b, c and d are independently 0 or 1.

24. The composition according to claim 23, which further comprises at least one compound selected from the group of the compounds represented by the formulas (10), (11) and (12):

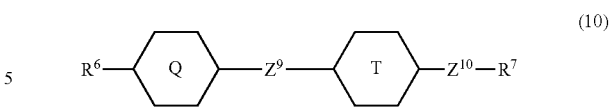

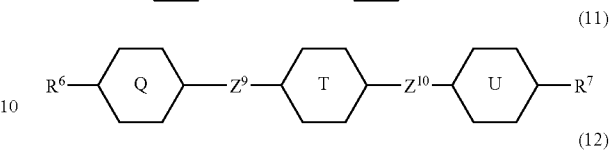

wherein $R^6$ and $R^7$ are independently alkyl having 1 to 10 carbon(s) and, in that alkyl, any —CH$_2$— may be replaced with —O— or —CH=CH— and any hydrogen may be replaced with fluorine; ring Q, ring T and ring U are independently 1,4-cyclohexylene, pyrimidine-2,5-diyl or 1,4-phenylene where any hydrogen may be replaced with fluorine: and $Z^9$ and $Z^{10}$ are independently —C≡C—, —COO—, —(CH$_2$)$_2$, —CH=CH— or a single bond.

25. The composition according to claim 15, which comprises at least one optically active compound.

26. The composition according to claim 16, which comprises at least one optically active compound.

27. A liquid crystal display element which comprises the composition according to in claim 15.

28. A liquid crystal display element which comprises the composition according to claim 16.

* * * * *